US007687529B2

(12) United States Patent
McComas et al.

(10) Patent No.: US 7,687,529 B2
(45) Date of Patent: Mar. 30, 2010

(54) SUBSTITUTED PROPYLAMINE DERIVATIVES AND METHODS OF THEIR USE

(75) Inventors: Casey Cameron McComas, Phoenixville, PA (US); Puwen Zhang, Audubon, PA (US); Eugene Anthony Terefenko, Center Valley, PA (US); An Thien Vu, Pottstown, PA (US); Stephen Todd Cohn, Spring, TX (US)

(73) Assignee: Wyeth LLC, Madison, NJ (US)

( * ) Notice: Subject to any disclaimer, the term of this patent is extended or adjusted under 35 U.S.C. 154(b) by 516 days.

(21) Appl. No.: 11/529,450

(22) Filed: Sep. 27, 2006

(65) Prior Publication Data

US 2007/0072928 A1    Mar. 29, 2007

Related U.S. Application Data

(60) Provisional application No. 60/722,052, filed on Sep. 29, 2005.

(51) Int. Cl.
*A61K 31/4184* (2006.01)
*C07D 235/04* (2006.01)
*C07D 209/04* (2006.01)

(52) U.S. Cl. .................. 514/394; 514/395; 514/415; 548/304.4; 548/306.4; 548/309.4; 548/469; 548/484

(58) Field of Classification Search .......... 548/411, 548/304.4, 306.4, 309.4, 309.7, 469, 484; 514/394, 395, 415
See application file for complete search history.

(56) References Cited

U.S. PATENT DOCUMENTS 7,517,899 B2 *   4/2009   Kim et al. ............... 514/394
2005/0222148 A1 * 10/2005   Kim et al. ............... 514/232.5

FOREIGN PATENT DOCUMENTS

| WO | 99/44601 A1 | 9/1999 |
| WO | 00/66556 A1 | 11/2000 |
| WO | 02/24661 A2 | 3/2002 |
| WO | 2005/118539 A1 | 12/2005 |

OTHER PUBLICATIONS

Patani, George A. Bioisosterism: A rational approach in drug design. Chem Rev. 96 (1996) 3147-3176.*
Mahaney, P. E. et al., "Synthesis and activity of a new class of dual acting norepinephrine and serotonin reuptake inhibitors: 3-(1H-indol-1-yl)-3-arylpropan-1- amines," *Bioorganic & Medicinal Chemistry*, 2006, 14(24), 8455-8466.
Ganellin, C. R. et al., "Amino alkylation of Metal Derivatives of Indole. Part III. Alkylation of Lithio-derivatives of N-substituted Indoles with 1-Chloro-2-dimethyl-aminoethane," *J. Chem. Soc. Section C*, 1969, 11, 1537-1540.
U.S. Appl. No. 11/529,441, filed Sep. 27, 2006, Mahaney et al.

U.S. Appl. No. 11/528,792, filed Sep. 27, 2006, McComas et al.
Berendsen, H. H. G., "Effect of tibolone and raloxifene on the tail temperature of oestrogen-deficient rats," *European Journal of Pharmacology*, 2001, 419(1), 47-54.
Berendsen, H. H. G., "The role of serotonin in hot flushes," *Maturitas*, 2000, 36(3), 155-164.
Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).
Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4), 285-298.
Bundgaard, H., "Means to enhance penetration; Prodrugs as a means to improve the delivery of peptide drugs," *Advanced Drug Deliver Reviews*, 1992, 8, 1-38.
Eliel, E. L., *Stereochemistry of Carbon Compounds*, McGraw Hill, NY (1962) Ch. 4, pp. 46-87.
Fink, G. et al., "Oestrogen and mental state," *Nature*, 1996, 383(6598), 306.
Freedman, R. R. et al., "Clonidine raises the sweating threshold in symptomatic but not asymptomatic postmenopausal women," *Fertility & Sterility*, 2000, 74(1), 20-3.
French, N., "α2-Adrenoceptors and $I_2$ sites in the mammalian central nervous system," *Pharmacol. Ther.*, 1995, 68(2), 175-208.
Greene, T.W. and Wuts, P.G.M., *Protective Groups in Organic Synthesis* 2d. Ed., Wiley & Sons, 1991, Ch. 2 (pp. 10-142), Ch. 5 (pp. 224-276), and Ch. 7 (pp. 309-405).

(Continued)

*Primary Examiner*—Kamal A Saeed
*Assistant Examiner*—Samantha L Shterengarts
(74) *Attorney, Agent, or Firm*—Doina G. Ene

(57) ABSTRACT

The present invention is directed to substituted propylamine derivatives of formula I:

or a pharmaceutically acceptable salt thereof, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

38 Claims, 2 Drawing Sheets

OTHER PUBLICATIONS

Higuchi and Stella (eds.), *Prodrugs as Novel Drug Delivery Systems*, American Chemical Society (1975), pp. 1-115 and 196-223.

Hughes, D. L., "The Mitsunobu Reaction," *Org. Reactions*, 1992, 42, 335-634.

Hughes, David L., "Progress in the Mitsunobu Reaction. A Review," *Organic Preparations and Procedures International*, 1996, 28(2), 127-164.

Jacques, J. et al., *Enantiomers, Racemates and Resolutions*, Wiley Interscience, NY (1981) pp. 251-434.

Janowsky, D. S. et al., "Desipramine: an overview," *Journal of Clinical Psychiatry*, 1984, 45(10 Pt 2), 3-9.

Katovich, M. J. et al., "Mechanisms Mediating the Thermal Response to Morphine Withdrawal in Rats," *Proceedings of the Society for Experimental Biology & Medicine*, 1990, 193(2), 129-35.

Krämer, P. et al., "Prevention of Hot Flushes with CPA in the Hormonal Treatment of Prostatic Cancer Results of a Placebo-Controlled Double-Blind Trial," *3rd Int'l Symposium on Recent Advances in Urological Cancer Diagnosis and Treatment—Proceedings*, Paris, France: SCI, 3-7 1992.

Krogsgaard-Larsen, et al., (ed). *Design and Application of Prodrugs, Textbook of Drug Design and Development*, Chapter 5, 113-191, 1991.

Kronenberg, F. et al., "Thermoregulatory Physiology of Menopausal Hot Flashes: A Review," *Can. J. Physiol. Pharmacol.*, 1987, 65, 1312-1324.

Loprinzi, C.L. et al., "Venlafaxine in management of hot flashes in survivors of breast cancer: a randomized controlled trial," *Lancet*, Dec. 16, 2000, 356(9247), 2059-2063.

Mackinnon et al., "α2-Adrenoceptors: more subtypes but fewer functional differences," *TIPS*, 1994, 15, 119-123.

Merchenthaler et al., "The effect of estrogens and antiestrogens in a rat model for hot flush," *Maturitas*, 1998, 30(3), 307-316.

Mitsunobu, O., "The Use of Diethyl Azodicarboxylate and Triphenylphosphine in Synthesis and Transformation of Natural Products," *Synthesis* 1981, 1-28.

Moody, C. J. et al., "Dirhodium(II) tetraacetate catalysed reactions of diazo thioamides: isolation and cycloaddition of anhydro-4-hydroxy-1,3-thiazolium hydroxides (thioisomüchnones), an appraoch to analogues of dehydrogliotoxin," *Org. Biomol. Chem.*, 2003, 1, 2716-2722.

Pacholczyk, T. et al., "Expression cloning of a cocaine-and antidepressant-sensitive human noradrenaline transporter," *Nature*, 1991, 350(6316), 350-4.

Panek, D.U. et al., "Effect of continuous intraventricular estrogen or catechol estrogen treatment on catecholamine turnover in various brain regions," *J. Pharmacol. Exp. Ther.*, 1986, 236(3), 646-652.

Prasad, P.D., et al., "Functional expression of the plasma membrane serotonin transporter but not the vesicular monoamine transporter in human placental trophoblasts and choriocarcinoma cells," *Placenta*, 1996, 17(4), 201-7.

*Remington's Pharmaceutical Sciences*, 17th Ed., Gennaro, A. R. (Ed.), Mack Publsihing Company, Easton, PA (1985) pp. 1409-1677.

Srebnik, M, et. al. "Chiral Synthesis via Organoboranes. 18. Selective Reductions. 43. Diisoponocampheylchloroborane as an Excellent Chiral Reducing Reagent for the Synthesis of Halo Alcohols of High Enantiomeric Purity. A Highly Enantioselective Synthesis of Both Optical Isomers of Tomoxetine, Fluoxetine, and Nisoxetine," *J. Org. Chem.*, 1988, 53, 2916.

Stearns,V. et al., "Paroxetine controlled release in the treatment of menopausal hot flashes," *JAMA*, 2003, 289:2827-2834.

Waldinger et al., "Treatment of hot flushes with mirtazapine: four case reports," *Maturitas*, 2000, 36(3), 165-168.

Widder, et al. (ed.), *Methods in Enzymology*, vol. 112, Academic Press (1985), pp. 309-323.

Wilen, S.H. *Tables of Resolving Agents and Optical Resolutions*, pp. 268-298, E.L. Eliel, Ed., University of Notre Dame Press, Notre Dame, IN 1972.

Wilen, S.H., et al., "Strategies in optical resolutions," *Tetrahedron*, 33, 2725-2736, 1977.

\* cited by examiner

SUBSTITUTED PROPYLAMINE DERIVATIVES AND METHODS OF THEIR USE

CROSS REFERENCE TO RELATED APPLICATIONS

This application claims priority to U.S. Application No. 60/722,052 filed Sep. 29, 2005, the entire disclosure of which is incorporated herein by reference.

FIELD OF THE INVENTION

The present invention relates to substituted propylamine derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

BACKGROUND OF THE INVENTION

Vasomotor symptoms (VMS), referred to as hot flushes and night sweats, are the most common symptoms associated with menopause, occurring in 60% to 80% of all women following natural or surgically-induced menopause. VMS are likely to be an adaptive response of the central nervous system (CNS) to declining sex steroids. To date, the most effective therapies for VMS are hormone-based treatments, including estrogens and/or some progestins. Hormonal treatments are very effective at alleviating VMS, but they are not appropriate for all women. It is well recognized that VMS are caused by fluctuations of sex steroid levels and can be disruptive and disabling in both males and females. A hot flush can last up to thirty minutes and vary in their frequency from several times a week to multiple occurrences per day. The patient experiences a hot flash as a sudden feeling of heat that spreads quickly from the face to the chest and back and then over the rest of the body. It is usually accompanied by outbreaks of profuse sweating. It may sometimes occur several times an hour, and it often occurs at night. Hot flushes and outbreaks of sweats occurring during the night can cause sleep deprivation. Psychological and emotional symptoms observed, such as nervousness, fatigue, irritability, insomnia, depression, memory loss, headache, anxiety, nervousness or inability to concentrate are considered to be caused by the sleep deprivation following hot flush and night sweats (Kramer et al., In: Murphy et al., 3$^{rd}$ Int'l Symposium on Recent Advances in Urological Cancer Diagnosis and Treatment-Proceedings, Paris, France: SCI: 3-7 (1992)).

Hot flushes may be even more severe in-women treated for breast cancer for several reasons: 1) many survivors of breast cancer are given tamoxifen, the most prevalent side effect of which is hot flush, 2) many women treated for breast cancer undergo premature menopause from chemotherapy, 3) women with a history of breast cancer have generally been denied estrogen therapy because of concerns about potential recurrence of breast cancer (Loprinzi, et al., Lancet, 2000, 356(9247): 2059-2063).

Men also experience hot flushes following steroid hormone (androgen) withdrawal. This is true in cases of age-associated androgen decline (Katovich, et al., Proceedings of the Society for Experimental Biology & Medicine, 1990, 193 (2): 129-35) as well as in extreme cases of hormone deprivation associated with treatments for prostate cancer (Berendsen, et al., European Journal of Pharmacology, 2001, 419(1): 47-54. As many as one-third of these patients will experience persistent and frequent symptoms severe enough to cause significant discomfort and inconvenience.

The precise mechanism of these symptoms is unknown but generally is thought to represent disturbances to normal homeostatic mechanisms controlling thermoregulation and vasomotor activity (Kronenberg, et al., "Thermoregulatory Physiology of Menopausal Hot Flashes: A Review," Can. J. Physiol. Pharmacol., 1987, 65:1312-1324).

The fact that estrogen treatment (e.g., estrogen replacement therapy) relieves the symptoms establishes the link between these symptoms and an estrogen deficiency. For example, the menopausal stage of life is associated with a wide range of other acute symptoms as described above and these symptoms are generally estrogen responsive.

It has been suggested that estrogens may stimulate the activity of both the norepinephrine (NE) and/or serotonin (5-HT) systems (J. Pharmacology & Experimental Therapeutics, 1986, 236(3) 646-652). It is hypothesized that estrogens modulate NE and 5-HT levels providing homeostasis in the thermoregulatory center of the hypothalamus. The descending pathways from the hypothalamus via brainstem/ spinal cord and the adrenals to the skin are involved in maintaining normal skin temperature. The action of NE and 5-HT reuptake inhibitors is known to impinge on both the CNS and peripheral nervous system (PNS). The pathophysiology of VMS is mediated by both central and peripheral mechanisms and, therefore, the interplay between the CNS and PNS may account for the efficacy of dual acting SRI/NRIs in the treatment of thermoregulatory dysfunction. In fact, the physiological aspects and the CNS/PNS involvement in VMS may account for the lower doses proposed to treat VMS (Loprinzi, et al., Lancet, 2000, 356:2059-2063; Stearns et al., JAMA, 2003, 289:2827-2834) compared to doses used to treat the behavioral aspects of depression. The interplay of the CNS/ PNS in the pathophysiology of VMS and the presented data within this document were used to support the claims that the norepinephrine system could be targeted to treat VMS.

Although VMS are most commonly treated by hormone therapy (orally, transdermally, or via an implant), some patients cannot tolerate estrogen treatment (Berendsen, Maturitas, 2000, 36(3): 155-164, Fink et al., Nature, 1996, 383(6598): 306). In addition, hormone replacement therapy is usually not recommended for women or men with or at risk for hormonally sensitive cancers (e.g. breast or prostate cancer). Thus, non-hormonal therapies (e.g. fluoxetine, paroxetine [SRIs] and clonidine) are being evaluated clinically. WO9944601 discloses a method for decreasing hot flushes in a human female by administering fluoxetine. Other options have been studied for the treatment of hot flashes, including steroids, alpha-adrenergic agonists, and beta-blockers, with varying degree of success (Waldinger et al., Maturitas, 2000, 36(3): 165-168).

It has been reported that $\alpha_2$-adrenergic receptors play a role in thermoregulatory dysfunctions (Freedman et al., Fertility & Sterility, 2000, 74(1): 20-3). These receptors are located both pre- and post-synaptically and mediate an inhibitory role in the central and peripheral nervous system. There are four distinct subtypes of the adrenergic$_2$ receptors, i.e., are $\alpha_{2A}$, $\alpha_{2B}$, $\alpha_{2C}$ and $\alpha_{2D}$ (Mackinnon et al., TIPS, 1994, 15: 119; French, Pharmacol Ther., 1995, 68: 175). It has been reported that a non-select $\alpha_2$-adrenoceptor antagonist, yohimbine, induces a flush and an $\alpha_2$-adrenergic receptor agonist, clonidine, alleviates the yohimbine effect (Katovich, et al, *Proceedings of the Society for Experimental Biology & Medicine,* 1990, 193(2): 129-35, Freedman et al, *Fertility & Sterility,* 2000, 74(1): 20-3). Clonidine has been used to treat hot flush. However, using such treatment is associated with a number of undesired side effects caused by high doses necessary to abate hot flash described herein and known in the related arts.

Given the complex multifaceted nature of thermoregulation and the interplay between the CNS and PNS in maintaining thermoregulatory homeostasis, multiple therapies and approaches can be developed to target vasomotor symptoms. The present invention focuses on novel compounds and compositions containing these compounds directed to these and other important uses.

SUMMARY OF THE INVENTION

The present invention is directed to substituted propylamine derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In one embodiment, the invention is directed to compounds of formula I:

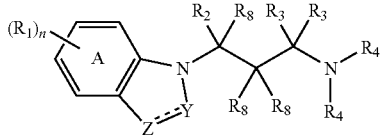

or a pharmaceutically acceptable salt thereof;
wherein:
the dotted line between Y and Z represents an optional second bond;
Y is $CR_3$, $C(R_3)_2$, C=O, or C=N—C=N;
Z is S, O, $NR_6$, $CR_5$ or $C(R_5)_2$;
n is an integer from 0 to 4;
$R_1$ is, independently at each occurrence, alkyl, alkoxy, halo, $CF_3$, $OCF_3$, arylalkyloxy substituted with 0 to 3 $R_7$, aryloxy substituted with 0 to 3 $R_7$, aryl substituted with 0 to 3 $R_7$, heteroaryl substituted with 0 to 3 $R_7$, hydroxy, alkanoyloxy, nitro, cyano, alkenyl, alkynyl, alkylsulfoxide, phenylsulfoxide substituted with 0 to 3 $R_7$, alkylsulfone, phenylsulfone substituted with 0 to 3 $R_7$, alkylsulfonamide, phenylsulfonamide substituted with 0 to 3 $R_7$, heteroaryloxy substituted with 0 to 3 $R_7$, heteroarylmethyloxy substituted with 0 to 3 $R_7$, alkylamido, or arylamido substituted with 0 to 3 $R_7$;
$R_2$ is aryl substituted with 0 to 3 $R_1$, or heteroaryl substituted with 0 to 3 $R_1$;
$R_3$ is, independently at each occurrence, H or $C_1$ to $C_4$ alkyl;
$R_4$ is, independently at each occurrence, H, $C_1$ to $C_4$ alkyl, arylalkyl, heteroarylmethyl, cycloheptylmethyl, cyclohexylmethyl, cyclopentylmethyl, or cyclobutylmethyl, or $R_5$ is, independently, H, $C_1$ to $C_4$ alkyl, $C_3$ to $C_6$ branched alkyl, $C_3$ to $C_6$ cycloalkyl, aryl substituted with 0 to 3 $R_1$; or heteroaryl substituted with 0 to 3 $R_1$; or two $R_5$, together with the carbon through which they are attached, form a carbocyclic ring of 3 to 7 carbons;
$R_6$ is H, $C_1$ to $C_6$ alkyl, $C_3$ to $C_6$ branched alkyl, $C_3$ to $C_6$ cycloalkyl, aryl substituted with 0 to 3 $R_1$, or heteroaryl substituted with 0 to 3 $R_1$;
$R_7$ is, independently at each occurrence, alkyl, alkoxy, halo, $CF_3$, $OCF_3$, hydroxy, alkanoyloxy, nitro, cyano, alkenyl, alkynyl, alkylsulfoxide, alkylsulfone, alkylsulfonamide, or alkylamido;
$R_8$ is, independently at each occurrence, H, F, $C_1$ to $C_6$ alkyl, $C_3$ to $C_6$ branched alkyl, or $C_3$ to $C_6$ cycloalkyl; and
wherein 1 to 3 carbon atoms in ring A may optionally be replaced with N.

In yet other embodiments, the present invention is directed to compositions, comprising:
a. at least one compound according to claim 1 or a pharmaceutically acceptable salt thereof; and
b. at least one pharmaceutically acceptable carrier.

In another embodiment, the present invention is directed to methods for treating or preventing a condition ameliorated by monoamine reuptake in a subject in need thereof, comprising the step of:
administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In another embodiment, the present invention is directed to methods for treating or preventing vasomotor symptoms in a subject in need thereof, comprising the step of:
administering to said subject an effective amount of at least one compound of formula I or pharmaceutically acceptable salt thereof.

In yet another embodiment, the present invention is directed to methods for treating or preventing a depression disorder in a subject in need thereof, comprising the step of:
administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:
administering to said subject an effective amount of at least one compound of formula I or pharmaceutically acceptable salt thereof.

In further embodiments, the present invention is directed to methods for treating or preventing pain in a subject in need thereof, comprising the step of:
administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:

administering to said subject an effective amount of at least one compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of at least one compound of formula I or pharmaceutically acceptable salt thereof.

In another embodiment, the present invention is directed to methods for treating or preventing fibromylagia syndrome in a subject in need thereof, comprising the step of:

administering to said subject an effective amount of at least one compound of formula I or pharmaceutically acceptable salt thereof.

BRIEF DESCRIPTION OF THE DRAWINGS

The invention can be more fully understood from the following detailed description and the accompanying drawings that form a part of this application.

DETAILED DESCRIPTION OF THE INVENTION

Figure 1:
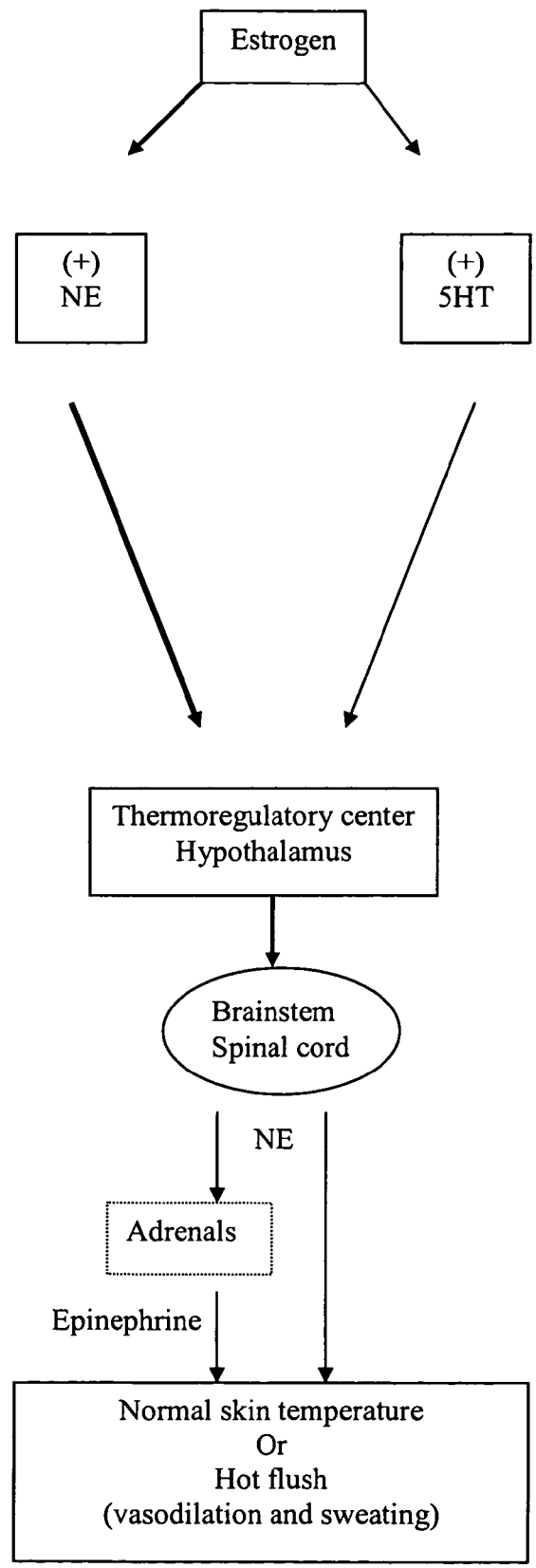
FIG. 1 is an overview of estrogen action on norepinephrine/serotonin mediated thermoregulation.

The present invention is directed to substituted propylamine derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "µL" means microliter(s), "mL" means milliliter(s), "mM" means millimolar, "M" means molar, "mmole" means millimole(s), "cm" means centimeters, "SEM" means standard error of the mean and "IU" means International Units. "Δ° C." and Δ "$ED_{50}$ value" means dose which results in 50% alleviation of the observed condition or effect (50% mean maximum endpoint).

"Norepinephrine transporter" is abbreviated NET.

"Human norepinephrine transporter" is abbreviated hNET.

"Serotonin transporter" is abbreviated SERT.

"Human serotonin transporter" is abbreviated hSERT.

"Norepinephrine reuptake inhibitor" is abbreviated NRI.

"Selective norepinephrine reuptake inhibitor" is abbreviated SNRI.

"Serotonin reuptake inhibitor" is abbreviated SRI.

"Selective serotonin reuptake inhibitor" is abbreviated SSRI.

"Norepinephrine" is abbreviated NE.

"Serotonin is abbreviated 5-HT.

"Subcutaneous" is abbreviated sc.

"Intraperitoneal" is abbreviated ip.

"Oral" is abbreviated po.

In the context of this disclosure, a number of terms shall be utilized. The term "treatment" as used herein includes preventative (e.g., prophylactic), curative or palliative treatment and "treating" as used herein also includes preventative, curative and palliative treatment.

The term "effective amount," as used herein, refers to an amount effective, at dosages, and for periods of time necessary, to achieve the desired result with respect to prevention or treatment of vasomotor symptoms, depression disorders, sexual dysfunction, or pain. In particular, with respect to vasomotor symptoms, "effective amount" refers to the amount of compound or composition of compounds that would increase norepinephrine levels to compensate in part or total for the lack of steroid availability in subjects subject afflicted with a vasomotor symptom. Varying hormone levels will influence the amount of compound required in the present invention. For example, the pre-menopausal state may require a lower level of compound due to higher hormone levels than the peri-menopausal state.

It will be appreciated that the effective amount of components of the present invention will vary from patient to patient not only with the particular compound, component or composition selected, the route of administration, and the ability of the components (alone or in combination with one or more combination drugs) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects.

Preferably, the compounds of the present invention are administered at a dosage and for a time such that the number of hot flushes is reduced as compared to the number of hot flushes prior to the start of treatment. Such treatment can also be beneficial to reduce the overall severity or intensity distribution of any hot flushes still experienced, as compared to the severity of hot flushes prior to the start of the treatment. With respect to depression disorders, sexual dysfunction, and pain, the compounds of the present invention are administered at a dosage and for a time such that there is the prevention, alleviation, or elimination of the symptom or condition.

For example, for an afflicted patient, compounds of formula I, or a pharmaceutically acceptable salt thereof, may be administered, preferably, at a dosage of from about 0.1 mg/day to about 500 mg/day, dosed one or two times daily, more preferably from about 1 mg/day to about 200 mg/day and most preferably from about 1 mg/day to 100 mg/day for a time sufficient to reduce and/or substantially eliminate the number and/or severity of hot flushes or symptom or condition of the depression disorder, sexual dysfunction, or pain.

The terms "component," "composition of compounds," "compound," "drug," or "pharmacologically active agent" or "active agent" or "medicament" are used interchangeably herein to refer to a compound or compounds or composition of matter which, when administered to a subject (human or animal) induces a desired pharmacological and/or physiologic effect by local and/or systemic action.

As used herein, the term "inhibitor" refers to any agent that inhibits, suppresses, represses, or decreases a specific activity, such as serotonin reuptake activity or the norepinephrine reuptake activity, e.g., antibody, small molecule, peptide, oligopeptide, polypeptide, or protein, preferably small molecule or peptide, that exhibits a partial, complete, competitive and/or inhibitory effect on mammalian, preferably the human norepinephrine reuptake or both serotonin reuptake and the norepinephrine reuptake, thus diminishing or blocking, preferably diminishing, some or all of the biological effects of endogenous norepinephrine reuptake or of both serotonin reuptake and the norepinephrine reuptake.

Within the present invention, the compounds of formula I may be prepared in the form of pharmaceutically acceptable salts. As used herein, the term "pharmaceutically acceptable salts" refers to salts prepared from pharmaceutically acceptable non-toxic acids, including inorganic salts, and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferably is the hydrochloride salt.

"Administering," as used herein, means either directly administering a compound or composition of the present invention, or administering a prodrug, derivative or analog which will form an equivalent amount of the active compound or substance within the body.

The term "subject" or "patient" refers to an animal including the human species that is treatable with the compositions, and/or methods of the present invention. The term "subject" or "subjects" is intended to refer to both the male and female gender unless one gender is specifically indicated. Accordingly, the term "patient" comprises any mammal which may benefit from treatment or prevention of vasomotor symptoms, depression disorders, sexual dysfunction, or pain, such as a human, especially if the mammal is female, either in the pre-menopausal, peri-menopausal, or post-menopausal period. Furthermore, the term patient includes female animals including humans and, among humans, not only women of advanced age who have passed through menopause but also women who have undergone hysterectomy or for some other reason have suppressed estrogen production, such as those who have undergone long-term administration of corticosteroids, suffer from Cushing's syndrome or have gonadal dysgenesis. However, the term "patient" is not intended to be limited to a woman.

The terms "premature menopause" or "artificial menopause" refer to ovarian failure of unknown cause that may occur before age 40. It may be associated with smoking, living at high altitude, or poor nutritional status. Artificial menopause may result from oophorectomy, chemotherapy, radiation of the pelvis, or any process that impairs ovarian blood supply.

The term "pre-menopausal" means before the menopause, the term "peri-menopausal" means during the menopause and the term "post-menopausal" means after the menopause.

"Ovariectomy" means removal of an ovary or ovaries and can be effected according to Merchenthaler et al., *Maturitas*, 1998, 30(3): 307-316.

The term "side effect" refers to a consequence other than the one(s) for which an agent or measure is used, as the adverse effects produced by a drug, especially on a tissue or organ system other then the one sought to be benefited by its administration. In the case, for example, of high doses of NRIs or NRI/SRI compounds alone, the term "side effect" may refer to such conditions as, for example, vomiting, nausea, sweating, and flushes (Janowsky, et al., *Journal of Clinical Psychiatry,* 1984, 45(10 Pt 2): 3-9).

"Alkyl," as used herein, refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms being preferred, and with from about 1 to about 4 carbon atoms, herein referred to as "lower alkyl", being more preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

"Heteroalkyl," as used herein, refers to a substituent of the general formula (alkyl-X)$_n$-alkyl-, where each "alkyl" is independently as defined above, "X" is a sulfur, oxygen, or N heteroatom-containing moiety, and n is 1-4, preferably one. Heteroalkyl groups include, but are not limited to, methoxymethyl, ethoxyethyl, methoxyethyl, methylsulfanylmethyl, ethylsulfanylethyl, methylsulfanylethyl, methylaminoethyl, ethylaminoethyl, and methylaminoethyl.

"Alkenyl," as used herein, refers to an alkyl group of at least two carbon atoms having one or more double bonds, wherein alkyl is as defined herein. Alkenyl groups can be optionally substituted.

"Alkynyl," as used herein, refers to an alkyl group of at least two carbon atoms having one or more triple bonds, wherein alkyl is as defined herein. Alkynyl groups can be optionally substituted.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl. ;

"Heteroaryl," as used herein, refers to an optionally substituted, mono-, di-, tri-, or other multicyclic aromatic ring system that includes at least one, and preferably from 1 to about 4 heteroatom ring members selected from sulfur, oxygen and nitrogen. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

"Heterocyclic ring," as used herein, refers to a stable 5- to 7-membered monocyclic or bicyclic or 7- to 10-membered bicyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1 H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1 H-indazolyl, oxazolidinyl, benzotriazolyl, benzisoxazolyl, oxindolyl, benzoxazolinyl, or isatinyl. Also included are fused ring and spiro compounds containing, for example, the above heterocycles.

"Alkoxy," as used herein, refers to the group R—O— where R is an alkyl group as defined herein.

"Aryloxy," as used herein, refers to the group R—O— where R is an aryl group, as defined herein.

"Heteroaryloxy," as used herein, refers to the group R—O— where R is a heteroaryl group, as defined herein.

"Heteroarylmethyl" as used herein, refers to the group R—CH$_2$— where R is a heteroaryl group, as defined herein.

"Heteroarylmethoxy," as used herein, refers to the group R—CH$_2$—O— where R is a heteroaryl group, as defined herein.

"Arylalkoxy," as used herein, refers to the group R$_z$—R$_x$—O— where R$_z$ is an aryl group and R$_x$ is an alkyl group, as defined herein.

"Alkanoyloxy," as used herein, refers to the group R—C(=O)—O— where R is an alkyl group of 1 to 5 carbon atoms.

"Arylalkyl" as used herein, refers to the group R$_z$—R$_y$— where R$_z$ is an aryl group, as defined herein, and where R$_y$ is an alkyl group, as defined herein.

"Alkylsulfoxide," as used herein, refers to as used herein, refers to —S(=O)—R, where R is alkyl, as defined above.

"Alkylsulfone," as used herein, refers to —S(=O)$_2$—R, where R is alkyl, as defined above.

"Arylsulfoxide," as used herein, refers to as used herein, refers to —S(=O)—R, where R is aryl, as defined above.

"Arylsulfone," as used herein, refers to —S(=O)$_2$—R, where R is aryl, as defined above.

"Alkylsulfonamide," as used herein, refers to —NR—S(=O)$_2$—R, where each R is independently, alkyl, as defined above or the NR part may also be NH.

"Arylsulfonamide," as used herein, refers to —NR—S(=O)$_2$—R, where each R is independently, aryl, as defined above or the NR part may also be NH (provided that the other R is aryl).

"Heteroarylmethoxy," as used herein, refers to —OCH$_2$—R, where R is heteroaryl, as defined above.

"Alkylamido," as used herein, refers to —NR—C(=O)—R, where each R is independently, alkyl, as defined above, or the NR part may also be NH.

"Arylamido," as used herein, refers to —NR$_y$—C(=O)—R$_z$, where R$_y$ and R$_z$ are H or aryl (provided that at least one of R$_y$ and R$_z$ is aryl), as defined above.

"Halo," as used herein, refers to chloro, bromo, fluoro, and iodo.

When any variable occurs more than one time in any constituent or any formula, its definition in each occurrence is independent of its definition at every other occurrence. Combinations of substituents and/or variables and/or replacements atoms or groups are permissible only if such combinations result in a stable compound.

In one embodiment, the invention is directed to compounds of formula I:

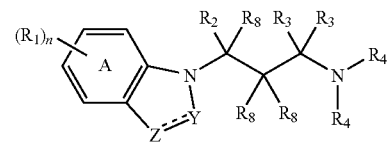

or a pharmaceutically acceptable salt thereof;

wherein:

the dotted line between Y and Z represents an optional second bond;

Y is CR$_3$, C(R$_3$)$_2$, C=O, or C=N—C=N;

Z is S, O, NR$_6$, CR$_5$ or C(R$_5$)$_2$;

n is an integer from 0 to 4;

R$_1$ is, independently at each occurrence, alkyl, alkoxy, halo, CF$_3$, OCF$_3$, arylalkyloxy substituted with 0 to 3 R$_7$, aryloxy substituted with 0 to 3 R$_7$, aryl substituted with 0 to 3 R$_7$, heteroaryl substituted with 0 to 3 R$_7$, hydroxy, alkanoyloxy, nitro, cyano, alkenyl, alkynyl, alkylsulfoxide, phenylsulfoxide substituted with 0 to 3 R$_7$, alkylsulfone, phenylsulfone substituted with 0 to 3 R$_7$, alkylsulfonamide, phenylsulfonamide substituted with 0 to 3 R$_7$, heteroaryloxy substituted with 0 to 3 R$_7$, heteroarylmethyloxy substituted with 0 to 3 R$_7$, alkylamido, or arylamido substituted with 0 to 3 R$_7$;

$R_2$ is aryl substituted with 0 to 3 $R_1$, or heteroaryl substituted with 0 to 3 $R_1$;

$R_3$ is, independently at each occurrence, H or $C_1$ to $C_4$ alkyl;

$R_4$ is, independently at each occurrence, H, $C_1$ to $C_4$ alkyl, arylalkyl, heteroarylmethyl, cycloheptylmethyl, cyclohexylmethyl, cyclopentylmethyl, or cyclobutylmethyl, or $R_5$ is, independently, H, $C_1$ to $C_4$ alkyl, $C_3$ to $C_6$ branched alkyl, $C_3$ to $C_6$ cycloalkyl, aryl substituted with 0 to 3 $R_1$; or heteroaryl substituted with 0 to 3 $R_1$; or two $R_5$, together with the carbon through which they are attached, form a carbocyclic ring of 3 to 7 carbons;

$R_6$ is H, $C_1$ to $C_6$ alkyl, $C_3$ to $C_6$ branched alkyl, $C_3$ to $C_6$ cycloalkyl, aryl substituted with 0 to 3 $R_1$, or heteroaryl substituted with 0 to 3 $R_1$;

$R_7$ is, independently at each occurrence, alkyl, alkoxy, halo, $CF_3$, $OCF_3$, hydroxy, alkanoyloxy, nitro, cyano, alkenyl, alkynyl, alkylsulfoxide, alkylsulfone, alkylsulfonamide, or alkylamido;

$R_8$ is, independently at each occurrence, H, F, $C_1$ to $C_6$ alkyl, $C_3$ to $C_6$ branched alkyl, or $C_3$ to $C_6$ cycloalkyl; and wherein 1 to 3 carbon atoms in ring A may optionally be replaced with N.

In certain preferred embodiments, the compounds of formula I are of the following formulae:

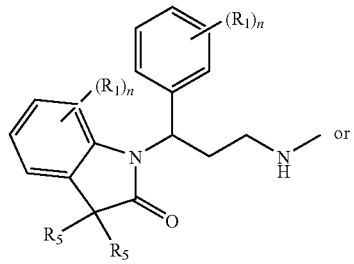

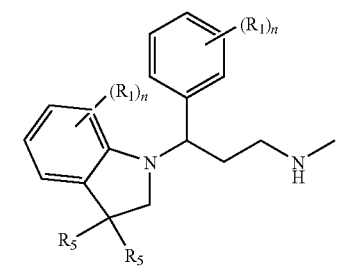

or a pharmaceutically acceptable salt thereof;
wherein:

$R_1$ is, independently at each occurrence, H, halo, hydroxyl, cyano, alkoxy, or $C_1$ to $C_6$ alkyl;

$R_5$ is, independently at each occurrence, $C_1$ to $C_6$ alkyl; or two $R_5$, together with the carbon through which they are attached, form a carbocyclic ring of 3 to 7 carbons; and n is 0 or 1.

In certain preferred embodiments, the compounds of formula I are of the following formula:

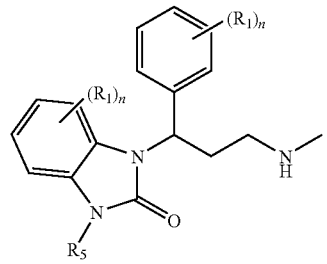

or a pharmaceutically acceptable salt thereof;
wherein:

$R_1$ is, independently at each occurrence, H, halo, hydroxyl, cyano, alkoxy, or $C_1$ to $C_6$ alkyl;

$R_5$ is $C_1$ to $C_4$ alkyl, $C_3$ to $C_6$ branched alkyl, $C_3$ to $C_6$ cycloalkyl, or aryl substituted with 0 to 3 $R_1$; and n is 0 or 1.

In certain preferred embodiments of the compounds of formula I, the dotted line between Y and Z represents a second bond.

In certain preferred embodiments of the compounds of formula I, Y is $C(R_3)_2$, C=O, or C=N—C≡N, especially Y is $CH_2$, C=O, or C=N—C≡N.

In certain preferred embodiments of the compounds of formula I, Z is $NR_6$, $CR_5$ or $C(R_5)_2$.

In certain preferred embodiments of the compounds of formula I, n is an integer from 0 to 3, especially 0 to 2, more especially 0 or 1.

In certain preferred embodiments of the compounds of formula I, $R_1$ is, independently at each occurrence, alkyl, alkoxy, halo, $CF_3$, $OCF_3$, aryl substituted with 0 to 3 $R_7$, heteroaryl substituted with 0 to 3 $R_7$, hydroxy, alkanoyloxy, nitro, or cyano, especially alkyl or halo, more especially, halo, and, even more especially, fluoro.

In certain preferred embodiments of the compounds of formula I, $R_2$ is aryl substituted with 0 to 3 $R_1$, especially, phenyl or halo-substituted aryl, more especially phenyl, fluoro-substituted aryl, difluoro-substituted aryl, or fluoro, chloro-substituted aryl.

In certain preferred embodiments of the compounds of formula I, $R_2$ is heteroaryl substituted with 0 to 3 $R_1$.

In certain preferred embodiments of the compounds of formula I, $R_3$ is, independently at each occurrence, H or $C_1$ to $C_2$ alkyl, especially H.

In certain preferred embodiments of the compounds of formula I, $R_4$ is, independently at each occurrence, H, $C_1$ to $C_4$ alkyl, arylalkyl, heteroarylmethyl, cycloheptylmethyl, cyclohexylmethyl, cyclopentylmethyl, or cyclobutylmethyl, especially H or $C_1$ to $C_4$ alkyl, more especially H, methyl, or ethyl. In certain preferred embodiments of the compounds of formula I, both $R_4$ are H. In certain preferred embodiments of the compounds of formula I, both $R_4$ are methyl. In certain preferred embodiments of the compounds of formula I, one $R_4$ is H and the other $R_4$ is methyl or ethyl.

In certain preferred embodiments of the compounds of formula I, both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$ to $C_4$ alkyl, F, or $CF_3$.

In certain preferred embodiments of the compounds of formula I, $R_5$ is, independently, H, $C_1$ to $C_4$ alkyl, $C_3$ to $C_6$ branched alkyl, $C_3$ to $C_6$ cycloalkyl, aryl substituted with 0 to 3 $R_1$; or heteroaryl substituted with 0 to 3 $R_1$, especially H or $C_1$ to $C_4$ alkyl, more especially H or methyl.

In certain preferred embodiments of the compounds of formula I, two $R_5$, together with the carbon through which they are attached, form a carbocyclic ring of 3 to 7 carbons;

In certain preferred embodiments of the compounds of formula I, $R_6$ is H, $C_1$ to $C_6$ alkyl, $C_3$ to $C_6$ branched alkyl, $C_3$ to $C_6$ cycloalkyl, aryl, or heteroaryl, especially $R_6$ is H, $C_1$ to $C_4$ alkyl, $C_3$ to $C_6$ branched alkyl, $C_3$ to $C_6$ cycloalkyl, aryl, or heteroaryl, more especially $R_6$ is H, methyl, ethyl, n-propyl, isopropyl, cyclopropyl, cyclopentyl, cyclohexyl, or phenyl.

In certain preferred embodiments of the compounds of formula I, $R_7$ is, independently at each occurrence, alkyl, alkoxy, halo, $CF_3$, $OCF_3$, hydroxy, alkanoyloxy, nitro, or cyano.

In certain preferred embodiments of the compounds of formula I, $R_8$ is, independently at each occurrence, H, F, and $C_1$ to $C_6$ alkyl, especially H.

In certain preferred embodiments of the compounds of formula I, 1 to 3 carbon atoms in ring A may optionally be replaced with N;

In certain preferred embodiments of the compounds of formula I, the dotted line between the two $R_4$ groups represents an optional heterocyclic ring of 4 to 6 ring atoms that may be formed between the two $R_4$ groups, together with the nitrogen through which they are attached.

Particularly preferred embodiments of the compounds of formula I, include, but are not limited to:

1'-[3-(methylamino)-1-phenylpropyl]spiro[cyclohexane-1,3'-indol]-2'(1'H)-one;

1'-[1-(3-fluorophenyl)-3-(methylamino)propyl]spiro[cyclohexane-1,3'-indol]-2'(1'H)-one;

7-fluoro-1-[1-(3-fluorophenyl)-3-(methylamino)propyl]-3,3-dimethyl-1,3-dihydro-2H-indol-2-one;

3,3-dimethyl-1-[3-(methylamino)-1-phenylpropyl]-1,3-dihydro-2H-indol-2-one;

7-fluoro-3,3-dimethyl-1-[3-(methylamino)-1-phenylpropyl]-1,3-dihydro-2H-indol-2-one;

3-(3,3-dimethyl-2,3-dihydro-1H-indol-1-yl)-N-methyl-3-phenylpropan-1-amine;

3-(7-fluoro-3,3-dimethyl-2,3-dihydro-1H-indol-1-yl)-N-methyl-3-phenylpropan-1-amine;

1-ethyl-3-[3-(methylamino)-1-phenylpropyl]-1,3-dihydro-2H-benzimidazol-2-one;

1-cyclopropyl-3-[3-(methylamino)-1-phenylpropyl]-1,3-dihydro-2H-benzimidazol-2-one;

1-isopropyl-3-[3-(methylamino)-1-phenylpropyl]-1,3-dihydro-2H-benzimidazol-2-one;

1-[3-(methylamino)-1-phenylpropyl]-3-propyl-1,3-dihydro-2H-benzimidazol-2-one;

1-methyl-3-[3-(methylamino)-1-phenylpropyl]-1,3-dihydro-2H-benzimidazol-2-one;

1-cyclopentyl-3-[3-(methylamino)-1-phenylpropyl]-1,3-dihydro-2H-benzimidazol-2-one;

1-cyclohexyl-3-[3-(methylamino)-1-phenylpropyl]-1,3-dihydro-2H-benzimidazol-2-one;

3-[3-(methylamino)-1-phenylpropyl]-1,3-benzothiazol-2(3H)-one;

1-isopropyl-3-[3-(methylamino)-1-phenylpropyl]-1,3-dihydro-2H-benzimidazol-2-ylidene}cyanamide;

1-[3-amino-1-phenylpropyl]-3-ethyl-1,3-dihydro-2H-benzimidazol-2-one;

1-ethyl-3-[3-(ethylamino)-1-phenylpropyl]-1,3-dihydro-2H-benzimidazol-2-one;

1-[3-(dimethylamino)-1-phenylpropyl]-3-ethyl-1,3-dihydro-2H-benzimidazol-2-one;

4-fluoro-1-isopropyl-3-[3-(methylamino)-1-phenylpropyl]-1,3-dihydro-2H-benzimidazol-2-one;

3-[3-(dimethylamino)-1-phenylpropyl]4-fluoro-1-isopropyl-1,3-dihydro-2H-benzimidazol-2-one;

{(2Z)-3-[3-(dimethylamino)-1-phenylpropyl]-5-fluoro-1-propyl-1,3-dihydro-2H-benzimidazol-2-ylidene}cyanamide;

3-(7-fluoro-3,3-dimethyl-2,3-dihydro-1H-indol-1-yl)-3-(3-fluorophenyl)-N-methylpropan-1-amine;

1-[1-(3-chloro-5-fluorophenyl)-3-(methylamino)propyl]-7-fluoro-3,3-dimethyl-1,3-dihydro-2H-indol-2-one;

1-[1-(3,5-difluorophenyl)-3-(methylamino)propyl]-7-fluoro-3,3-dimethyl-1,3-dihydro-2H-indol-2-one;

1-[1-(3-chlorophenyl)-3-(methylamino)propyl]-7-fluoro-3,3-dimethyl-1,3-dihydro-2H-indol-2-one;

4-fluoro-1-(2-fluorophenyl)-3-[3-(methylamino)-1-phenylpropyl]-1,3-dihydro-2H-benzimidazol-2-one;

1-ethyl-4-fluoro-3-[1-(3-fluorophenyl)-3-(methylamino)propyl]-1,3-dihydro-2H-benzimidazol-2-one; or a pharmaceutically acceptable salt thereof.

Even more preferred embodiments of the compounds of formula I, include, but are not limited to:

1'-[(1R)-3-(methylamino)-1-phenylpropyl]spiro[cyclohexane-1,3'-indol]-2'(1'H)-one;

1'-[(1S)-3-(methylamino)-1-phenylpropyl]spiro[cyclohexane-1,3'-indol]-2'(1'H)-one;

1'-[(1R)-1-(3-fluorophenyl)-3-(methylamino)propyl]spiro[cyclohexane-1,3'-indol]-2'(1'H)-one;

1'-[(1S)-1-(3-fluorophenyl)-3-(methylamino)propyl]spiro[cyclohexane-1,3'-indol]-2'(1'H)-one;

7-fluoro-1-[(1R)-1-(3-fluorophenyl)-3-(methylamino)propyl]-3,3-dimethyl-1,3-dihydro-2H-indol-2-one;

7-fluoro-1-[(1S)-1-(3-fluorophenyl)-3-(methylamino)propyl]-3,3-dimethyl-1,3-dihydro-2H-indol-2-one;

3,3-dimethyl-1-[(1S)-3-(methylamino)i1-phenylpropyl]-1,3-dihydro-2H-indol-2-one;

3,3-dimethyl-1-[(1R)-3-(methylamino)i1-phenylpropyl]-1,3-dihydro-2H-indol-2-one;

3,3-dimethyl-1-[(1R)-3-(methylamino)-1-phenylpropyl]-1,3-dihydro-2H-indol-2-one;

3,3-dimethyl-1-[(1S)-3-(methylamino)-1-phenylpropyl]-1,3-dihydro-2H-indol-2-one;

7-fluoro-3,3-dimethyl-1-[(1R)-3-(methylamino)-1-phenylpropyl]-1,3-dihydro-2H-indol-2-one;

(3R)-3-(3,3-dimethyl-2,3-dihydro-1H-indol-1-yl)-N-methyl-3-phenylpropan-1-amine;

(3R)-3-(7-fluoro-3,3-dimethyl-2,3-dihydro-1H-indol-1-yl)-N-methyl-3-phenylpropan-1-amine;

1-ethyl-3-[(1R)-3-(methylamino)-1-phenylpropyl]-1,3-dihydro-2H-benzimidazol-2-one;

1-cyclopropyl-3-[(1S)-3-(methylamino)-1-phenylpropyl]-1,3-dihydro-2H-benzimidazol-2-one;

1-cyclopropyl-3-[(1R)-3-(methylamino)-1-phenylpropyl]-1,3-dihydro-2H-benzimidazol-2-one;

1-isopropyl-3-[(1S)-3-(methylamino)-1-phenylpropyl]-1,3-dihydro-2H-benzimidazol-2-one;

1-isopropyl-3-[(1R)-3-(methylamino)-1-phenylpropyl]-1,3-dihydro-2H-benzimidazol-2-one;

1-[(1S)-3-(methylamino)-1-phenylpropyl]-3-propyl-1,3-dihydro-2H-benzimidazol-2-one;

1-[(1R)-3-(methylamino)-1-phenylpropyl]-3-propyl-1,3-dihydro-2H-benzimidazol-2-one;

1-[(1S)-3-(methylamino)-1-phenylpropyl]-3-phenyl-1,3-dihydro-2H-benzimidazol-2-one;

1-[(1R)-3-(methylamino)-1-phenylpropyl]-3-phenyl-1,3-dihydro-2H-benzimidazol-2-one;

1-methyl-3-[(1R)-3-(methylamino)-1-phenylpropyl]-1,3-dihydro-2H-benzimidazol-2-one;

1-cyclopentyl-3-[(1R)-3-(methylamino)-1-phenylpropyl]-1,3-dihydro-2H-benzimidazol-2-one;

1-cyclohexyl-3-[(1R)-3-(methylamino)-1-phenylpropyl]-1,3-dihydro-2H-benzimidazol-2-one;

3-[(1R)-3-(methylamino)-1-phenylpropyl]-1,3-benzothiazol-2(3H)-one;

1-isopropyl-3-[(1R)-3-(methylamino)-1-phenylpropyl]-1,3-dihydro-2H-benzimidazol-2-ylidene}cyanamide;

1-[(1R)-3-amino-1-phenylpropyl]-3-ethyl-1,3-dihydro-2H-benz-imidazol-2-one;

1-ethyl-3-[(1R)-3-(ethylamino)-1-phenylpropyl]-1,3-dihydro-2H-benzimidazol-2-one;

1-[(1R)-3-(dimethylamino)-1-phenylpropyl]-3-ethyl-1,3-dihydro-2H-benzimidazol-2-one;

4-fluoro-1-isopropyl-3-[(1S)-3-(methylamino)-1-phenylpropyl]-1,3-dihydro-2H-benzimidazol-2-one;

4-fluoro-1-isopropyl-3-[(1R)-3-(methylamino)-1-phenylpropyl]-1,3-dihydro-2H-benzimidazol-2-one;

3-[(1R)-3-(dimethylamino)-1-phenylpropyl]4-fluoro-1-isopropyl-1,3-dihydro-2H-benzimidazol-2-one;

{(2Z)-3-[(1R)-3-(dimethylamino)-1-phenylpropyl]-5-fluoro-1-propyl-1,3-dihydro-2H-benzimidazol-2-ylidene}cyanamide; or a pharmaceutically acceptable salt thereof.

Some of the compounds of the present invention may contain chiral centers and such compounds may exist in the form of stereoisomers (i.e. enantiomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron*, 33:2725 (1977); Eliel, E. L. *Stereochemistry of Carbon Compounds*, (McGraw-Hill, NY, 1962); Wilen, S. H. *Tables of Resolving Agents and Optical Resolutions*, p. 268 (E. L. Eliel, Ed., University of Notre Dame Press, Notre Dame, Ind. 1972).

The present invention includes prodrugs of the compounds of formula I. "Prodrug," as used herein, means a compound which is convertible in vivo by metabolic means (e.g. by hydrolysis) to a compound of formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs," *Textbook of Drug Design and Development*, Chapter 5, 113-191 (1991), Bundgaard, et al., *Journal of Drug Deliver Reviews*, 1992, 8:1-38, Bundgaard, *J. of Pharmaceutical Sciences*, 1988, 77:285 et seq.; and Higuchi and Stella (eds.) *Prodrugs as Novel Drug Delivery Systems*, American Chemical Society (1975).

Further, the compounds of formula I may exist in unsolvated as well as in solvated forms with pharmaceutically acceptable solvents such as water, ethanol, and the like. In general, the solvated forms are considered equivalent to the unsolvated forms for the purpose of the present invention.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

Compounds of the present invention are suitably prepared in accordance with the following general description and specific examples. Variables used are as defined for formula I, unless otherwise noted. The reagents used in the preparation of the compounds of this invention can be either commercially obtained or can be prepared by standard procedures described in the literature.

The compounds of this invention contain chiral centers, providing various stereoisomeric forms such as enantiomeric mixtures as well as optical isomers. The individual optical isomers can be prepared directly through asymmetric and/or stereospecific synthesis or by conventional chiral separation of optical isomers from the enantiomeric mixture.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale. Compounds of the present invention are suitably prepared in accordance with the following general description and specific examples. Variables used are as defined for formula I, unless otherwise noted. The reagents used in the preparation of the compounds of this invention can be either commercially obtained or can be prepared by standard procedures described in the literature.

The compounds of this invention contain chiral centers, providing various stereoisomeric forms such as enantiomeric mixtures as well as optical isomers. The individual optical isomers can be prepared directly through asymmetric and/or stereospecific synthesis or by conventional chiral separation of optical isomers from the enantiomeric mixture.

As will be readily understood, functional groups present may contain protecting groups during the course of synthesis. Protecting groups are known per se as chemical functional groups that can be selectively appended to and removed from functionalities, such as hydroxyl groups and carboxyl groups.

These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

In accordance with this invention, compounds of formula I are produced by the following reaction schemes (Schemes 1 to 3). Depending on the desired heterocycle or stereochemistry to be incorporated into the compounds, one or more than one of these synthetic routes may be used.

hydroxyl protecting groups (See, for example, Greene, T. W.; Wuts, P. G. *Protecting Groups in Organic Synthesis*, Second Edition, 1991, John Wiley & Sons, Inc., the entire disclosure which is incorporated by reference). Conversion of the hydroxyl group in 5 to a suitable leaving group, such as a tosylate by reaction with toluenesulfonylchloride and pyridine, and displacement with an amine of formula $NH(R_4)_2$ will provide the desired compounds of structure 6. Those skilled in the art will appreciate that there are a variety of methods for converting alcohols to leaving groups that can be readily displaced by an amine. Common leaving groups such as tosylate, triflate, mesylate, iodide, bromide, chloride are prepared from alcohols by a variety of reagent combinations.

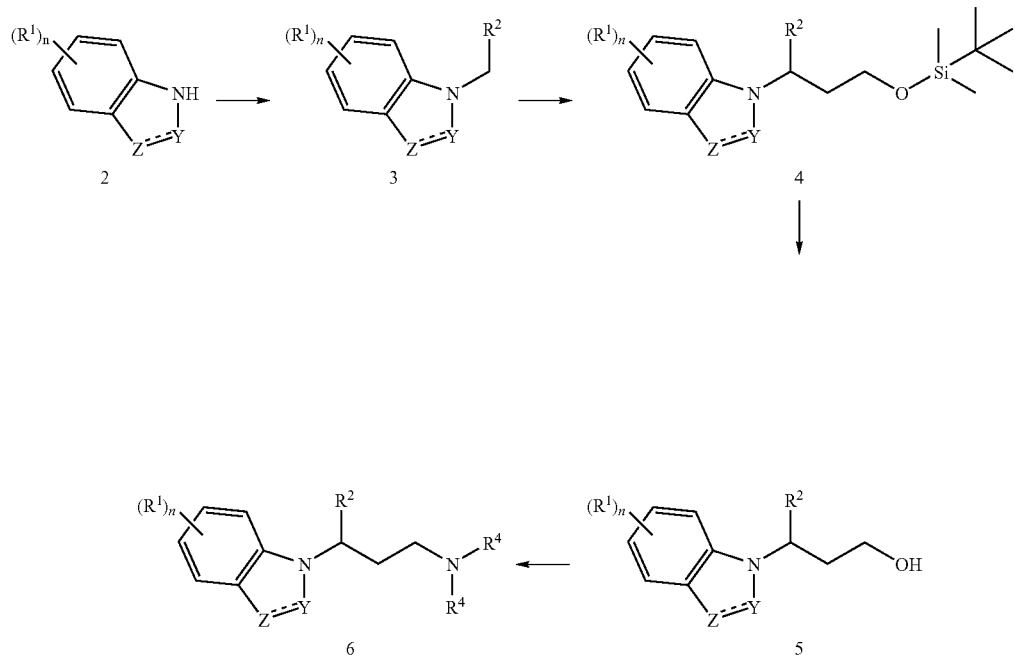

Scheme 1

Compounds of formula 6 where Z is $C(R_5)_2$ can be prepared by following the synthetic sequence described in Scheme 1. Compounds of formula 2 are either available from commercial sources or are accessible through methods well established in the literature (for example, page 227 of International Patent Application WO 2000/066,556, the entire disclosure of which is incorporated herein by reference). A heterocycle of structure 2 where Z is $C(R_5)_2$ can be alkylated with an benzylic halide in the presence of a suitable base such as sodium hydride in a solvent such as dimethylformamide to give 3. This transformation may be accomplished by a variety of base and solvent combinations. Structure 3 may then be converted to 4 by treatment with butyl lithium in an aprotic solvent such as tetrahydrofuran and allowing the resulting anion to react with a suitably functionalized alkylating agent. In this case (2-bromoethoxy)-tert-butyldimethylsilane may be used. The siloxy group used to protect the alcohol functionality is removed by reacting 4 with tetrabutyl ammonium fluoride to give 5. Although a tert-butyldimethylsilyl group was used to protect the hydroxyl functionality, other hydroxyl protecting groups would also be useful for producing compounds of structure 5 (for alternative methods for removing tert-butyldimethylsiloxy protecting groups and other useful

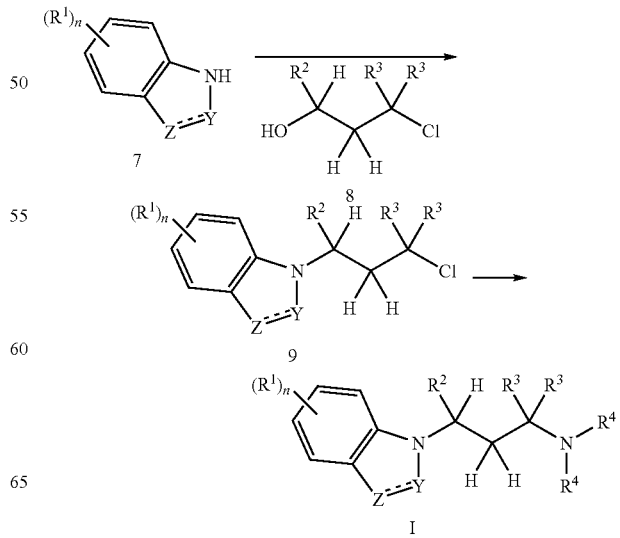

Scheme 2

Compounds of formula I can be prepared by following the synthetic sequence as described in Scheme 2. The hydroxyl group of compounds of formula 8 can be activated and subsequently replaced by an anion generated from compounds of formula 7 to produce compounds of formula 9. Any conventional method for activating a hydroxyl group of compounds of formula 8 and any conventional method for generating an anion of compounds of formula of 7 and subsequently replacing the activated hydroxyl group can be utilized for this conversion. In accordance with the preferred embodiment of this invention, the hydroxyl group of an appropriately substituted 3-chloropropanol of formula 8 can be activated via a Mitsunobu protocol and treated with compounds of formula 7 to produce compounds of formula 9. The Mitsonobo procedure is well documented (e.g., Hughes, David L., *Organic Preparations and Procedures International* (1996), 28(2), 127-64.). In accordance with the preferred embodiment of this invention, compounds of formula 9 may be generated by treatment of a mixture of compound 7, 9, and triphenylphosphine in an aprotic solvent such as THF with DIAD (diisopropyl azodicarboxylate). The reaction is generally executed at room temperature under a blanket of inert gas such as nitrogen over an approximate duration of 2 to 72 hours. Compounds of formula 7 and 8 are either available from commercial sources or are accessible through methods well established in the literature.

The compounds of this invention, I, can be prepared from compounds of formula 9 by displacing a terminal leaving group with a desired amine. Any conventional method for displacing a primary leaving group with an amine can be utilized for this conversion. In accordance with the preferred embodiment of this invention, the alkyl chloride of formula 9 is treated with a suitable amine in the presence of a nucleophilic iodide reagent such as potassium iodide or sodium iodide in an alcoholic solvent, e.g., methanol or ethanol to furnish compounds of formula I. The reaction is generally executed in a sealed tube at the elevated temperature ranging from 40 to 90° C. Compounds of formula I can be converted into a pharmaceutically acceptable salt using conventional methods.

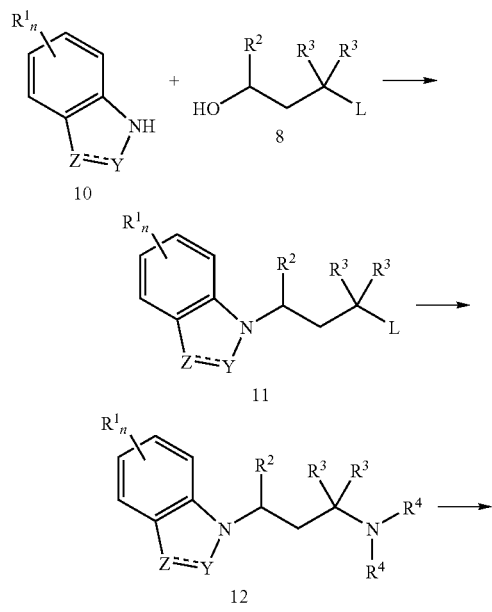

Scheme 3

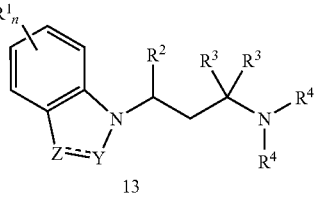

13 where: $R_1$, $R_2$, $R_3$, $R_4$, X, Z, and n are as previously defined
L = any conventional leaving group such as Cl, Br, I, OMs, OTs As shown in Scheme 3, compounds of formula 12 can be prepared by cross coupling reaction between compounds of formula 10 and aryl-propanols of formula 8, followed by displacing the primary leaving group L with a desired amine. Any conventional method for the cross coupling between compounds of formula 10 and aryl-propanols of formula 8, and any conventional method for displacing a primary leaving group with an amine can be utilized for this conversion. Accordingly, compounds of formula 10 and aryl-propanols of formula 8 are cross-coupled by the action of triarylphosphine and dialkyl azodicarboxylate (Mitsunobu, O. *Synthesis* 1981, 1; Hughes, D. L. *Org. Reactions*, 1992, 42, 335; Hughes, D. L. *Org. Prep. Proc. Int.* 1996, 28, 127) in tetrahydrofuran at temperatures between 0 to 40° C to give compounds of formula 11. Treatment of compounds of formula 11 with an excess of alcoholic amine solution in a sealed reaction vessel at temperatures between 20° C. to about 130° C. (depending on the reactivity of the leaving group L and the amines) gives compounds of formula 12. The aryl-propanols of formula 8 may exist as a racemic mixture or single enantiomers (optical isomers) and are either available from commercial sources or are accessible through methods well established in the literature. If it is desired to produce a single enantiomer of compounds of formula 8, asymmetric reduction of an aryl propyl ketone can be performed using chiral organoborane reagents (Srebnik, M, et. al., *J. Org. Chem.* 1988, 53, 2916). L can be any conventional leaving group such as chlorine, bromine, iodine, mesylate or tosylate. Compounds of formula 10 are either available from commercial sources or are accessible through methods well established in the literature.

Compounds of formula 13 where Y is methylene can be prepared by reduction of compounds of formula 12 where Y is carbonyl. Any conventional method for the reduction of an amide to an amine can be utilized for this conversion. Accordingly, compounds of formula 12 are treated with borane in tetrahydrofuran at 70° C. to give compounds of formula 13. Other reducing agents such as lithium aluminum hydride, diisobutylaluminum hydride, sodium bis(2-methoxyethoxy) aluminum hydride or sodium borohydride can also be utilized for this transformation.

In other embodiments, the invention is directed to pharmaceutical compositions, comprising:
a. at least compound of formula I, or pharmaceutically acceptable salt thereof;

and b. at least one pharmaceutically acceptable carrier.

Generally, the compound of formula I, or a pharmaceutically acceptable salt thereof, will be present at a level of from about 0.1%, by weight, to about 90% by weight, based on the total weight of the pharmaceutical composition, based on the total weight of the pharmaceutical composition. Preferably, the compound of formula I, or a pharmaceutically acceptable salt thereof, will be present at a level of at least about 1%, by weight, based on the total weight of the pharmaceutical composition. More preferably, the compound of formula I, or a pharmaceutically acceptable salt thereof, will be present at a level of at least about 5%, by weight, based on the total weight of the pharmaceutical composition. Even more preferably, the norepinephrine reuptake inhibitor or a pharmaceutically acceptable salt thereof will be present at a level of at least about 10%, by weight, based on the total weight of the pharmaceutical composition. Yet even more preferably, the compound of formula I, or a pharmaceutically acceptable salt thereof, will be present at a level of at least about 25%, by weight, based on the total weight of the pharmaceutical composition.

Such compositions are prepared in accordance with acceptable pharmaceutical procedures, such as described in *Remington's Pharmaceutical Sciences,* 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In another embodiment of the present invention, the compounds useful in the present invention may be administered to a mammal with one or more other pharmaceutical active agents such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention.

The term "combination therapy" refers to the administration of two or more therapeutic agents or compounds to treat a therapeutic condition or disorder described in the present disclosure, for example hot flush, sweating, thermoregulatory-related condition or disorder, or other. Such administration includes use of each type of therapeutic agent in a concurrent manner. In either case, the treatment regimen will provide beneficial, effects of the drug combination in treating the conditions or disorders described herein.

The route of administration may be any route, which effectively transports the active compound of formula I, or a pharmaceutically acceptable salt thereof, to the appropriate or desired site of action, such as oral, nasal, pulmonary, transdermal, such as passive or iontophoretic delivery, or parenteral, e.g. rectal, depot, subcutaneous, intravenous, intraurethral, intramuscular, intranasal, ophthalmic solution or an ointment. Furthermore, the administration of compound of formula I, or pharmaceutically acceptable salt thereof, with other active ingredients may be concurrent or simultaneous.

It is believed that the present invention described presents a substantial breakthrough in the field of treatment, alleviation, inhibition, and/or prevention of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

Accordingly, in one embodiment, the present invention is directed to methods for treating or preventing a condition ameliorated by monoamine reuptake in a subject in need thereof, comprising the step of:

administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

"Vasomotor symptoms," "vasomotor instability symptoms" and "vasomotor disturbances" include, but are not limited to, hot flushes (flashes), insomnia, sleep disturbances, mood disorders, irritability, excessive perspiration, night sweats, fatigue, and the like, caused by, inter alia, thermoregulatory dysfunction.

The term "hot flush" is an art-recognized term that refers to an episodic disturbance in body temperature typically consisting of a sudden skin flushing, usually accompanied by perspiration in a subject.

The term "sexual dysfunction" includes, but is not limited to, condition relating to desire and/or arousal.

As used herein, "gastrointestinal and genitourinary disorders" includes irritable bowel syndrome, symptomatic GERD, hypersensitive esophagus, nonulcer dyspepsia, noncardiac chest pain, biliary dyskinesia, sphincter of Oddi dysfunction, incontinence (i.e., urge incontinence, stress incontinence, genuine stress incontinence, and mixed incontinence)(including the involuntary voiding of feces or urine, and dribbling or leakage or feces or urine which may be due to one or more causes including but not limited to pathology altering sphincter control, loss of cognitive function, overdistention of the bladder, hyperreflexia and/or involuntary urethral relaxation, weakness of the muscles associated with the bladder or neurologic abnormalities), interstitial cystitis (irritable bladder), and chronic pelvic pain (including, but not limited to vulvodynia, prostatodynia, and proctalgia).

As used herein, "chronic fatigue syndrome" (CFS) is a condition characterized by physiological symptoms selected from weakness, muscle aches and pains, excessive sleep, malaise, fever, sore throat, tender lymph nodes, impaired memory and/or mental concentration, insomnia, disordered sleep, localized tenderness, diffuse pain and fatigue, and combinations thereof.

As used herein, "fibromyalgia syndrome" (FMS) includes FMS and other somatoform disorders, including FMS associated with depression, somatization disorder, conversion disorder, pain disorder, hypochondriasis, body dysmorphic disorder, undifferentiated somatoform disorder, and somatoform NOS. FMS and other somatoform disorders are accompanied by physiological symptoms selected from a generalized heightened perception of sensory stimuli, abnormalities in pain perception in the form of allodynia (pain with innocuous stimulation), abnormalities in pain perception in the form of hyperalgesia (increased sensitivity to painful stimuli), and combinations thereof.

As used herein, "nervous system disorders," includes addictive disorders (including those due to alcohol, nicotine, and other psychoactive substances) and withdrawal syndrome, age-associated learning and mental disorders (including Alzheimer's disease), anorexia nervosa, bulimia nervosa, attention-deficit disorder with or without hyperactivity disorder bipolar disorder, pain, cyclothymic disorder, depression disorder (including major depressive disorder, refractory depression adolescent depression and minor depression), dysthymic disorder, generalized anxiety disorder (GAD), obesity (i.e., reducing the weight of obese or overweight patients), obsessive compulsive disorders and related spectrum disorders, oppositional defiant disorder, panic disorder, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), social phobia (including social anxiety disorder), selective serotonin reuptake inhibition (SSRI) "poop out" syndrome (i.e., wherein a patient who fails to maintain a satisfactory response to SSRI therapy after an initial period of satisfactory response).

As used herein, "pain," includes both acute pain and chronic pain, which may be centralized pain, peripheral pain, or combination thereof. The term includes many different types of pains including, but not limited to, neuropathic pain, visceral pain, musculoskeletal pain, bony pain, cancer pain, inflammatory pain, and combinations thereof, such as lower back pain, atypical chest pain, headache such as cluster headache, migraine, herpes neuralgia, phantom limb pain, pelvic pain, myofascial face pain, abdominal pain, neck pain, central pain, dental pain, opioid resistant pain, visceral pain, surgical pain, bone injury pain, pain during labor and delivery, pain resulting from burns, post partum pain, angina pain, neuropathic pain such as peripheral neuropathy and diabetic neuropathy, post-operative pain, and pain which is co-morbid with nervous system disorders described herein.

As used herein, the term "acute pain" refers to centralized or peripheral pain that is intense, localized, sharp, or stinging, and/or dull, aching, diffuse, or burning in nature and that occurs for short periods of time.

As used herein, the term "chronic pain" refers to centralized or peripheral pain that is intense, localized, sharp, or stinging, and/or dull, aching, diffuse, or burning in nature and that occurs for extended periods of time (i.e., persistent and/or regularly reoccurring), including, for the purpose of the present invention, neuropathic pain and cancer pain. Chronic pain includes neuropathic pain, hyperalgesia, and/or allodynia.

As used herein, the term "neuropathic pain" refers to chronic pain caused by damage to or pathological changes in the peripheral or central nervous systems. Examples of pathological changes related to neuropathic pain include prolonged peripheral or central neuronal sensitization, central sensitization related damage to nervous system inhibitory and/or exhibitory functions and abnormal interactions between the parasympathetic and sympathetic nervous systems. A wide range of clinical conditions may be associated with or form the basis for neuropathic pain including, for example, diabetes, post traumatic pain of amputation (nerve damage cause by injury resulting in peripheral and/or central sensitization such as phantom limb pain), lower back pain, cancer, chemical injury, toxins, other major surgeries, peripheral nerve damage due to traumatic injury compression, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, or viral or bacterial infections such as shingles or human immunodeficiency virus (HIV), and combinations thereof. Also included in the definition of neuropathic pain is a condition secondary to metastatic infiltration, adiposis dolorosa, burns, central pain conditions related to thalamic conditions, and combinations thereof.

As used herein, the term "hyperalgesia" refers to pain where there is an increase in sensitivity to a typically noxious stimulus.

As used herein, the term "allodynia" refers to an increase in sensitivity to a typically non-noxious stimulus.

As used herein, the term "visceral pain" refers to pain associated with or resulting from maladies of the internal organs, such as, for example, ulcerative colitis, irritable bowel syndrome, irritable bladder, Crohn's disease, rheumatologic (arthralgias), tumors, gastritis, pancreatitis, infections of the organs, biliary tract disorders, and combinations thereof.

As used herein, the term "female-specific pain" refers to pain that may be acute and/or chronic pain associated with female conditions. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes, and combinations thereof.

In one embodiment, the present invention is directed to methods for treating or preventing vasomotor symptoms in a subject in need thereof, comprising the step of:

administering to said subject an effective amount of at least one compound of formula I or pharmaceutically acceptable salt thereof.

When estrogen levels are low or estrogen is absent, the normal levels between NE and 5-HT is altered and this altered change in neurotransmitter levels may result in changes in the sensitivity of the thermoregulatory center. The altered chemical levels may be translated in the thermoregulatory center as heat sensation and as a response, the hypothalamus may activate the descending autonomic pathways and result in heat dissipation via vasodilation and sweating (hot flush) (FIG. 1). Accordingly, the estrogen deprivation may result in altered norepinephrine activity.

Figure 2:
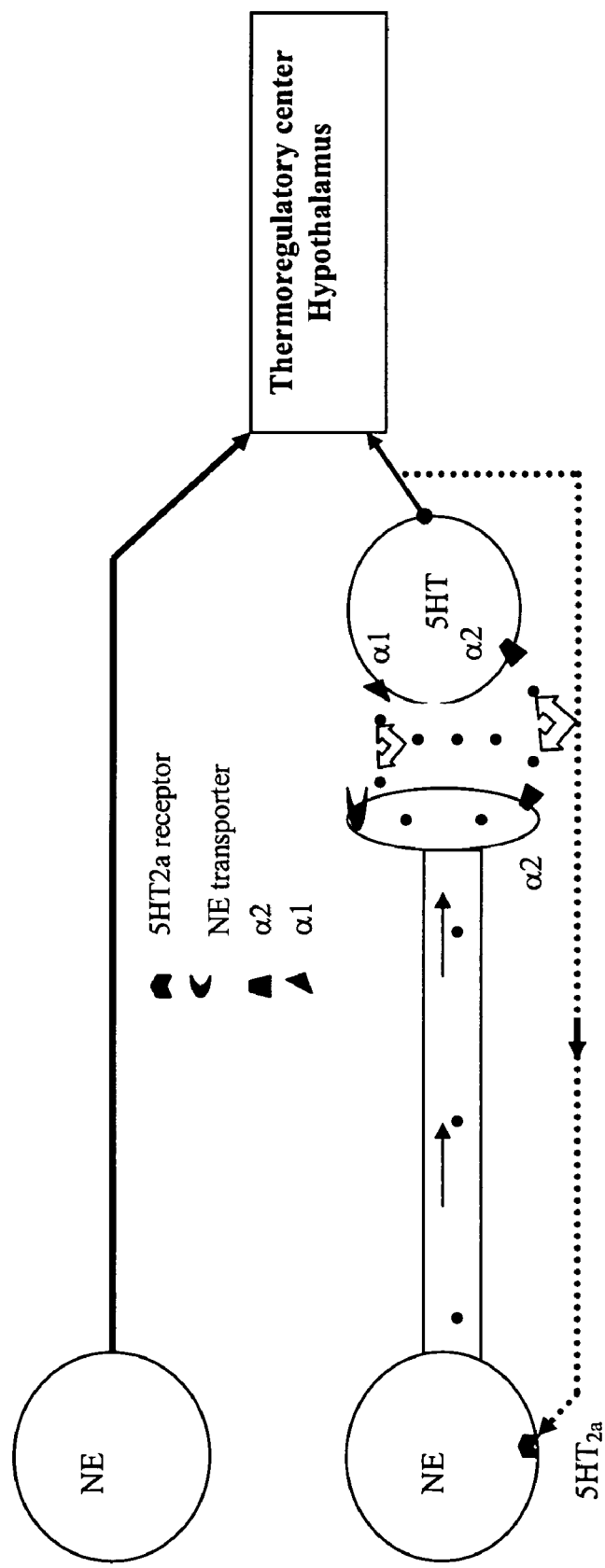
FIG. 2 is a schematic representation of the interactions of norepinephrine and serotonin and their respective receptors ($5-HT_{2a}$, $\alpha_1$ and $\alpha_2$-adrenergic).

Norepinephrine synthesized in perikarya of the brainstem is released at the nerve terminals in the hypothalamus and brainstem. In the hypothalamus, NE regulates the activity of neurons residing in the thermoregulatory center. In the brainstem, NE innervates serotoninergic neurons (5HT), and acting via adrenergic$_{\alpha1}$ and adrenergic$_{\alpha2}$ postsynaptic receptors, it stimulates the activity of the serotoninergic system. In response, 5-HT neurons also modulate the activity the thermoregulatory center and feedback to NE neurons. Via this feedback connection, 5-HT, acting via 5-HT$_{2a}$ receptors, inhibit the activity of NE neurons. Norepinephrine in the synaptic cleft is also taken up by NE transporter (NET) located in NE neurons. The transporter recycles NE and makes it available for multiple neurotransmission (FIG. 2).

The present invention provides a treatment for vasomotor symptoms by methods of recovering the reduced activity of norepinephrine. Norepinephrine activity in the hypothalamus or in the brainstem can be elevated by (i) blocking the activity of the NE transporter, (ii) blocking the activity of the presynaptic adrenergic$_{\alpha2}$ receptor with an antagonist, or (iii) blocking the activity of 5-HT on NE neurons with a 5-HT$_{2a}$ antagonist.

In another embodiment, the present invention is directed to methods for treating or preventing a depression disorder in a subject in need thereof, comprising the step of:

administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:

administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:

administering to said subject an effective amount of a compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of a compound of formula I or pharmaceutically acceptable salt thereof.

In another embodiment, the present invention is directed to methods for treating or preventing fibromylagia syndrome in a subject in need thereof, comprising the step of:

administering to said subject an effective amount of a compound of formula I or pharmaceutically acceptable salt thereof.

In further embodiments, the present invention is directed to methods for treating or preventing pain in a subject in need thereof, comprising the step of:

administering to said subject an effective amount of at least one compound of formula I or pharmaceutically acceptable salt thereof.

The pain may be, for example, acute pain (short duration) or chronic pain (regularly reoccurring or persistent). The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain or dental pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromylagia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In a more preferred embodiment, the compounds useful in this invention are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns, or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pains associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

1'-[(1R)-3-(methylamino)-1-phenylpropyl]spiro [cyclohexane-1,3'-indol]-2'(1'H)-one

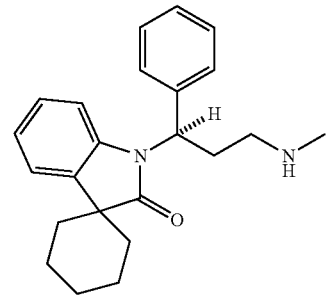

Step 1: 3-Methylamino-1-phenyl-propan-1-ol (2.5 g, 15.2 mmol) was dissolved in tetrahydrofuran (25 mL) and di-tert-butyldicarbonate (3.32 g, 15.2 mmol) was added and the mixture was stirred for 2 hours at 25° C. The mixture was concentrated and purified via Isco chromatography (Redisep, silica, gradient 0-40% ethyl acetate in hexane) to afford 3.2 g (80%) of tert-butyl [3-hydroxy-3-phenylpropyl]methylcarbamate.

HRMS: calculated for C15H23NO3+H+, 266.17507; found (ESI, [M+H]+), 266.1758 HPLC purity 100% at 210-370 nm, 8.7 minutes; Xterra RP18, 3.5u, 150×4.6 mm column, 1.2 mL/min, 85115-5195 (Ammon. Form. Buff. Ph=3.5/ACN+MeOH) for 10 minutes, hold 4 minutes.

Step 2: tert-Butyl [3-hydroxy-3-phenylpropyl]methylcarbamate (0.52 g, 1.96 mmol) was dissolved in $CH_2Cl_2$ (5 mL) and cooled to 0° C. Triphenylphosphine (1.02 g, 3.9 mmol) was added followed by N-bromosuccinimide (0.59 g, 3.3 mmol) and the mixture was stirred for 45 minutes. The reaction mixture was loaded directly onto silica gel and immediately purified via Isco chromatography (Redisep, silica, gradient 0-30% ethyl acetate in hexane) to afford 100 mg of (3-bromo-3-phenyl-propyl)-methyl-amine.

Step 3: Spiro[cyclohexane-1,3'-indol]-2'(1'H)-one (0.22 g, 1.1 mmol) was dissolved in dimethylformamide (2 mL) and NaH (46 mg, 1.2 mmol) was added and the mixture was stirred 30 minutes. (Reference for synthesis of Spiro[cyclohexane-1,3'-indol]-2'(1'H)-one and other 3,3'-dialkyloxindoles: page 227 of WO2000/066,556) A solution of (3-bromo-3-phenyl-propyl)-methyl-amine (0.18 g, 0.55 mmol) in dimethylformamide (1 mL) was added and the mixture was stirred for 16 hours. The reaction was quenched with saturated aqueous ammonium chloride, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-20% ethyl acetate in hexane) to afford 1'-[3-(tert-butoxycarbonyl-methylamino)-1-phenylpropyl]spiro[cyclohexane-1,3'-indol]-2'(1'H)-one (0.16 g, 65%) that was resolved by chiral HPLC.

Step 4: Approximately 170 mg of racemic 1'-[3-(tert-butoxycarbonyl-methylamino)-1-phenylpropyl]spiro[cyclohexane-1,3'-indol]-2'(1'H)-one was dissolved in 5 mL of methanol. 250 μL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H 5 μm, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

SFC Instrument: Berger MultiGram Prep SFC (Berger Instruments, Inc. Newark, Del.)
Column: Chiralpak AD-H; 5 μm; 250 mm L×20 mm ID (Chiral Technologies, Inc, Exton, Pa.)
Column temperature: 35° C.
SFC Modifier: 10% MeOH/90% CO2
Flow rate: 50 mL/min
Outlet Pressure: 100 bar
Detector: UV at 220 nm Step 5: 1'-[(1R)-3-(tert-butoxycarbonyl-methylamino)-1-phenylpropyl] spiro [cyclohexane-1,3'-indol]-2'(1'H)-one (70 mg, 0.15 mmol) was dissolved in ether (5 mL) and 2N HCl in ethyl acetate (0.3 mL, 0.6 mmol) was added. The mixture was stirred 16 hours then concentrated under a stream of nitrogen. The residue was purified via chromatography (silica, 5% methanol saturated with ammonia in chloroform) to give 50 mg of 1'-[(1R)-3-(methylamino)-1-phenylpropyl] spiro[cyclohexane-1,3'-indol]-2'(1'H)-one. The freebase was dissolved in ether (2 mL) and treated with 1N hydrochloric acid in ether (0.14 mL, 0.14 mmol, 1 equivalent). The white precipitate was collected and dried under vacuum to give 56 mg of 1'-[(1R)-3-(methylamino)-1-phenylpropyl]spiro[cyclohexane-1,3'-indol]-2'(1'H)-one hydrochloride.

HRMS: calculated for C23H28N2O+H+, 349.22744; found (ESI, [M+H]+), 349.2272; HPLC purity 100% at 210-370 nm, 8.4 minutes; Xterra RP18, 3.5u, 150×4.6 mm column, 1.2 mL/min, 85115-5/95 (Ammon. Form. Buff. Ph=3.5/ACN+MeOH) for 10 minutes, hold 4 minutes.

Example 2

1'-[(1S)-3-(methylamino)-1-phenylpropyl]spiro[cyclohexane-1.3'-indol]-2'(1'H)-one

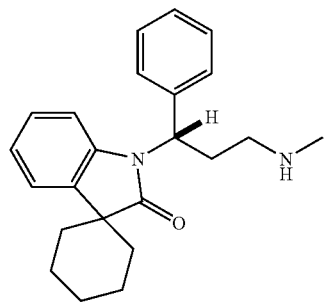

Step 1: 3-Methylamino-1-phenyl-propan-1-ol (2.5 g, 15.2 mmol) was dissolved in tetrahydrofuran (25 mL) and di-tert-butyldicarbonate (3.32 g, 15.2 mmol) was added and the mixture was stirred for 2 hours at 25° C. The mixture was concentrated and purified via Isco chromatography (Redisep, silica, gradient 0-40% ethyl acetate in hexane) to afford 3.2 g (80%) of tert-butyl [3-hydroxy-3-phenylpropyl]methylcarbamate.

HRMS: calculated for C15H23NO3+H+, 266.17507; found (ESI, [M+H]+), 266.1758 HPLC purity 100% at 210-370 nm, 8.7 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes.

Step 2: tert-Butyl [3-hydroxy-3-phenylpropyl]methylcarbamate (0.52 g, 1.96 mmol) was dissolved in CH2Cl2 (5 mL) and cooled to 0° C. Triphenylphosphine (1.02 g, 3.9 mmol) was added followed by N-bromosuccinimide (0.59 g, 3.3 mmol) and the mixture was stirred for 45 minutes. The reaction mixture was loaded directly onto silica gel and immediately purified via Isco chromatography (Redisep, silica, gradient 0-30% ethyl acetate in hexane) to afford 100 mg of (3-bromo-3-phenyl-propyl)-methyl-amine.

Step 3: Spiro[cyclohexane-1,3'-indol]-2'(1'H)-one (0.22 g, 1.1 mmol) was dissolved in dimethylformamide (2 mL) and NaH (46 mg, 1.2 mmol) was added and the mixture was stirred 30 minutes. A solution of (3-bromo-3-phenyl-propyl)-methyl-amine (0.18 g, 0.55 mmol) in dimethylformamide (1 mL) was added and the mixture was stirred for 16 hours. The reaction was quenched with saturated aqueous ammonium chloride, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-20% ethyl acetate in hexane) to afford 1'-[3-(tert-butoxycarbonyl-methylamino)-1-phenylpropyl] spiro[cyclohexane-1,3'-indol]-2'(1'H)-one (0.16 g, 65%) that was resolved by chiral HPLC.

Step 4: Approximately 170 mg of racemic 1'-[3-(tert-butoxycarbonyl-methylamino)-1-phenylpropyl]spiro[cyclohexane-1,3'-indol]-2'(1'H)-one was dissolved in 5 mL of methanol. 250 μL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H 5 μm, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

SFC Instrument: Berger MultiGram Prep SFC (Berger Instruments, Inc. Newark, Del.)
Column: Chiralpak AD-H; 5 μm; 250 mm L×20 mm ID (Chiral Technologies, Inc, Exton, Pa.)
Column temperature: 35° C.
SFC Modifier: 10% MeOH/90% CO2
Flow rate: 50 mL/min
Outlet Pressure: 100 bar
Detector: UV at 220 nm Step 5: 1'-[(1S)-3-(tert-butoxycarbonyl-methylamino)-1-phenylpropyl]spiro[cyclohexane-1,3'-indol]-2'(1'H)-one (70 mg, 0.15 mmol) was dissolved in ethanol (3 mL) and 2N HCl in ethyl acetate (0.3 mL, 0.6 mmol) was added. The mixture was stirred 16 hours then concentrated under a stream of nitrogen. The residue was purified via chromatography (silica, 5% methanol saturated with ammonia in chloroform) to give 54 mg of 1'-[(1S)-3-(methylamino)-1-phenylpropyl]spiro[cyclohexane-1,3'-indol]-2'(1'H)-one. The free base was dissolved in ether (2 mL) and treated with 1N hydrochloric acid in ether (0.16 mL, 0.16 mmol, 1 equivalent). The white precipitate was collected and dried under vacuum to give 54 mg of 1'-[(1S)-3-(methylamino)-1-phenylpropyl]spiro[cyclohexane-1,3'-indol]-2'(1'H)-one hydrochloride.

HRMS: calculated for C23H28N2O+H+, 349.22744; found (ESI, [M+H]+), 349.2265; HPLC purity 100% at 210-370 nm, 8.4 minutes; Xterra RP18, 3.5u, 150×4.6 mm col-

Example 3

1'-[(1R)-1-(3-fluorophenyl)-3-(methylamino)propyl]spiro[cyclo hexane-1,3'-indol]-2'(1'H)-one

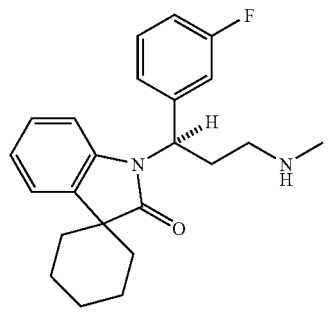

Step 1: Spiro[cyclohexane-1,3'-indol]-2'(1'H)-one (1.0 g, 5 mmol) was dissolved in dimethylformamide (10 mL) and NaH (0.21 g, 5.5 mmol) was added and the mixture was stirred 30 minutes then 3-fluorobenzyl bromide (1.04 g, 5.5 mmol) was added. The mixture was stirred 2 hours then quenched with saturated aqueous ammonium chloride, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-20% ethyl acetate in hexane) to afford 0.8 g of 1'-(3-fluorobenzyl)spiro[cyclohexane-1,3'-indol]-2'(1'H)-one.

HRMS: calculated for C2OH20FNO+H+, 310.16017; found (ESI, [M+H]+), 310.1588; HPLC purity 96.7% at 210-370 nm, 10.9 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes.

Step 2: 1'-(3-fluorobenzyl)spiro[cyclohexane-1,3'-indol]-2'(1'H)-one (0.61 g, 1.97 mmol) was dissolved in THF and cooled to −78° C. n-Butyl lithium (2.5 M in hexane, 0.87 mL, 2.2 mmol) was added dropwise and the mixture was warmed to 0° C. 2-Bromoethoxy)-tert-butyldimethylsilane (0.65 mL, 3 mmol) was added and the mixture was allowed to warm to 25° C. The mixture was stirred for 16 hours then quenched with saturated aqueous ammonium chloride, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-10% ethyl acetate in hexane) to afford 0.86 g (92%) 1'-[3-{[tert-butyl(dimethyl)silyl]oxy}-1-(3-fluorophenyl)propyl]spiro[cyclohexane-1,3'-indol]-2'(1'H)-one.

HRMS: calculated for C28H38FNO2Si+H+, 468.27286; found (ESI, [M+H]+), 468.2774 HPLC purity 97.9% at 210-370 nm, 12.6 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes.

Step 3: 1'-[3-{[tert-butyl(dimethyl)silyl]oxy}-1-(3-fluorophenyl) propyl]spiro-[cyclohexane-1,3'-indol]-2'(1'H)-one (0.85 g, 1.82 mmol) was dissolved in tetrahydrofuran and tetrabutyl ammonium fluoride (1.0 M in THF, 3.64 mL, 3.64 mmol) was added and the mixture was stirred for 1 hour. Reaction was quenched with saturated aqueous ammonium chloride then saturated sodium bicarbonate was added, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-100% ethyl acetate in hexane) to afford 0.54 g (84%) racemic 1'-[1-(3-fluorophenyl)-3-hydroxypropyl]spiro[cyclohexane-1,3'-indol]-2'(1'H)-one that was resolved by chiral HPLC Step 4: Approximately 540 mg of racemic 1'-[1-(3-fluorophenyl)-3-hydroxypropyl]spiro[cyclohexane-1,3'-indol]-2'(1'H)-one was dissolved in 10 mL of methanol. 250 µL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H 5 µm, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

SFC Instrument: Berger MultiGram Prep SFC (Berger Instruments, Inc. Newark, Del.)

Column: Chiralpak AD-H; 5 µm; 250 mm L×20 mm ID (Chiral Technologies, Inc, Exton, Pa.)

Column temperature: 35° C.

SFC Modifier: 15% MeOH/85% CO2

Flow rate: 50 mL/min

Outlet Pressure: 100 bar

Detector: UV at 220 nm

1'-[(1R)-1-(3-fluorophenyl)-3-hydroxypropyl]spiro[cyclohexane-1,3'-indol]-2'(1'H)-one HPLC purity 100% at 210-370 nm, 10.1 minutes; Xterra RP18, 3.5u, 150×4.6 mm column, 1.2 mL/min, 85/15-5195 (Ammon. Form. Buff. Ph=3.5/ACN+MeOH) for 10 minutes, hold 4 minutes. HRMS: calculated for C22H24FNO2+H+, 354.18638; found (ESI, [M+H]+), 354.1874;

Step 5: 1'-[(1R)-1-(3-fluorophenyl)-3-hydroxypropyl]spiro [cyclohexane-1,3'-indol]-2'(1'H)-one (0.26 g, 0.74 mmol) was dissolved in pyridine (4 mL) and toluenesufonyl chloride (0.21 g, 1.1 mmol) was added. Stirred for 3 hours then the reaction mixture was diluted with ethyl acetate and washed with water, 2N hydrochloric acid, saturated copper sulfate, 2N hydrochloric acid, and saturated brine. The organic layer was separated, dried over anhydrous magnesium sulfate, filtered, and concentrated in vacuo. The crude product was immediately dissolved in methylamine (8M in ethanol, 30 mL) and stirred for 16 hours. The mixture was concentrated in vacuo and purified via chromatography (silica, 5% methanol saturated with ammonia in chloroform) to give 1'-[(1R)-1-(3-fluorophenyl)-3-(methylamino)propyl]spiro[cyclohexane-1,3'-indol]-2'(1'H)-one as a colorless oil (0.26 g). The freebase was dissolved in ether (5 mL) and treated with 1N hydrochloric acid in ether (0.71 mL, 1.0 equivalent). The white precipitate was collected and dried under vacuum to give 203 mg (51% over three steps) 1'-[(1R)-1-(3-fluorophenyl)-3-(methylamino)propyl]spiro[cyclohexane-1,3'-indol]-2'(1'H)-one hydrochloride.

MS (ESI) m/z 367.2176; HPLC purity 100% at 210-370 nm, 8.6 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes. HRMS: calculated for C23H27FN2O+H+, 367.21802; found (ESI, [M+H]+), 367.2176;

Example 4

1'-[(1S)-1-(3-fluorophenyl)-3-(methylamino)propyl]
spiro[cyclohexane-1,3'-indol]-2'(1'H)-one

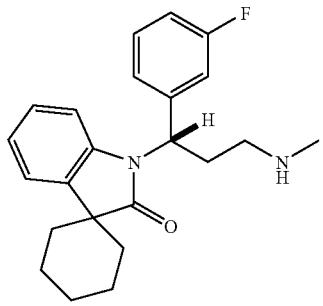

Step 1: Spiro[cyclohexane-1,3'-indol]-2'(1'H)-one (1.0 g, 5 mmol) was dissolved in dimethylformamide (10 mL) and NaH (0.21 g, 5.5 mmol) was added and the mixture was stirred 30 minutes then 3-fluorobenzyl bromide (1.04 g, 5.5 mmol) was added. The mixture was stirred 2 hours then quenched with saturated aqueous ammonium chloride, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-20% ethyl acetate in hexane) to afford 0.8 g of 1'-(3-fluorobenzyl)spiro[cyclohexane-1,3'-indol]-2'(1'H)-one.

HRMS: calculated for C20H20FNO+H+, 310.16017; found (ESI, [M+H]+), 310.1588; HPLC purity 96.7% at 210-370 nm, 10.9 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes.

Step 2: 1'-(3-fluorobenzyl)spiro[cyclohexane-1,3'-indol]-2'(1'H)-one (0.61 g, 1.97 mmol) was dissolved in THF and cooled to −78° C. n-Butyl lithium (2.5 M in hexane, 0.87 mL, 2.2 mmol) was added dropwise and the mixture was warmed to 0° C. (2-Bromoethoxy)-tert-butyldimethylsilane (0.65 mL, 3 mmol) was added and the mixture was allowed to warm to 25° C. The mixture was stirred for 16 hours then quenched with saturated aqueous ammonium chloride, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-10% ethyl acetate in hexane) to afford 0.86 g (92%) 1'-[3-{[tert-butyl(dimethyl)silyl]oxy}-1-(3-fluorophenyl)propyl]spiro[cyclohexane-1,3'-indol]-2'(1'H)-one.

HRMS: calculated for C28H38FNO2Si+H+, 468.27286; found (ESI, [M+H]+), 468.2774 HPLC purity 97.9% at 210-370 nm, 12.6 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes.

Step 3: 1'-[3-{[tert-butyl(dimethyl)silyl]oxy}-1-(3-fluorophenyl)propyl]spiro-[cyclohexane-1,3'-indol]-2'(1'H)-one (0.85 g, 1.82 mmol) was dissolved in tetrahydrofuran and tetrabutyl ammonium fluoride (1.0 M in THF, 3.64 mL, 3.64 mmol) was added and the mixture was stirred for 1 hour. Reaction was quenched with saturated aqueous ammonium chloride then saturated sodium bicarbonate was added, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-100% ethyl acetate in hexane) to afford 0.54 g (84%) racemic 1'-[1-(3-fluorophenyl)-3-hydroxypropyl]spiro[cyclohexane-1,3'-indol]-2'(1'H)-one that was resolved by chiral HPLC.

Step 4: Approximately 540 mg of racemic 1'-[1-(3-fluorophenyl)-3-hydroxypropyl]spiro[cyclohexane-1,3'-indol]-2'(1'H)-one was dissolved in 10 mL of methanol. 250 µL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H 5 µm, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

SFC Instrument: Berger MultiGram Prep SFC (Berger Instruments, Inc. Newark, Del.)

Column: Chiralpak AD-H; 5 µm; 250 mm L×20 mm ID (Chiral Technologies, Inc, Exton, Pa.)

Column temperature: 35° C.

SFC Modifier: 15% MeOH/85% CO2

Flow rate: 50 mL/min

Outlet Pressure: 100 bar

Detector: UV at 220 nm

1'-[(1S)-1-(3-fluorophenyl)-3-hydroxypropyl]spiro[cyclohexane-1,3'-indol]-2'(1'H)-one HPLC purity 99.0% at 210-370 nm, 10.1 minutes; Xterra RP18, 3.5u, 150×4.6 mm column, 1.2 mL/min, 85/15-5195 (Ammon. Form. Buff. Ph=3.5/ACN+MeOH) for 10 minutes, hold 4 minutes. HRMS: calculated for C22H24FNO2+H+, 354.18638; found (ESI, [M+H]+), 354.1886;

Step 5: 1'-[(1S)-1-(3-fluorophenyl)-3-hydroxypropyl]spiro[cyclohexane-1,3'-indol]-2'(1'H)-one (0.27 g, 0.76 mmol) was dissolved in pyridine (4 mL) and toluenesufonyl chloride (0.29 g, 2.0 mmol) was added. Stirred for 3 hours then the reaction mixture was diluted with ethyl acetate and washed with water, 2N hydrochloric acid, saturated copper sulfate, 2N hydrochloric acid, and saturated brine. The organic layer was separated, dried over anhydrous magnesium sulfate, filtered, and concentrated in vacuo. The crude product was immediately dissolved in methylamine (8M in ethanol, 30 mL) and stirred for 16 hours. The mixture was concentrated in vacuo and purified via chromatography (silica, 5% methanol saturated with ammonia in chloroform) to give 1'-[(1S)-1-(3-fluorophenyl)-3-(methylamino)propyl]spiro[cyclohexane-1.3'-indol]-2'(1'H)-one as a colorless oil (0.20 g). The freebase was dissolved in ether (5 mL) and treated with 1N hydrochloric acid in ether (0.55 mL, 1.0 equivalent). The white precipitate was collected and dried under vacuum to give 193 mg (63% over three steps) 1'-[(1S)-1-(3-fluorophenyl)-3-(methylamino)propyl]spiro[cyclohexane-1,3'-indol]-2'(1'H)-one hydrochloride.

MS (ESI) m/z 367.2171; HPLC purity 100% at 210-370 nm, 8.6 minutes; Xterra RP18, 3.5u, 150×4.6 mm column, 1.2 mL/min, 85/15-5/95 (Ammon. Form. Buff. Ph=3.5/ACN+

Example 5

7-fluoro-1-1[(1R)-1-(3-fluorophenyl)-3-(methylamino)propyl]-3,3-dimethyl-1,3-dihydro-2H-indol-2-one

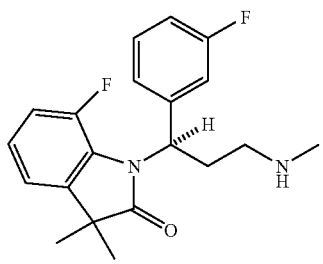

Step 1: To a solution of 2,6-difluoronitrobenzene (5.0 g, 31.44 mmol) in dry N,N-dimethylformamide (50 mL) was added potassium carbonate (4.41 g, 32 mmol) and dimethylmalonate (3.6 mL, 31.44 mmol). The reaction mixture was heated to 65° C. and stirred for 24 hours. After cooling to room temperature, the mixture was neutralized with a dilute aqueous solution of hydrochloric acid and extracted with diethyl ether. The ethereal layer was dried over anhydrous magnesium sulfate, and concentrated in vacuo. Crystallization from 5% ethyl acetate/hexane gave 4.6 g (54%) 2-(6-fluoro-2-nitro-phenyl)-malonic acid dimethyl ester. MS (ESI) m/z 272 [M+H]$^+$).

Step 2: 2-(6-Fluoro-2-nitro-phenyl)-malonic acid dimethyl ester (12 g, 44 mmol) in a 6N aqueous solution of hydrochloric acid (200 mL) was heated at reflux for 4 hours. The mixture was cooled, diluted with 250 mL of water and extracted with diethyl ether. The ethereal layer was dried over anhydrous magnesium sulfate, and concentrated in vacuo. Crystallization from 5% ethyl acetate/hexane gave 7.6 g of (6-fluoro-2-nitro-phenyl)-acetic acid (54%). MS (ESI) m/z 200 ([M+H]$^+$).

Step 3: A mixture of (6-fluoro-2-nitro-phenyl)-acetic acid (9.6 g, 48 mmol) and 10% palladium on carbon (1.3 g) in acetic acid (100 ml) was hydrogenated at 50 psi for 24 hours. The catalyst was removed by filtration through Celite and the solvent was evaporated. The residue was then dissolved in ethanol (100 mL) and pyridinium para-toluenesulfonate (50 mg) was added and the mixture heated at reflux for 1 hour. The mixture was cooled, poured into water, extracted with ethyl acetate and dried over anhydrous magnesium sulfate. The solvent was filtered and concentrated in vacuo. The solid was triturated with 5% ethyl acetate/hexane to give 6.0 g (83%) 7-fluoro-1,3-dihydro-indol-2-one. MS (ESI) m/z 152, [M+H]$^+$).

Step 4: 7-Fluoro-1,3-dihydro-indol-2-one (7.3 g, 48 mmol) and lithium chloride (6.67 g, 158 mmol) were dissolved in tetrahydrofuran (200 mL). The solution was cooled to −78° C. and n-butyllithium (40 mL, 100 mmol) was added slowly over a 15 minute period. After 20 minutes at −78° C., methyl iodide (6 mL, 96 mmol) was added and the mixture allowed to warm to room temperature. After 24 hours, the mixture was poured into water and extracted with ethyl acetate. The organic layer was dried over anhydrous magnesium sulfate, and concentrated in vacuo. The crude product was purified via Biotage chromatography (Flash40i, silica, 10% then 20% ethyl acetate/hexane) gave 4.1 g (48%) 7-fluoro-3,3-dimethyl-1,3-dihydro-2H-indol-2-one. MS (ESI) m/z 180, [M+H]$^+$).

Step 5: 7-fluoro-3,3-dimethyl-1,3-dihydro-2H-indol-2-one (1.3 g, 7.3 mmol) was dissolved in dimethylformamide (14 mL) and NaH (0.30 g, 8 mmol) was added and the mixture was stirred 30 minutes then 3-fluorobenzyl bromide (1.5 g, 8.0 mmol) was added. The mixture was stirred 4 hours then quenched with saturated aqueous ammonium chloride, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-20% ethyl acetate in hexane) to afford 1.7 g (81%) of 7-fluoro-1-(3-fluorobenzyl)-3,3-dimethyl-1,3-dihydro-2H-indol-2-one.

MS (ESI) m/z 288.1210; HPLC purity 99.5% at 210-370 nm, 10.0 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes. HRMS: calculated for C17H15F2NO+H+, 288.11945; found (ESI, [M+H]+), 288.1210

Step 6: 7-fluoro-1-(3-fluorobenzyl)-3,3-dimethyl-1,3-dihydro-2H-indol-2-one (1.01 g, 3.5 mmol) was dissolved in tetrahydrofuran and cooled to −78° C. n-Butyl lithium (2.5 M in hexane, 1.55 mL, 3.97 mmol) was added dropwise and the mixture was warmed to 0° C. (2-Bromoethoxy)-tert-butyldimethylsilane (1.14 mL, 5.25 mmol) was added and the mixture was allowed to warm to 25° C. The mixture was stirred for 16 hours then quenched with saturated aqueous ammonium chloride, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-10% ethyl acetate in hexane) to afford 0.8 g (55%) 1-[3-{[tert-butyl(dimethyl)silyl]oxy}-1-(3-fluorophenyl)propyl]-7-fluoro-3,3-dimethyl-1,3-dihydro-2H-indol-2-one.

MS (ESI) m/z 446.2352; HPLC purity 96.8% at 210-370 nm, 12.2 minutes; Xterra RP18, 3.5u, 150×4.6 mm column, 1.2 mL/min, 85/15-5195 (Ammon. Form. Buff. Ph=3.5/ACN+MeOH) for 10 minutes, hold 4 minutes. HRMS: calculated for $C_{25}H_{33}F_2NO_2Si$+H+, 446.23214; found (ESI, [M+H]+), 446.2352.

Step 7: 1-[3-{[tert-butyl(dimethyl)silyl]oxy}-1-(3-fluorophenyl)propyl]-7-fluoro-3,3-dimethyl-1,3-dihydro-2H-indol-2-one (0.80 g, 1.8 mmol) was dissolved in tetrahydrofuran and tetrabutyl ammonium fluoride (1.0 M in THF, 5.3 mL, 5.3 mmol) was added and the mixture was stirred for 1 hour. Reaction was quenched with saturated aqueous ammonium chloride then saturated sodium bicarbonate was added, diluted with ether, washed with water, and saturated brine. The organic layer was separated, dried over anhydrous magnesium sulfate, filtered, and concentrated in vacuo. The crude product was purified via Isco chromatography (Redisep, silica, gradient 5-50% ethyl acetate in hexane) to afford 0.58 g (97%) racemic 7-fluoro-1-[1-(3-fluorophenyl)-3-hydroxypropyl]-3,3-dimethyl-1,3-dihydro-2H-indol-2-one that was resolved by chiral HPLC.

Step 8: Approximately 580 mg of racemic 7-fluoro-1-[1-(3-fluorophenyl)-3-hydroxypropyl]-3,3-dimethyl-1,3-dihydro-2H-indol-2-one was dissolved in 10 mL of methanol. 500 μL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H 5 μm, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

SFC Instrument: Berger MultiGram Prep SFC (Berger Instruments, Inc. Newark, Del.)
Column: Chiralpak AD-H; 5 μm; 250 mm L×20 mm ID (Chiral Technologies, Inc, Exton, Pa.)
Column temperature: 35° C.
SFC Modifier: 15% MeOH/85% $CO_2$
Flow rate: 50 mL/min
Outlet Pressure: 100 bar
Detector: UV at 220 nm 7-fluoro-1-[(1R)-1-(3-fluorophenyl)-3-hydroxypropyl]-3,3-dimethyl-1,3-dihydro-2H-indol-2-one:

HPLC purity 100% at 210-370 nm, 9.1 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes. HRMS: calculated for C19H19F2NO2+H+, 332.14566; found (ESI-FTMS, [M+H]1+), 332.1439;

Step 9: 7-fluoro-1-[(1R)-1-(3-fluorophenyl)-3-hydroxypropyl]-3,3-dimethyl-1,3-dihydro-2H-indol-2-one (0.24 g, 0.73 mmol) was dissolved in pyridine (5 mL) and toluenesufonyl chloride (0.18 g, 0.94 mmol) was added. Stirred for 6 hours then the reaction mixture was diluted with ethyl acetate and washed with water, 2N hydrochloric acid, saturated copper sulfate, 2N hydrochloric acid, and saturated brine. The organic layer was separated, dried over anhydrous magnesium sulfate, filtered, and concentrated in vacuo. The crude product was immediately dissolved in methylamine (8M in ethanol, 25 mL) and stirred for 16 hours. The mixture was concentrated in vacuo and purified via chromatography (silica, 3% methanol saturated with ammonia in chloroform) to give 7-fluoro-1-[(1R)-1-(3-fluorophenyl)-3-(methylamino)propyl]-3,3-dimethyl-1,3-dihydro-2H-indol-2-one as a colorless oil (0.22 g). The freebase was dissolved in ether (5 mL) and treated with 1N hydrochloric acid in ether (0.64 mL, 1.0 equivalent). The white precipitate was collected and dried under vacuum to give 120 mg (43% over three steps) 7-fluoro-1-[(1R)-1-(3-fluorophenyl)-3-(methylamino)propyl]-3,3-dimethyl-1,3-dihydro-2H-indol-2-one hydrochloride.

HPLC purity 100% at 210-370 nm, 7.5 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes. HRMS: calculated for $C_{20}H_{22}F_2N_2O$+H+, 345.17729; found (ESI, [M+H]+), 345.1779;

Example 6

7-fluoro-1-[(1S)-1-(3-fluorophenyl)-3-(methylamino)propyl]-3,3-dimethyl-1,3-dihydro-2H-indol-2-one

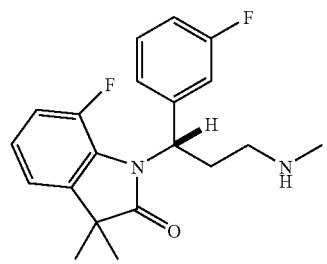

Step 1: Approximately 580 mg of racemic 7-fluoro-1-[1-(3-fluorophenyl)-3-hydroxypropyl]-3,3-dimethyl-1,3-dihydro-2H-indol-2-one was dissolved in 10 mL of methanol. 500 μL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H 5 μm, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

SFC Instrument: Berger MultiGram Prep SFC (Berger Instruments, Inc. Newark, Del.)
Column: Chiralpak AD-H; 5 μm; 250 mm L×20 mm ID (Chiral Technologies, Inc, Exton, Pa.)
Column temperature: 35° C.
SFC Modifier: 15% MeOH/85% CO2
Flow rate: 50 mL/min
Outlet Pressure: 100 bar
Detector: UV at 220 nm 7-fluoro-1-[(1S)-1-(3-fluorophenyl)-3-hydroxypropyl]-3,3-dimethyl-1,3-dihydro-2H-indol-2-one:

HPLC purity 100% at 210-370 nm, 9.1 minutes; Xterra RP18, 3.5u, 150×4.6 mm column, 1.2 mL/min, 85115-5195 (Ammon. Form. Buff. Ph=3.5/ACN+MeOH) for 10 minutes, hold 4 minutes. HRMS: calculated for C19H19F2NO2+H+, 332.14566; found (ESI-FTMS, [M+H]1+), 332.14623;

Step 2: 7-fluoro-1-[(1S)-1-(3-fluorophenyl)-3-hydroxypropyl]-3,3-dimethyl-1,3-dihydro-2H-indol-2-one (0.25 g, 0.76 mmol) was dissolved in pyridine (5 mL) and toluenesufonyl chloride (0.19 g, 0.98 mmol) was added. Stirred for 6 hours then the reaction mixture was diluted with ethyl acetate and washed with water, 2N hydrochloric acid, saturated copper sulfate, 2N hydrochloric acid, and saturated brine. The organic layer was separated, dried over anhydrous magnesium sulfate, filtered, and concentrated in vacuo. The crude product was immediately dissolved in methylamine (8M in ethanol, 25 mL) and stirred for 16 hours. The mixture was concentrated in vacuo and purified via chromatography (silica, 3% methanol saturated with ammonia in chloroform) to give 7-fluoro-1-[(1S)-1-(3-fluorophenyl)-3-(methylamino)propyl]-3,3-dimethyl-1,3-dihydro-2H-indol-2-one as a colorless oil (0.16 g). The freebase was dissolved in ether (5 mL) and treated with 1N hydrochloric acid in ether (0.46 mL, 1.0 equivalent). The white precipitate was collected and dried under vacuum to give 123 mg (43% over three steps)

7-fluoro-1-[(1S)-1-(3-fluorophenyl)-3-(methylamino)propyl]-3,3-dimethyl-1,3-dihydro-2H-indol-2-one hydrochloride.

HPLC purity 100% at 210-370 nm, 7.4 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes. HRMS: calculated for C20H22F2N2O+H+, 345.17729; found (ESI, [M+H]+), 345.1762;

Procedure for Preparation of 1-[(1R)-3-hydroxy-1-phenylpropyl]-3,3-dimethyl-1,3-dihydro-2H-indol-2-one and 1-[(1S)-3-hydroxy-1-phenylpropyl]-3,3-dimethyl-1,3-dihydro-2H-indol-2-one

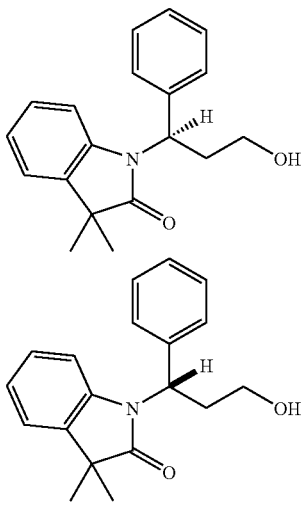

Step 1: 3,3-Dimethyl-1,3-dihydro-indol-2-one (5.5 g, 34 mmol) was dissolved in dimethylformamide (50 mL) and sodium hydride (1.4 g, 38 mmol) was added portionwise and the mixture was stirred 30 minutes then benzyl bromide (4.8 mL, 41 mmol) was added. The mixture was stirred 2 hours then quenched with saturated aqueous ammonium chloride, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-20% ethyl acetate in hexane) to afford 7.1 g (83%) of 1-benzyl-3,3-dimethyl-1,3-dihydro-2H-indol-2-one.

HPLC purity 96.4% at 210-370 nm, 9.5 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes. HRMS: calculated for $C_{17}H_{17}NO+H+$, 252.13829; found (ESI, [M+H]+), 252.142

Step 2: 1-benzyl-3,3-dimethyl-1,3-dihydro-2H-indol-2-one (4.0 g, 15.9 mmol) was dissolved in THF (75 mL) and cooled to −78° C. n-Butyl lithium (2.5 M in hexane, 7.0 mL, 17.5 mmol) was added dropwise and the mixture was warmed to 0° C. over 15 minutes. Cooled to −78° C. and (2-Bromoethoxy)-tert-butyldimethylsilane (5.2 mL, 23.9 mmol) was added and the mixture was allowed to warm to 25° C. The mixture was stirred for 2 hours then quenched with saturated aqueous ammonium chloride, diluted with ether, washed with water, and saturated brine. The organic layer was separated, dried over anhydrous magnesium sulfate, filtered, and concentrated in vacuo. The crude product was purified via Isco chromatography (Redisep, silica, gradient 0-10% ethyl acetate in hexane) to afford 4.1 g (63%) 1-(3-{[tert-butyl)dimethyl)silyl]oxy}-1-phenylpropyl)-3,3-dimethyl-1,3-dihydro-2H-indol-2-one.

HPLC purity 96.1% at 210-370 nm, 12.0 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes. HRMS: calculated for C25H35NO2Si+H+, 410.25098; found (ESI, [M+H]+), 410.2493.

Step 3: 1-(3-{[tert-butyl(dimethyl)silyl]oxy}-1-phenylpropyl)-3,3-dimethyl-1,3-dihydro-2H-indol-2-one (4.0 g, 9.8 mmol) was dissolved in tetrahydrofuran (50 mL) and tetrabutyl ammonium fluoride (1.0 M in THF, 14.7 mL, 14.7 mmol) was added and the mixture was stirred for 1 hour. Reaction was quenched with saturated aqueous ammonium chloride then saturated sodium bicarbonate was added, diluted with ether, washed with water, and saturated brine. The organic layer was separated, dried over anhydrous magnesium sulfate, filtered, and concentrated in vacuo. The crude product was purified via Isco chromatography (Redisep, silica, gradient 10-60% ethyl acetate in hexane) to afford 2.6 g (90%) racemic 1-[3-hydroxy-1-phenylpropyl]-3,3-dimethyl-1,3-dihydro-2H-indol-2-one that was resolved by chiral HPLC.

Step 4: Approximately 2.6 g of racemic 1-[3-hydroxy-1-phenylpropyl]-3,3-dimethyl-1,3-dihydro-2H-indol-2-one was dissolved in 16 mL of methanol. 200 µL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H 5 µm, 250 mm×4.6 mm ID column at 2.0 mL/min flow rate using Analytical Supercritical Fluid Chromatography (Berger Instruments, Inc. Newark, Del.). Enantiomers 1 and 2 were found to be 99.5% and 98.6% enantiomerically pure, respectively.

SFC Instrument: Berger MultiGram Prep SFC (Berger Instruments, Inc. Newark, Del.)

Column: Chiralpak AD-H; 5 µm; 250 mm L×20 mm ID (Chiral Technologies, Inc, Exton, Pa.)

Column temperature: 35° C.

SFC Modifier: 15% MeOH/85% CO2

Flow rate: 50 mL/min

Outlet Pressure: 100 bar

Detector: UV at 220 nm

1-[(1R)-3-hydroxy-1-phenylpropyl]-3,3-dimethyl-1,3-dihydro-2H-indol-2-one HPLC purity 100% at 210-370 nm, 8.6 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes.

HRMS: calculated for C19H21NO2+H+, 296.16450; found (ESI, [M+H]+), 296.1656;

1-[(1S)-3-hydroxy-1-phenylpropyl]-3,3-dimethyl-1,3-dihydro-2H-indol-2-one HPLC purity 97.2% at 210-370 nm, 8.6 minutes; Xterra RP18, 3.5u, 150×4.6 mm column, 1.2 mL/min, 85/15-5/95 (Ammon. Form. Buff. Ph=3.5/ACN+MeOH) for 10 minutes, hold 4 minutes. HRMS: calculated for $C_{19}H_{21}NO_2$+H+, 296.16450; found (ESI, [M+H]+), 296.1653;

Example 7

3,3-dimethyl-1-[(1S)-3-(methylamino)-1-phenylpropyl]-1,3-dihydro-2H-indol-2-one

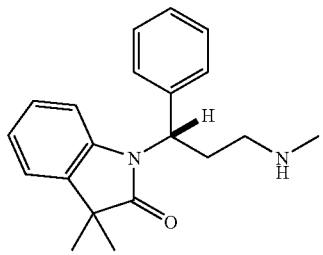

1-[(1S)-3-hydroxy-1-phenylpropyl]-3,3-dimethyl-1,3-dihydro-2H-indol-2-one (1.15 g, 3.9 mmol) was dissolved in pyridine (5 mL) and toluenesufonyl chloride (0.89 g, 4.6 mmol) was added. Stirred for 16 hours then the reaction mixture was diluted with ethyl acetate and washed with water, 2N hydrochloric acid, saturated copper sulfate, 2N hydrochloric acid, and saturated brine. The organic layer was separated, dried over anhydrous magnesium sulfate, filtered, and concentrated in vacuo. A portion of the crude product (100 mg, 0.21 mmol) was immediately dissolved in methylamine (8M in ethanol, 10 mL) and stirred for 16 hours. The mixture was concentrated in vacuo and purified via chromatography (silica, 0-15% methanol saturated with ammonia in chloroform) to give 3.3-dimethyl-1-[(1S)-3-(methylamino)-1-phenylpropyl]-1,3-dihydro-2H-indol-2-one as a colorless oil. The freebase was dissolved in ether (5 mL) and treated with 1N hydrochloric acid in ether (1.0 equivalent). The white precipitate was collected and dried under vacuum to give 43 mg 3,3-dimethyl-1-[(1S)-3-(methylamino)-1-phenylpropyl]-1,3-dihydro-2H-indol-2-one hydrochloride.

HPLC purity 99.4% at 210-370 nm, 8.8 minutes; Xterra RP18, 3.5u, 150×4.6 mm column, 1.2 mL/min, 85/15-5/95 (Ammon. Bicarb Buff. Ph=9.5/ACN+MeOH) for 10 minutes, hold 4 minutes. HRMS: calculated for $C_{20}H_{24}N_2O+H+$, 309.19614; found (ESI, [M+H]+), 309.1956;

Example 8

3,3-dimethyl-1-[(1R)-3-(methylamino)-1-phenylpropyl]-1,3-dihydro-2H-indol-2-one

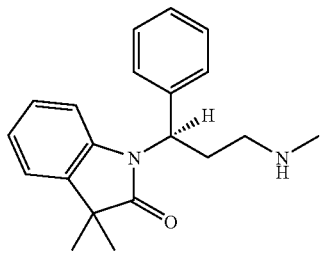

1-[(1S)-3-hydroxy-1-phenylpropyl]-3,3-dimethyl-1,3-dihydro-2H-indol-2-one (1.2 g, 4.1 mmol) was dissolved in pyridine (5 mL) and toluenesufonyl chloride (0.84 g, 4.4 mmol) was added. Stirred for 16 hours then the reaction mixture was diluted with ethyl acetate and washed with water, 2N hydrochloric acid, saturated copper sulfate, 2N hydrochloric acid, and saturated brine. The organic layer was separated, dried over anhydrous magnesium sulfate, filtered, and concentrated in vacuo. A portion of the crude product (100 mg, 0.21 mmol) was immediately dissolved in methylamine (8M in ethanol, 10 mL) and stirred for 16 hours. The mixture was concentrated in vacuo and purified via chromatography (silica, 0-15% methanol saturated with ammonia in chloroform) to give 3,3-dimethyl-1-[(1R)-3-(methylamino)-1-phenylpropyl]-1,3-dihydro-2H-indol-2-one as a colorless oil. The freebase was dissolved in ether (5 mL) and treated with 1N hydrochloric acid in ether (1.0 equivalent). The white precipitate was collected and dried under vacuum to give 44 mg 3,3-dimethyl-1-[(1R)-3-(methylamino)-1-phenylpropyl]-1,3-dihydro-2H-indol-2-one hydrochloride.

MS (ES) m/z 308.9; HPLC purity 99.6% at 210-370 nm, 8.8 minutes; Xterra RP18, 3.5u, 150×4.6 mm column, 1.2 mL/min, 85/15-5195 (Ammon. Bicarb Buff. Ph=9.5/ACN+MeOH) for 10 minutes, hold 4 minutes. HRMS: calculated for C20H24N2O+H+, 309.19614; found (ESI, [M+H]+), 309.1953;

Example 9

3,3-Dimethyl-1-[(1R)-3-(methylamino)-1-phenylpropyl]-1,3-dihydro-2H-indol-2-one hydrochloride

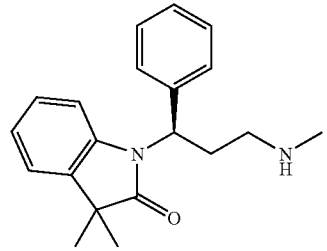

Step 1: To a mixture of 3,3-dimethyloxindole (409 mg, 2.53 mmol), (S)-3-chloro-1-phenyl-1-propanol (376 mg, 2.20 mmol) and triphenylphosphine (664 mg, 2.53 mmol) in tetrahydrofuran (5 mL) under nitrogen was added slowly diisopropyl azodicarboxylate (490 μL, 2.53 mmol) via a syringe. The resulting solution was stirred at room temperature overnight. Solvent was removed under reduced pressure and the viscous brown liquid residue was purified using Isco CombiFlash Companion chromatography (RediSep 12-g silica column, 0-12% ethyl acetate/hexane) to give 236 mg (34%) of 1-[(1R)-3-chloro-1-phenylpropyl]-3,3-dimethyl-1,3-dihydro-2H-indol-2-one as a viscous colorless liquid. MS (ES) m/z 314.1 ([M+H]$^+$); HRMS: calculated for $C_{19}H_{20}ClNO+H+$, 314.1306; found (ESI, [M+H]$^+$), 314.1299.

Step 2: A mixture of 1-[(1R)-3-chloro-1-phenylpropyl]-3,3-dimethyl-1,3-dihydro-2H-indol-2-one (220 mg, 0.700 mmol) and ethanolic solution of methylamine (33% in ethanol, 5 mL) was heated at 125° C. for 2 h with stirring in a sealed reaction vessel. Upon cooling, all volatiles were removed under reduced pressure. The resulting residue was dissolved in dichloromethane (20 mL), washed with aqueous potassium carbonate (5 mL), dried (anhydrous sodium sulfate), and concentrated. Purification by Isco CombiFlash Companion chromatography (RediSep 4-g silica column, 0-15% methanol/dichloromethane/0.5% triethylamine) gave 200 mg (93%) of 3,3-dimethyl-1-[(1R)-3-(methylamino)-1- phenylpropyl]-1,3-dihydro-2H-indol-2-one as a viscous colorless liquid, which was dissolved dichloromethane (5 mL) and treated with an ethereal solution of hydrochloric acid (1 M, 0.7 mL, 0.7 mmol). To the resulting solution was added hexane until white powder formed, which was collected, washed with hexane, and dried in vacuo to yield 3,3-dimethyl-1-[(1R)-3-(methylamino)-1-phenylpropyl]-1,3-dihydro-2H-indol-2-one hydrochloride as a white powder. MS (ES) m/z 308.9 ([M+H]$^+$); HRMS: calculated for $C_{20}H_{24}N_2O+H^+$, 309.1961; found (ESI, [M+H]$^+$), 309.1953.

Example 10

3,3-Dimethyl-1-[(1S)-3-(methylamino)-1-phenyl-proyl]-1,3-dihydro-2H-indol-2-one hydrochloride

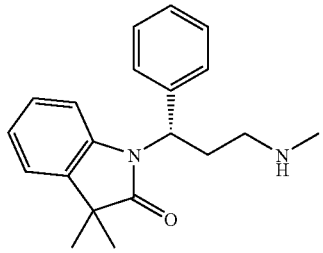

In an analogous manner to Example 9, step 1, 1-[(1S)-3-chloro-1-phenylpropyl]-3,3-dimethyl-1,3-dihydro-2H-indol-2-one was prepared from 3,3-dimethyloxindole[1] and (R)-3-chloro-1-phenyl-1-propanol as a viscous, colorless liquid. MS (ES) m/z 314.2 ([M+H]$^+$); HRMS: calculated for $C_{19}H_{20}ClCO +H^+$, 314.1306; found (ESI, [M+H]$^+$), 314.1304.

In an analogous manner to Example 9, step 2, 3,3-dimethyl-1-[(1S)-3-(methylamino)-1-phenylpropyl]-1,3-dihydro-2H-indol-2-one hydrochloride was prepared from 1-[(1S)-3-chloro-1-phenylpropyl]-3,3-dimethyl-1,3-dihydro-2H-indol-2-one as a white powder. MS (ES) m/z 309.0 ([M+H]$^+$); HRMS: calculated for $C_{20}H_{24}N_2O+H+$, 309.1961; found (ESI, [M+H]$^+$), 309.1956.

Example 11

7-Fluoro-3,3-dimethyl-1-[(1R)-3-(methylamino)-1-phenylpropyl]-1,3-dihydro-2H-indol-2-one hydrochloride

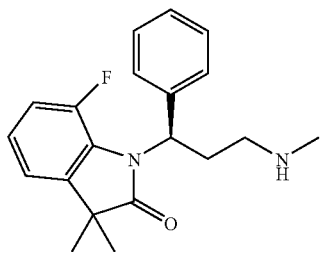

Step 1: In an analogous manner to Example 9, step 1, 1-[(1R)-3-chloro-1-phenylpropyl]-7-fluoro-3,3-dimethyl-1,3-dihydro-2H-indol-2-one was prepared from 7-fluoro-3,3-dimethyloxindole (example 5, steps 1-4) and (S)-3-chloro-1-phenyl-1-propanol as a viscous, colorless liquid. MS (ES) m/z 331.8 ([M+H]$^+$); HRMS: calculated for $C_{19}H_{19}ClFNO+$ H$^+$, 332.1212; found (ESI, [M+H]$^+$), 332.1212.

Step 2: In an analogous manner to Example 9, step 2, 7-fluoro-3,3-dimethyl-1-[(1R)-3-(methylamino)-1-phenylpropyl]-1,3-dihydro-2H-indol-2-one hydrochloride was prepared from 1-[(1R)-3-chloro-1-phenylpropyl]-7-fluoro-3,3-dimethyl-1,3-dihydro-2H-indol-2-one as a white powder. MS (ES) m/z 327.0 ([M+H]$^+$); HRMS: calculated for $C_{20}H_{23}FN_2O+H^+$, 327.1867; found (ESI, [M+H]$^+$), 327.1879.

Example 12

(3R)-3-(3,3-Dimethyl-2,3-dihydro-1H-indol-1-yl)-N-methyl-3-phenylpropan-1-amine hydrochloride

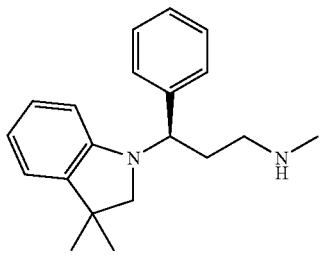

To a solution of 3,3-dimethyl-1-[(1R)-3-(methylamino)-1-phenylpropyl]-1,3-dihydro-2H-indol-2-one (Example 9, Step 2, 150 mg, 0.486 mmol) in dry tetrahydrofuran (3 mL) under nitrogen was added dropwise a solution of borane (1.0 M in tetrahydrofuran, 1.0 mL, 1.0 mmol, 2 equiv.) via a syringe. The resulting solution was heated at 70° C. with stirring for 2 h. Upon cooling, the reaction mixture was treated dropwise with a 2N aqueous solution of hydrochloric acid (2 mL), and was again heated at 60° C. for 20 minutes Upon cooling, solvent was removed under reduced pressure. To the residue was slowly added aqueous potassium carbonate (5 mL), and the mixture was extracted with dichloromethane (20 mL). The organic layer was washed with brine, dried (anhydrous sodium sulfate), and concentrated. Purification by Isco CombiFlash Companion chromatography (RediSep 4-g silica column, 0-15% methanol/dichloromethane/ 0.5% triethylamine) gave 100 mg (70%) of (3R)-3-(3,3-dimethyl-2,3-dihydro-1H-indol-1-yl)-N-methyl-3-phenylpropan-1-amine as a viscous brown liquid, which was dissolved dichloromethane (3 mL) and treated with an ethereal solution of hydrochloric acid (1 M, 0.37 mL, 0.37 mmol). To the resulting solution was added hexane until white powder formed, which was collected, washed with hexane, and dried in vacuo to yield (3R)-3-(3,3-dimethyl-2,3-dihydro-1H-indol-1-yl)-N-methyl-3-phenylpropan-1-amine hydrochloride as a yellow powder. MS (ES) m/z 295.3 ([M+H]$^+$); HRMS: calculated for $C_{20}H_{26}N_2+H^+$, 295.2169; found (ESI, [M+H]$^+$), 295.2160.

Example 13

(3R)-3-(7-Fluoro-3,3-dimethyl-2,3-dihydro-1H-indol-1-yl)-N-methyl-3-phenylpropan-1-amine hydrochloride

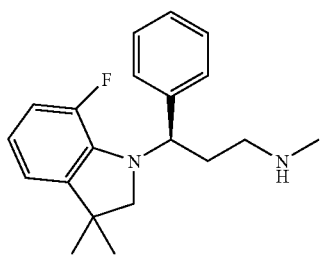

In an analogous manner to Example 4, (3R)-3-(7-fluoro-3,3-dimethyl-2,3-dihydro-1H-indol-1-yl)-N-methyl-3-phenylpropan-1-amine hydrochloride was prepared from 7-fluoro-3,3-dimethyl-1-[(1R)-3-(methylamino)-1-phenylpropyl]-1,3-dihydro-2H-indol-2-one (Example 11, step 2) as a white powder. MS (ES) m/z 312.9 ([M+H]$^+$); HRMS: calculated for $C_{20}H_{25}FN_2+H^+$, 313.2075; found (ESI, [M+H]$^+$), 313.2063.

Example 14

1-Ethyl-3-[(1R)-3-(methylamino)-1-phenylpropyl]-1,3-dihydro-2H-benzimidazol-2-one

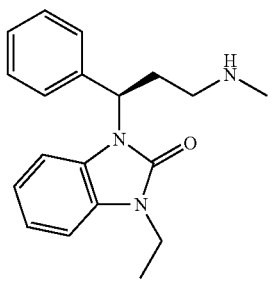

Step 1: To a solution of ethylamine in methanol (2.0 M, 150 mL, 300 mmol) was added 1-fluoro-2-nitrobenzene (8 mL, 75.7 mmol). The reaction mixture was placed in a sealed vessel and heated to 55° C. for 15 hours. The solvent was removed in vacuo and residue taken up in ethyl acetate (200 mL), washed with a saturated aqueous sodium bicarbonate solution (80 mL), and dried over anhydrous sodium sulfate (50 g). After removal of solvent, the residue was dissolved in anhydrous THF (150 mL) and to the solution added sodium borohydride (5.8 g, 153 mmol) and 5% palladium on carbon (150 mg). Methanol (25 mL) was then added at room temperature under nitrogen in a dropwise manner. After addition, the reaction mixture was stirred at room temperature for about 30 minutes until the reaction was complete and filtered through a pad of celite. The filtrate was taken up in ethyl acetate (200 mL), washed with a saturated aqueous ammonium chloride solution (80 mL), dried (Na$_2$SO$_4$), and concentrated. The residue was dissolved in anhydrous THF (200 mL) and to the solution was added 1,1'-carbonyldiimidazole (10 g, 62 mmol). The mixture was stirred at room temperature under nitrogen for 12 hours and ethyl acetate (250 mL) and a cold 3N aqueous HCl solution (200 mL) added. The organic layer was separated, dried (Na$_2$SO$_4$), and concentrated to afford 1-ethyl-1,3-dihydro-benzimidazol-2-one as a white solid (8.5g, 69% for three steps). MS (ES) m/z 163.2.

Step 2: To a mixture of 1-ethyl-1,3-dihydro-benzimidazol-2-one (1 g, 6.2 mmol), (S)-(−)-3-chloro-1-phenyl-1-propanol (1.16 g, 6.8 mmol), and triphenylphosphine (1.78 g, 6.8 mmol) in anhydrous THF (25 mL) was added DIAD (1.38 g, 6.8 mmol) under nitrogen at room temperature. The mixture was stirred under nitrogen at room temperature for 18 hrs and solvent removed in vacuo. The residue was purified by a silica gel column (33% ethyl acetate in hexane) to afford 1-[(1R)-3-chloro-1-phenylpropyl]-3-ethyl-1,3-dihydro-2H-benzimidazol-2-one as an oil (0.5g, 26%). MS (ESI) m/z 315.

Step 3: To a mixture of 1-[(1R)-3-chloro-1-phenylpropyl]-3-ethyl-1,3-dihydro-2H-benzimidazol-2-one (0.13 g, 0.4 mmol) and potassium iodide (0.2 g, 1.2 mmol) in methanol (5 mL) was added a solution of 33% methylamine in methanol (10 mL). The reaction solution was heated to 80° C. in a sealed tube for 3 hours and cooled to room temperature. The solvent was removed in vacuo and residue purified on a silica gel column (10-50% methanol in methylene chloride) to afford 1-ethyl-3-[(1R)-3-(methylamino)-1-phenylpropyl]-1,3-dihydro-2H-benzimidazol-2-one as an oil. The free base was dissolved in a minimum amount of ethanol and treated with a 2N ethereal solution of hydrochloric acid and stirred for 1 hour. The solvent was removed in vacuo and the residue was triturated with ether/dichloromethane to give 1-ethyl-3-[(1R)-3-(methylamino)-1-phenylpropyl]-1,3-dihydro-2H-benzimidazol-2-one HCl salt as a yellowish amorphous solid (30 mg, 22%). MS (ES) m/z 309.8.

Example 15

1-cyclopropyl-3-[(1S)-3-(methylamino)-1-phenylpropyl]-1,3-dihydro-2H-benzimidazol-2-one

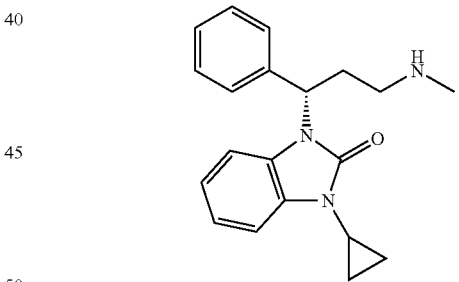

In an analogous manner to Example 14, step 1 1-cyclopropyl-1,3-dihydro-benzoimidazol-2-one was prepared from 1-fluoro-2-nitro-benzene and cyclopropyl amine. MS (ES) m/z 175.

In an analogous manner to Example 14, step 2 1-cyclopropyl-3-[(1S)-3-(chloro)-1-phenylpropyl]-1,3-dihydro-2H-benzimidazol-2-one was prepared from 1-cyclopropyl-1,3-dihydro-benzoimidazol-2-one and (R)-(+)-3-chloro-1-phenyl-1-propanol. MS (ES) m/z 327.1.

In an analogous manner to Example 14, step 3 1-cyclopropyl-3-[(1S)-3-(methylamino)-1-phenylpropyl]-1,3-dihydro-2H-benzimidazol-2-one HCl salt as a yellow amorphous solid was prepared from 1-cyclopropyl-3-[(1S)-3-(chloro)-1-phenylpropyl]-1,3-dihydro-2H-benzimidazol-2-one and methylamine. MS (ESI) m/z 322. HRMS: calculated for $C_{20}H_{23}N_3O+H^+$, 322.19139; found (ESI, [M+H]$^+$), 322.192.

Example 16

1-cyclopropyl-3-[(1R)-3-(methylamino)-1-phenyl-propyl]-1,3-dihydro-2H-benzimidazol-2-one

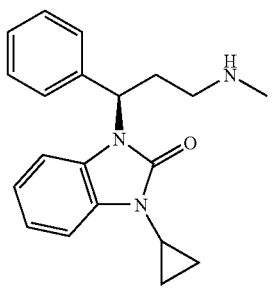

In an analogous manner to Example 14, step 2 1-cyclopropyl-3-[(1R)-3-(chloro)-1-phenylpropyl]-1,3-dihydro-2H-benzimidazol-2-one was prepared from 1-cyclopropyl-1,3-dihydro-benzoimidazol-2-one and S(−)-3-chloro-1-phenyl-1-propanol.

MS (ES) m/z 327.1.

In an analogous manner to Example 14, step 3 1-cyclopropyl-3-[(1R)-3-(methylamino)-1-phenylpropyl]-1,3-dihydro-2H-benzimidazol-2-one as HCl salt was prepared from 1-cyclopropyl-3-[(1R)-3-(chloro)-1-phenylpropyl]-1,3-dihydro-2H-benzimidazol-2-one.

$[\alpha]_D^{25}$=41.70 (c=10 mg/mL, MeOH); MS (ESI) m/z 322; HRMS: calculated for $C_{20}H_{23}N_3O+H+$, 322.19139; found (ESI, [M+H]$^+$), 322.1915.

Example 17

1-isopropyl-3-[(1S)-3-(methylamino)-1-phenylpropyl]-1,3-dihydro-2H-benzimidazol-2-one

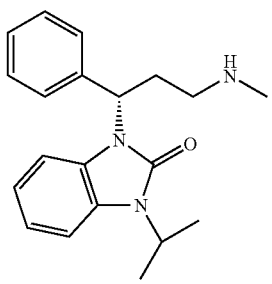

In an analogous manner to Example 14, step 1 1-isopropyl-1,3-dihydro-2H-benzimidazol-2-one was prepared from 1-fluoro-2-nitro-benzene and isobutyl amine.

MS (ES) m/z 176.9.

In an analogous manner to Example 14, step 2 1-isopropyl-3-[(1S)-3-(chloro)-1-phenylpropyl]-1,3-dihydro-2H-benzimidazol-2-one was prepared from 1-isopropyl-1,3-dihydro-2H-benzimidazol-2-one and R(+)-3-chloro-1-phenyl-1-propanol.

MS (ES) m/z 329.1.

In an analogous manner to Example 14, step 3 1-isopropyl-3-[(1S)-3-(methylamino)-1-phenylpropyl]-1,3-dihydro-2H-benzimidazol-2-one as HCl salt was prepared from 1-isopropyl-3-[(1S)-3-(chloro)-1-phenylpropyl]-1,3-dihydro-2H-benzimidazol-2-one and methyl amine. MS (ES) m/z 324.6; HRMS: calculated for $C_{20}H_{25}N_3O+H^+$, 324.20704; found (ESI, [M+H]$^+$), 324.2068.

Example 18

1-isopropyl-3-[(1R)-3-(methylamino)-1-phenylpropyl]-1,3-dihydro-2H-benzimidazol-2-one

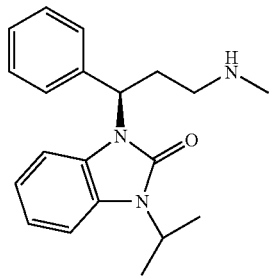

In an analogous manner to Example 14, step 2 1-isopropyl-3-[(1R)-3-(chloro)-1-phenylpropyl]-1,3-dihydro-2H-benzimidazol-2-one was prepared from 1-isopropyl-1,3-dihydro-2H-benzimidazol-2-one and S(−)-3-chloro-1-phenyl-1-propanol.

MS (ES) m/z 329.1.

In an analogous manner to Example 14, step 3 1-isopropyl-3-[(1R)-3-(methylamino)-1-phenylpropyl]-1,3-dihydro-2H-benzimidazol-2-one as HCl salt was prepared from 1-isopropyl-3-[(1R)-3-(chloro)-1-phenylpropyl]-1,3-dihydro-2H-benzimidazol-2-one and methyl amine. MS (ES) m/z 324.3; HRMS: calculated for $C_{20}H_{25}N_3O+H+$, 324.20704; found (ESI, [M+H]$^+$), 324.2076.

Example 19

1-[(1S)-3-(methylamino)-1-phenylpropyl]-3-propyl-1,3-dihydro-2H-benzimidazol-2-one

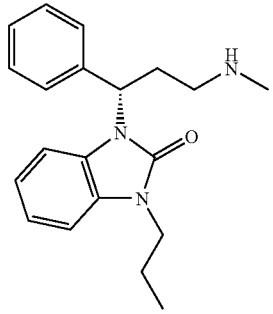

In an analogous manner to Example 14, step 2 1-propyl-1,3-dihydro-2H-benzimidazol-2-one was prepared from 1-fluoro-2-nitro-benzene and propyl amine.

MS (ES) m/z 177.1.

In an analogous manner to Example 14, step 2 1-[(1S)-3-(chloro)-1-phenylpropyl]-3-propyl-1,3-dihydro-2H-benzimidazol-2-one was prepared from 1-propyl-1,3-dihydro-2H-benzimidazol-2-one and (R)-(+)-3-chloro-1-phenyl-1-propanol.

MS (ES) m/z 329.1.

In an analogous manner to Example 14, step 3 1-[(1S)-3-(methylamino)-1-phenylpropyl]-3-propyl-1,3-dihydro-2H-benzimidazol-2-one as HCl salt was prepared from 1-[(1S)-3-(chloro)-1-phenylpropyl]-3-propyl-1,3-dihydro-2H-benzimidazol-2-one and methyl amine. $[\alpha]_D^{25}$=44.4° (c=10 mg/mL, MeOH); MS (ESI) m/z 324; HRMS: calculated for $C_{20}H_{25}N_3O+H+$, 324.20704; found (ESI, $[M+H]^+$), 324.2082.

Example 20

1-[(1R)-3-(methylamino)-1-phenylpropyl]-3-propyl-1,3-dihydro-2H-benzimidazol-2-one

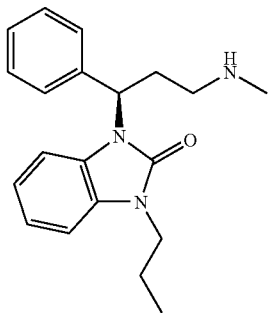

In an analogous manner to Example 14, step 2 1-[(1R)-3-(chloro)-1-phenylpropyl]-3-propyl-1,3-dihydro-2H-benzimidazol-2-one was prepared from 1-propyl-1,3-dihydro-2H-benzimidazol-2-one and (S)-(−)-3-chloro-1-phenyl-1-propanol.

MS (ES) m/z 329.1.

In an analogous manner to Example 14, step 4 1-[(1R)-3-(methylamino)-1-phenylpropyl]-3-propyl-1,3-dihydro-2H-benzimidazol-2-one as HCl salt was prepared from 1-[(1R)-3-(chloro)-1-phenylpropyl]-3-propyl-1,3-dihydro-2H-benzimidazol-2-one.

$[\alpha]_D^{25}$=+38.30 (c=10 mg/mL, MeOH); MS (ESI) m/z 324; HRMS: calculated for $C_{20}H_{25}N_3O+H^+$, 324.20704; found (ESI, $[M+H]^+$), 324.2083.

Example 21

1-[(1S)-3-(methylamino)-1-phenylpropyl]-3-phenyl-1,3-dihydro-2H-benzimidazol-2-one

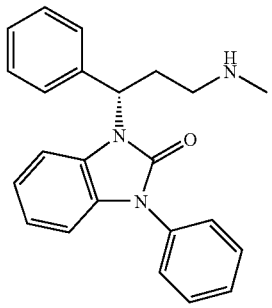

In an analogous manner to Example 14, step 1 1-phenyl-1,3-dihydro-2H-benzimidazol-2-one was prepared from 1-fluoro-2-nitro-benzene and phenyl amine.

MS (ESI) m/z 211.1.

In an analogous manner to Example 14, step 2 1-[(1S)-3-(chloro)-1-phenylpropyl]-3-phenyl-1,3-dihydro-2H-benzimidazol-2-one was prepared from 1-phenyl-1,3-dihydro-2H-benzimidazol-2-one and R(+)-3-chloro-1-phenyl-1-propanol.

MS (ESI) m/z 363.1.

In an analogous manner to Example 14, step 4 1-[(1S)-3-(methylamino)-1-phenylpropyl]-3-phenyl-1,3-dihydro-2H-benzimidazol-2-one as HCl salt was prepared from 1-[(1S)-3-(chloro)-1-phenylpropyl]-3-phenyl-1,3-dihydro-2H-benzimidazol-2-one and methyl amine. $[\alpha]_D^{25}$=47.30 (c=10 mg/mL, MeOH); MS (ES) m/z 357.9.

Example 22

1-[(1R)-3-(methylamino)-1-phenylpropyl]-3-phenyl-1,3-dihydro-2H-benzimidazol-2-one

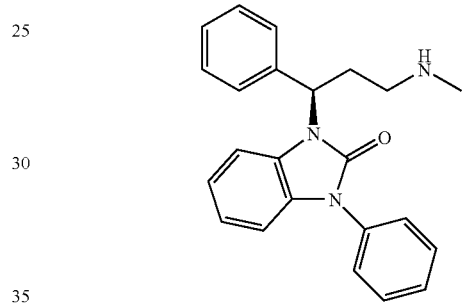

In an analogous manner to Example 14, step 2 1-[(1R)-3-(chloro)-1-phenylpropyl]-3-phenyl-1,3-dihydro-2H-benzimidazol-2-one was prepared from 1-phenyl-1,3-dihydro-2H-benzimidazol-2-one and S(−)-3-chloro-1-phenyl-1-propanol.

MS (ESI) m/z 363.1.

In an analogous manner to Example 14, step 3 1-[(1R)-3-(methylamino)-1-phenylpropyl]-3-phenyl-1,3-dihydro-2H-benzimidazol-2-one as HCl salt was prepared from 1-[(1R)-3-(chloro)-1-phenylpropyl]-3-phenyl-1,3-dihydro-2H-benzimidazol-2-one. I$[\alpha]_D^{25}$=25.9° (c=10 mg/mL, MeOH); MS (ES) m/z 357.5; HRMS: calculated for $C_{23}H_{23}N_3O+H+$, 358.19139; found (ESI, $[M+H]^+$), 358.1896.

Example 23

1-methyl-3-[(1R)-3-(methylamino)-1-phenylpropyl]-1,3-dihydro-2H-benzimidazol-2-one

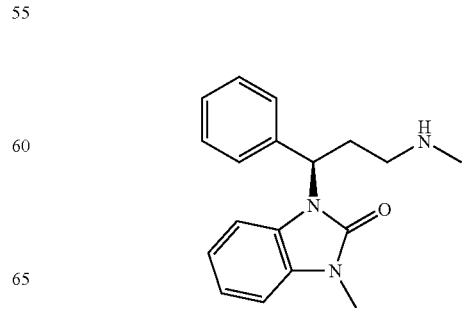

In an analogous manner to Example 14, step 2 1-methyl-3-[(1R)-3-(chloro)-1-phenylpropyl]-1,3-dihydro-2H-benzimidazol-2-one was prepared from 1-methyl-1,3-dihydro-2H-benzimidazol-2-one and S(−)-3-chloro-1-phenyl-1-propanol. MS (ES) m/z 301.2.

In an analogous manner to Example 14, step 3 1-methyl-3-[(1R)-3-(methylamino)-1-phenylpropyl]-1,3-dihydro-2H-benzimidazol-2-one as HCl salt was prepared from 1-methyl-3-[(1R)-3-(chloro)-1-phenylpropyl]-1,3-dihydro-2H-benzimidazol-2-one and methyl amine. $[\alpha]_D^{25}$=41.5° (c=10 mg/mL, MeOH); MS (ESI) m/z 296; HRMS: calculated for $C_{18}H_{21}N_3O$+H+, 296.17574; found (ESI, [M+H]+), 296.1752.

Example 24

1-cyclopentyl-3-[(1R)-3-(methylamino)-1-phenylpropyl]-1,3-dihydro-2H-benzimidazol-2-one

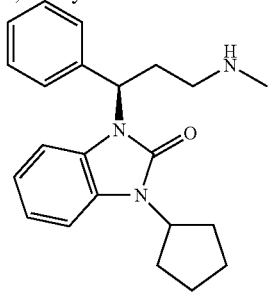

In an analogous manner to Example 14, step 2 1-cyclopentyl-1,3-dihydro-benzimidazol-2-one was prepared from 1-fluoro-2-nitro-benzene and cyclopentyl amine. MS (ESI) m/z 203.

In an analogous manner to Example 14, step 2 1-cyclopentyl-3-[(1R)-3-(chloro)-1-phenylpropyl]-1,3-dihydro-2H-benzimidazol-2-one was prepared from 1-pentyl-1,3-dihydro-2H-benzimidazol-2-one and S(−)-3-chloro-1-phenyl-1-propanol.

MS (ESI) m/z 355.2.

In an analogous manner to Example 14, step 3 1-cyclopentyl-3-[(1R)-3-(methylamino)-1-phenylpropyl]-1,3-dihydro-2H-benzimidazol-2-one as HCl salt was prepared from 1-cyclopentyl-3-[(1R)-3-(chloro)-1-phenylpropyl]-1,3-dihydro-2H-benzimidazol-2-one and methylamine. $[\alpha]_D^{25}$=30.50 (c=10 mg/mL, MeOH); MS (ES) m/z 349.9.

Example 25

1-cyclohexyl-3-[(1R)-3-(methylamino)-1-phenylpropyl]-1,3-dihydro-2H-benzimidazol-2-one

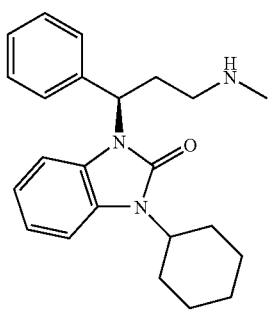

In an analogous manner to Example 14, step 1 1-cyclohexyl-1,3-dihydro-2H-benzimidazol-2-one was prepared from 1-fluoro-2-nitro-benzene and cyclohexyl amine. MS (ES) m/z 217.1.

In an analogous manner to Example 14, step 2 1-cyclohexyl-3-[(1R)-3-(chloro)-1-phenylpropyl]-1,3-dihydro-2H-benzimidazol-2-one was prepared from 1-cyclohexyl-1,3-dihydro-2H-benzimidazol-2-one and S(−)-3-chloro-1-phenyl-1-propanol.

MS (ES) m/z 369.1.

In an analogous manner to Example 14, step 3 1-cyclohexyl-3-[(1R)-3-(methylamino)-1-phenylpropyl]-1,3-dihydro-2H-benzimidazol-2-one as HCl salt was prepared from 1-cyclohexyl-3-[(1R)-3-(chloro)-I-phenylpropyl]-1,3-dihydro-2H-benzimidazol-2-one and methylamine. $[\alpha]_D^{25}$=54.5° (c=10 mg/mL, MeOH);

HRMS: calculated for $C_{23}H_{29}N_3O$+H+, 364.23834; found (ESI, [M+H]+), 364.2379.

Example 26

3-[(1R)-3-(methylamino)-1-phenylpropyl]-1,3-benzothiazol-2(3H)-one

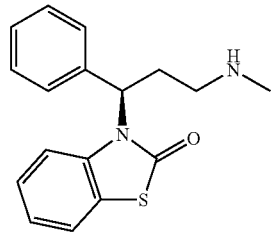

To 2-amino-benzenethiol (10 g, 79.9 mmol) in THF (200 mL) at room temperature was added carbonyldiimidazole (14.3 g, 87.9 mmol) and the reaction solution stirred for 12 hours. Upon disappearance of starting material, the reaction solution was poured into 1N HCl (125 mL) and extracted with ethyl acetate (125 mL). The organic layer was dried over sodium sulfate and concentrated to give 1,3-benzothiazol-2(3H)-one as a white solid. MS (ES) m/z 152.1.

In an analogous manner to Example 14, step 2 3-[(1R)-3-chloro-1-phenylpropyl]-1,3-benzothiazol-2(3H)-one was prepared from 1,3-benzothiazol-2(3H)-one and S(−)-3-chloro-1-phenyl-1-propanol. MS (ES) m/z 304.2; HRMS: calculated for $C_{16}H_{14}ClCOS$+H+, 304.05574; found (ESI, [M+H]+), 304.0553.

In an analogous manner to Example 14, step 3 3-[(1R)-3-(methylamino)-1-phenylpropyl]-1,3-benzothiazol-2(3H)-one was prepared from 3-[(1R)-3-chloro-1-phenylpropyl]-1,3-benzothiazol-2(3H)-one and methylamine. $[\alpha]_D^{25}$=71.5° (c=10 mg/mL, MeOH); MS (ESI) m/z 299.

Example 27

1-isopropyl-3-[(1R)-3-(methylamino)-1-phenylpropyl]-1,3-dihydro-2H-benzimidazol-2-ylidene}cyanamide

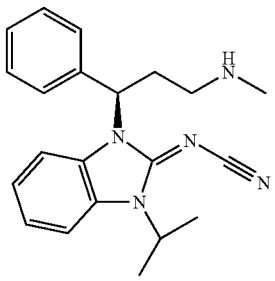

In an analogous manner to Example 14, step 1 (2E)-1-isopropyl-1.3-dihydro-2H-benzimidazol-2-ylidene]cyanamide was prepared from 1-fluoro-2-nitro-benzene and isopropyl amine. The ring closure to form (2E)-1-isopropyl-1,3-dihydro-2H-benzimidazol-2-ylidene]cyanamide was effected with diphenyl cyanocarbonimidate.

MS (ESI) m/z 201.

In an analogous manner to Example 14, step 2 1-isopropyl-3-[(1R)-3-(chloro)-1-phenylpropyl]-1,3-dihydro-2H-benzimidazol-2-ylidene}cyanamide was prepared from (2E)-1-isopropyl-1,3-dihydro-2H-benzimidazol-2-ylidene]cyanamide and S(−)-3-chloro-1-phenyl-1-propanol. MS (ES) m/z 353.2.

In an analogous manner to Example 14, step 3 1-isopropyl-3-[(1R)-3-(methylamino)-1-phenylpropyl]-1,3-dihydro-2H-benzimidazol-2-ylidene}cyanamide was prepared from 1-isopropyl-3-[(1R)-3-(chloro)-1-phenylpropyl]-1,3-dihydro-2H-benzimidazol-2-ylidene}cyanamide and methylamine. $[\alpha]_D^{25}$=+86.10 (c=10 mg/mL, MeOH); MS (ES) m/z 348.0; HRMS: calculated for $C_{21}H_{25}N_5$+H+, 348.21827; found (ESI, [M+H]+), 348.2177.

Example 28

1-[(1R)-3-amino-1-phenylpropyl]-3-ethyl-1,3-dihydro-2H-benz-imidazol-2-one

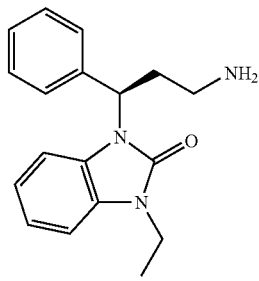

In an analogous manner to Example 14, step 3 1-[(1R)-3-amino-1-phenylpropyl]-3-ethyl-1,3-dihydro-2H-benzimidazol-2-one as HCl salt was prepared from 1-[(1R)-3-chloro-1-phenylpropyl]-3-ethyl-1,3-dihydro-2H-benzimidazol-2-one and ammonium hydroxide. MS (ES) m/z 296.0.

Example 29

1-ethyl-3-[(1R)-3-(ethylamino)-1-phenylpropyl]-1,3-dihydro-2H-benzimidazol-2-one

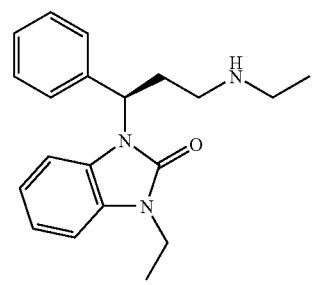

In an analogous manner to Example 14, step 3 1-ethyl-3-[(1R)-3-(ethylamino)-1-phenylpropyl1-1,3-dihydro-2H-benzimidazol-2-one as HCl salt was prepared from 1-[(1R)-3-chloro-1-phenylpropyl]-3-ethyl-1,3-dihydro-2H-benzimidazol-2-one and ethylamine. MS (ES) m/z 324.2.

Example 30

1-[(1R)-3-(dimethylamino)-1-phenylpropyl]-3-ethyl-1,3-dihydro-2H-benzimidazol-2-one

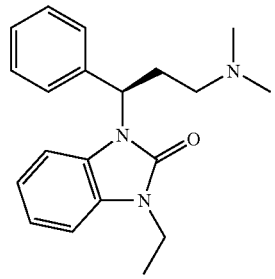

In an analogous manner to Example 14, step 3 1-[(1R)-3-(dimethylamino)-1-phenylpropyl]-3-ethyl-1,3-dihydro-2H-benzimidazol-2-one as HCl salt was prepared from 1-[(1R)-3-chloro-1-phenylpropyl]-3-ethyl-1,3-dihydro-2H-benzimidazol-2-one and dimethylamine. MS (ES) m/z 323.9.

Example 31

4-fluoro-1-isopropyl-3-[(1S)-3-(methylamino)-1-phenylpropyl]-1,3-dihydro-2H-benzimidazol-2-one

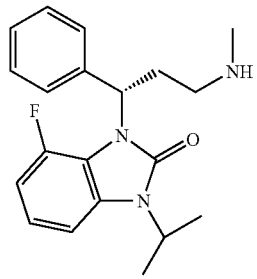

In an analogous manner to Example 14, step 1 4-fluoro-1-isopropyl-1,3-dihydro-benzoimidazol-2-one was prepared from 1,3-difluoro-2-nitro-benzeneand and isopropyl amine. MS (ES) m/z 160.

In an analogous manner to Example 14, step 2 3-[(1S)-3-chloro-1-phenyl-propyl]-4-fluoro-1-isopropyl-1,3-dihydro-benzoimidazol-2-one was prepared from 4-fluoro-1-isopropyl-1,3-dihydro-benzoimidazol-2-one and (R)-(−)-3-chloro-1-phenyl-1-propanol.

MS (ES) m/z 347.2.

In an analogous manner to Example 14, step 3 4-fluoro-1-isopropyl-3-[(1S)-3-(methylamino)-1-phenylpropyl]-1,3-dihydro-2H-benzimidazol-2-one as HCl salt was prepared from 3-[(1S)-3-chloro-1-phenyl-propyl]4-fluoro-1-isopropyl-1,3-dihydro-benzoimidazol-2-one and methylamine. $[\alpha]_D^{25}$=42.60 (c=10 mg/mL, MeOH); MS (ES) m/z 342.2.

Example 32

4-fluoro-1-isopropyl-3-[(1R)-3-(methylamino)-1-phenylpropyl]-1,3-dihydro-2H-benzimidazol-2-one

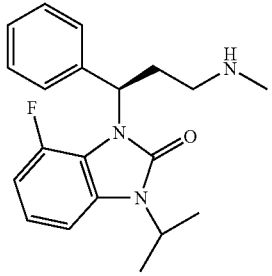

In an analogous manner to Example 14, step 2 3-[(1R)-3-chloro-1-phenyl-propyl]-4-fluoro-1-isopropyl-1,3-dihydro-benzoimidazol-2-one was prepared from 4-fluoro-1-isopropyl-1,3-dihydro-benzoimidazol-2-one and (S)-(−)-3-chloro-1-phenyl-1-propanol.

MS (ES) m/z 346.7.

In an analogous manner to Example 14, step 3 4-fluoro-1-isopropyl-3-[(1R)-3-(methylamino)-1-phenylpropyl]-1,3-dihydro-2H-benzimidazol-2-one as HCl salt was prepared from 3-[(1R)-3-chloro-1-phenyl-propyl]4-fluoro-1-isopropyl-1,3-dihydro-benzoimidazol-2-one and methylamine. $[\alpha]_D^{25}$=36.1° (c=10 mg/mL, MeOH); MS (ES) m/z 341.5; HRMS: calculated for $C_{20}H_{24}FN_3O+H+$, 342.19762; found (ESI, [M+H]+), 342.1953.

Example 33

3-[(1R)-3-(dimethylamino)-1-phenylpropyl]-4-fluoro-1-isopropyl-1,3-dihydro-2H-benzimidazol-2-one

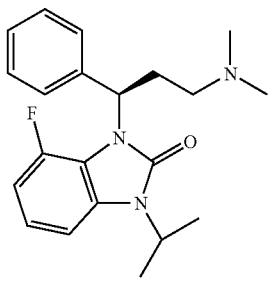

In an analogous manner to Example 14, step 3 3-[(1R)-3-(dimethylamino)-1-phenylpropyl]-4-fluoro-1-isopropyl-1,3-dihydro-2H-benzimidazol-2-one as HCl salt was prepared from 3-[(1R)-3-chloro-1-phenyl-propyl]4-fluoro-1-isopropyl-1,3-dihydro-benzoimidazol-2-one and dimethylamine. $[\alpha]_D^{25}$=32.4° (c=10 mg/mL, MeOH); MS (ES) m/z 356.0.

Example 34

{(2Z)-3-[(1R)-3-(dimethylamino)-1-phenylpropyl]-5-fluoro-1-propyl-1,3-dihydro-2H-benzimidazol-2-ylidene}cyanamide

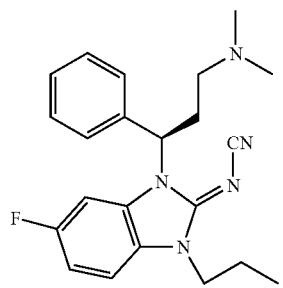

In an analogous manner to Example 14, step 1 [(2E)-5-fluoro-1-propyl-1,3-dihydro-2H-benzimidazol-2-ylidene]cyanamide was prepared from 1,4-difluoro-2-nitro-benzene and propyl amine. The ring closure to form [(2E)-5-fluoro-1-propyl-1,3-dihydro-2H-benzimidazol-2-ylidene]cyanamide was effected with diphenyl cyanocarbonimidate. MS (ES) m/z 219.3.

In an analogous manner to Example 14, step 2 {(2Z)-3-[(1R)-3-chloro-1-phenylpropyl]-5-fluoro-1-propyl-1,3-dihydro-2H-benzimidazol-2-ylidene}cyanamide was prepared from [(2E)-5-fluoro-1-propyl-1,3-dihydro-2H-benzimidazol-2-ylidene]cyanamide and (S)-(−)-3-chloro-1-phenyl-1-propanol. MS (ES) m/z 370.8.

In an analogous manner to Example 14, step 3 {(2Z)-3-[(1R)-3-(dimethylamino)-1-phenylpropyl]-5-fluoro-1-propyl-1,3-dihydro-2H-benzimidazol-2-ylidene}cyanamide was prepared from {(2Z)-3-[(1R)-3-chloro-1-phenylpropyl]-5-fluoro-1-propyl-1,3-dihydro-2H-benzimidazol-2-ylidene}cyanamide and dimethylamine. MS (ESI) m/z 380.

Moody, C. J.; Slawin, A. M. Z.; Willows, D. Org. Biomol. Chem. 2003, 1, 2716-2722.

Example 35

(3R)-3-(7-fluoro-3,3-dimethyl-2,3-dihydro-1H-indol-1-yl)-3-fluorophenyl)-N-methylpropan-1-amine hydrochloride

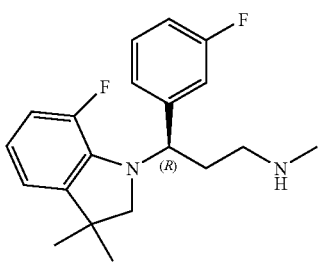

In an analogous manner to Example 12, (3R)-3-(7-fluoro-3,3-dimethyl-2,3-dihydro-1H-indol-1-yl)-3-(3-fluorophenyl)-N-methylpropan-1-amine hydrochloride was prepared from 7-fluoro-1-[(1R)-1-(3-fluorophenyl)-3-(methylamino)propyl]-3,3-dimethyl-1,3-dihydro-2H-indol-2-one (Example 5, step 9) as a white powder. MS (ES) m/z 331.0 ([M+H]$^+$); HRMS: calculated for $C_{20}H_{24}F_2N_2+H^+$, 331.1980; found (ESI, [M+H]$^+$), 331.1966.

Example 36

1-[(1R)-1-(3-chloro-5-fluorophenyl)-3-(methylamino)propyl]-7-fluoro-3,3-dimethyl-1,3-dihydro-2H-indol-2-one hydrochloride

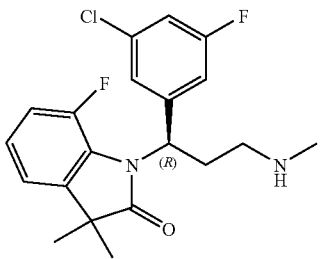

Step 1: A reaction flask (500 mL) containing zinc chloride (6.98 g, 51.2 mmol) was dried by heating using a heat gun under vacuum. After cooling to room temperature, a solution of 3-chloro-5-fluorophenylmagnesium bromide (0.5 M in dry tetrahydrofuran, 100 mL, 50.0 mmol) was added to the reaction flask via a cannula, and the mixture was stirred until all zinc chloride solid was dissolved and the formation of a sluggish bright yellow solution (~1 h). A warm bath (40° C.) may be applied to complete this process. Anhydrous tetrahydrofuran (100 mL) was added, followed by tetrakis(triphenylphosphine)palladium (2.89 g, 2.50 mmol, 0.05 equiv.). After cooling to 0° C., 3-chloropropionyl chloride (5.05 mL, 52.5 mmol, 1.05 equiv.) was added dropwise and the mixture was stirred at 0° C. for 2 h. The reaction mixture was acidified with an aqueous hydrochloric acid solution (3N), then extracted with diethyl ether (2×250 mL). The combined ether extracts were washed with a saturated aqueous sodium bicarbonate solution, brine, dried (anhydrous sodium sulfate), and concentrated. The crude oil was purified by Isco CombiFlash Companion column chromatography (silica gel, 0-15% ethyl acetate/hexane) and the resulting white solid was recrystallized (minimal diethyl ether/hexane/−25° C.) to give pure 3-chloro-1-(3-chloro-5-fluorophenyl)propan-1-one as a white powder. Yield: 5.54 g (50%).

Step 2: To a mixture of (R)-2-methyl-CBS-oxazaborolidine (1.0 M in toluene, 1.5 mL, 1.5 mmol, 0.1 equiv.) in tetrahydrofuran (10 mL) under a nitrogen atmosphere at −25° C. was added a solution of borane (1.0 M in tetrahydrofuran, 9.0 mL, 9.0 mmol, 0.6 equiv.). A solution of 3-chloro-1-(3-chloro-5-fluorophenyl)propan-1-one (3.32 g, 15.0 mmol) in tetrahydrofuran (10 mL) was added dropwise over a period of 25 min, and the reaction mixture was stirred for an additional 30 min at −25° C. Methanol (10 mL) was added slowly to quench the reaction, followed by the slow addition of hydrogen chloride solution (1.0 M in diethyl ether, 20 mL) at −25° C. All volatiles were removed under reduced pressure. Hexane (100 mL) was added, and the white salt of the chiral auxiliary was filtered through a pad of celite and washed with hexane (2×25 mL). The filtrate was concentrated under reduced pressure to give (1S)-3-chloro-1-(3-chloro-5-fluorophenyl)propan-1-ol as viscous, colorless oil. Yield: 3.34 g (100%). Chiral purity: 93.4%. This material was dissolved in 70 mL of methanol/acetonitrile. 500 □L of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H 5□m, 250 mm×4.6 mm ID column at 2.0 mL/min flow rate using Analytical Supercritical Fluid Chromatography (Berger Instruments, Inc. Newark, Del.). The chiral purity of the product was found to be 99.8%.

SFC Instrument: Berger MultiGram Prep SFC (Berger Instruments, Inc. Newark, Del.)

Column: Chiralpak AD-H; 5□m; 250 mm L×20 mm ID (Chiral Technologies, Inc, Exton, Pa.)

Column temperature: 35° C.

SFC Modifier: 20% MeOH/80% $CO_2$

Flow rate: 50 mL/min

Outlet Pressure: 100 bar

Detector: UV at 220 nm

Step 3: In an analogous manner to Example 9, step 1, 1-[(1R)-3-chloro-1-(3-chloro-5-fluorophenyl)propyl]-7-fluoro-3,3-dimethyl-1,3-dihydro-2H-indol-2-one was prepared from 7-fluoro-3,3-dimethyl-1,3-dihydro-2H-indol-2-one (Example 5, step 4) and (1S)-3-chloro-1-(3-chloro-5-fluorophenyl)propan-1-ol as a viscous, colorless liquid. MS (ES) m/z 383.9 ([M+H]$^+$); HRMS: calculated for $C_{19}H_{17}Cl_2F_2NO +H^+$, 384.0728; found (ESI, [M+H]$^+$), 384.0721.

Step 4: In an analogous manner to Example 9, step 2, 1-[(1R)-1-(3-chloro-5-fluorophenyl)-3-(methylamino)propyl]-7-fluoro-3,3-dimethyl-1,3-dihydro-2H-indol-2-one hydrochloride was prepared from 1-[(1R)-3-chloro-1-(3-chloro-5-fluorophenyl)propyl]-7-fluoro-3,3-dimethyl-1,3-dihydro-2H-indol-2-one as a white powder. MS (ES) m/z 379.0 ([M+H]$^+$); HRMS: calculated for $C_{20}H_{21}Cl_2F_2N_2O+ H^+$, 379.1383; found (ESI, [M+H]$^+$), 379.1360.

Example 37

1-[(1R)-1-(3,5-difluorophenyl)-3-(methylamino)propyl]-7-fluoro-3,3-dimethyl-1,3-dihydro-2H-indol-2-one hydrochloride

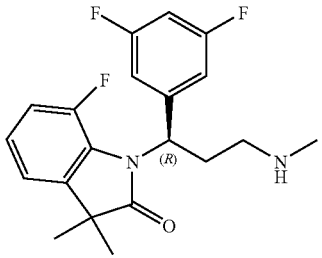

In an analogous manner to Example 36, step 1,3-chloro-1-(3,5-difluorophenyl)propan-1-one was prepared from 3,5-difluorophenylmagnesium bromide as a white solid. MS (ES) m/z 205.1 ([M+H]$^+$).

In an analogous manner to Example 36, step 2, (1S)-3-chloro-1-(3,5-difluorophenyl)propan-1-ol was prepared from 3-chloro-1-(3,5-difluorophenyl)propan-1-one as viscous, colorless oil. Chiral purity: 91.4%.

In an analogous manner to Example 9, step 1, 1-[(1R)-3-chloro-1-(3,5-difluorophenyl)propyl-]-7-fluoro-3,3-dimethyl-1,3-dihydro-2H-indol-2-one was prepared from 7-fluoro-3,3-dimethyl-1,3-dihydro-2H-indol-2-one (Example 5, step 4) and (1S)-3-chloro-1-(3,5-difluorophenyl)propan-1-ol as a viscous, colorless liquid.

MS (ES) m/z 367.8 ([M+H]$^+$).

In an analogous manner to Example 9, step 2, 1-[(1R)-1-(3,5-difluorophenyl)-3-(methylamino)propyl]-7-fluoro-3,3-dimethyl-1,3-dihydro-2H-indol-2-one hydrochloride was prepared from 1-[(1R)-3-chloro-1-(3,5-difluorophenyl)propyl]-7-fluoro-3,3-dimethyl-1,3-dihydro-2H-indol-2-one as a white powder. MS (ES) m/z 363.1 ([M+H]$^+$).

Example 38

1-[(1R)-1-(3-chlorophenyl)-3-(methylamino)propyl]-7-fluoro-3,3-dimethyl-1.3-dihydro-2H-indol-2-one hydrochloride

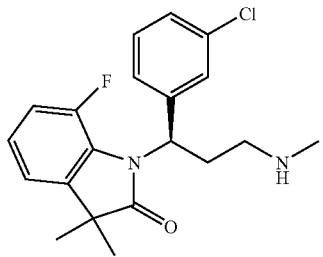

Step 1: In an analogous manner to Example 9, step 1, 1-[(1R)-3-chloro-1-(3-chlorophenyl)propyl]-7-fluoro-3,3-dimethyl-1,3-dihydro-2H-indol-2-one was prepared from 7-fluoro-3,3-dimethyloxindole (example 5, steps 1-4) and (S)-3-Chloro-1-(3-chloro-phenyl)-propanol as a viscous, yellow liquid. MS (ES) MS (ES) m/z 365.9. ([M+H]$^+$).

Step 2: In an analogous manner to Example 9, step 2, 1-[(1R)-1-(3-chlorophenyl)-3-(methylamino)propyl]-7-fluoro-3,3-dimethyl-1,3-dihydro-2H-indol-2-one hydrochloride was prepared from 1-[(1R)-3-chloro-1-(3-chlorophenyl)propyl]-7-fluoro-3,3-dimethyl-1,3-dihydro-2H-indol-2-one as a white powder. MS (ES) m/z 361.0. ([M+H]$^+$); HRMS: calculated for $C_{20}H_{22}ClFN_2O+H^+$, 361.14774; found (ESI, [M+H]$^+$), 361.1361.

Example 39

4-fluoro-1-(2-fluorophenyl)-3-[(1R)-3-(methylamino)-1-phenylpropyl]-1,3-dihydro-2H-benzimidazol-2-one

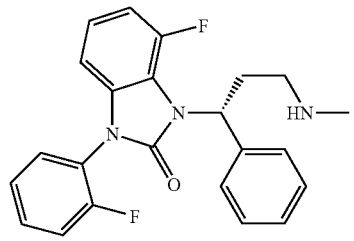

Step 1: To 2-fluoroaniline (1.55 g, 13.9 mmol) in anhydrous dimethylformamide (10 mL) was added sodium hydride (0.56 g, 13.9 mmol) and the reaction stirred for 10 minutes prior to the addition of 2,6-difluoronitrobenzene (2 g, 15.5 mmol) dissolved in anhydrous dimethylformamide (2 mL). Upon disappearance of 2-fluoroaniline the reaction was partitioned between saturated ammonium chloride (50 mL) and ethyl acetate (50 mL) and the organics were dried over sodium sulfate. The product was purified on silica gel using the ISCO (0-70% ethyl acetate/hexane) to give (3-Fluoro-2-nitro-phenyl)-(2-fluoro-phenyl)-amine as a slightly impure off-white solid (1.5 g, 43%). (3-Fluoro-2-nitro-phenyl)-(2-fluoro-phenyl)-amine (1.5 g, 6 mmol) and a spatula tip of 5% Pd/C in methanol (100 mL) were reduced in the parr shaker. Upon complete reduction, the reaction was filtered through a pad of celite and concentrated onto silica gel. The product was purified on silica gel using the ISCO (0-70% ethyl acetate/hexane) to give 3-fluoro-N1-(2-fluorophenyl)benzene-1,2-diamine as a brown oil (0.5 g, 38%). MS (ES) m/z 221.1

Step 2: 3-fluoro-N1-(2-fluorophenyl)benzene-1,2-diamine (0.44 g, 2 mmol) and carbonyl diimidazole (0.29 g, 1.8 mmol) in tetrahydrofuran (10 mL) was stirred at room temperature overnight. Upon disappearance of the starting material, the reaction was partitioned between 1 N hydrochloric acid (100 mL) and ethyl acetate (100 mL). The organics were dried over sodium sulfate and concentrated to give 4-fluoro-1-(2-fluorophenyl)-1,3-dihydro-2H-benzimidazol-2-one as a white solid in near quantitative yield. MS (ES) m/z 247.0

Step 3: In an analogous manner to Example 14 step 2, 3-[(1R)-3-chloro-1-phenylpropyl]-4-fluoro-1-(2-fluorophenyl)-1,3-dihydro-2H-benzimidazol-2-one was prepared from 4-fluoro-1-(2-fluorophenyl)-1,3-dihydro-2H-benzimidazol-2-one and (S)-(–)-3-chloro-1-phenyl-1-propanol. MS (ES) m/z 398.9

Step 4: In an analogous manner to Example 14 step 3, 4-fluoro-1-(2-fluorophenyl)-3-[(1R)-3-(methylamino)-1-phenylpropyl]-1,3-dihydro-2H-benzimidazol-2-one hydrochloride salt as a white solid was prepared from 3-[(1R)-3-chloro-1-phenylpropyl]-4-fluoro-1-(2-fluorophenyl)-1,3-dihydro-2H-benzimidazol-2-one.

$[\alpha]_D^{25}$=34.3° (c=10 mg/mL, MeOH); MS (ES) m/z 394.0; HRMS: calculated for C23H21F2N3O+H+, 394.17254; found (ESI, [M+H]$^+$), 394.1727

Example 40

1-ethyl-4-fluoro-3-[(1R)-1-(3-fluorophenyl)-3-(methylamino)propyl]-1,3-dihydro-2H-benzimidazol-2-one

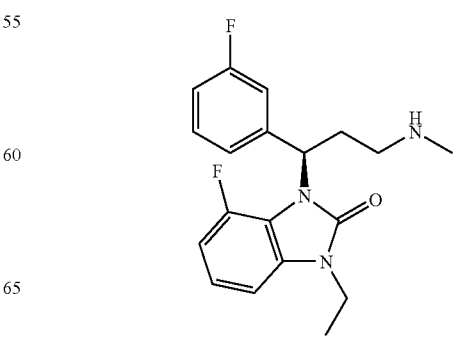

Step 1: To 2,6-difluoroaniline (8 g, 62 mmol) in dimethylformamide (100 mL) was added a 2 M solution in tetrahydrofuran of ethyl amine (93 mL, 186 mmol) and the reaction stirred at room temperature overnight. The reaction was partitioned between 1 N hydrochloric acid and ethyl acetate and dried over sodium sulfate. The product was purified by silica gel using the ISCO (0-100% ethyl acetate/hexane) to give an equal mixture of ethyl-(3-fluoro-2-nitro-phenyl)-amine and N,N'-Diethyl-2-nitro-benzene-1,3-diamine. This mixture was reduced using the parr shaker and a spatula tip of 5% Pd/C in MeOH (100 mL). Upon complete reduction, the reaction was filtered through a pad of celite and concentrated onto silica gel. The desired product was purified on silica gel using the ISCO (0-100% ethyl acetate/hexane) to give $N^1$-Ethyl-3-fluoro-benzene-1,2-diamine (2.48 g, 52%). $N^1$-Ethyl-3-fluoro-benzene-1,2-diamine (2.48 g, 16.1 mmol) and carbonyl diimidazole (4.38 g, 27 mmol) in tetrahydrofuran (50 mL) was stirred at room temperature overnight. Upon disappearance of the starting material, the reaction was partitioned between 1 N hydrochloric acid (100 mL) and ethyl acetate (100 mL). The organics were dried over sodium sulfate and concentrated to give 1-ethyl-4-fluoro-1,3-dihydro-2H-benzimidazol-2-one as a white solid in near quantitative yield. MS (ES) m/z 181.1;

HRMS: calculated for $C_9H_9FN_2O+H+$, 181.07717; found (ESI, [M+H]+), 181.076

Step 2: In an analogous manner to Example 14 step 2, 3-[(1R)-3-chloro-1-(3-fluorophenyl)propyl]-1-ethyl-4-fluoro-1,3-dihydro-2H-benzimidazol-2-one was prepared from 1-ethyl-4-fluoro-1,3-dihydro-2H-benzimidazol-2-one and (1S)-3-chloro-1-(3-fluorophenyl)propan-1-ol. MS (ES) m/z 351.0

Step 3: In an analogous manner to Example 14 step 3, 1-ethyl-4-fluoro-3-[(1R)-1-(3-fluorophenyl)-3-(methylamino)propyl]-1,3-dihydro-2H-benzimidazol-2-one hydrochloride salt was prepared from 3-[(1R)-3-chloro-1-(3-fluorophenyl)propyl]-1-ethyl-4-fluoro-1,3-dihydro-2H-benzimidazol-2-one $[\alpha]_D^{25}$=28.3° (c=10 mg/mL, MeOH);
MS (ES) m/z 346.1; HRMS: calculated for $C_{19}H_{21}F_2N_3O+$ H+, 346.17254; found (ESI, [M+H]+), 346.1707

Cell Lines, Culture Reagents, and Assays

MDCK-Net6 cells, stably transfected with human hNET (Pacholczyk, T., R. D. Blakely, and S. G. Amara, *Nature*, 1991,350(6316): p. 350-4) were cultured in growth medium containing high glucose DMEM (Gibco, Cat. No. 11995), 10% FBS (dialyzed, heat-inactivated, US Bio-Technologies, Lot FBD1129HI) and 500 µg/ml G418 (Gibco, Cat. No. 10131). Cells were plated at 300,000/T75 flask and cells were split twice weekly. The JAR cell line (human placental choriocarcinoma) was purchased from ATCC (Cat. No. HTB-144). The cells were cultured in growth medium containing RPMI 1640 (Gibco, Cat. No. 72400), 10% FBS (Irvine, Cat. No. 3000), 1% sodium pyruvate (Gibco, Cat. No. 1136) and 0.25% glucose. Cells were plated at 250,000 cells/T75 flask and split twice weekly. For all assays, cells were plated in Wallac 96-well sterile plates (PerkinElmer, Cat. No. 3983498).

Norepinephrine (NE) Uptake Assay

On day 1, cells were plated at 3,000 cells/well in growth medium and maintained in a cell incubator (37° C., 5% $CO_2$). On day 2, growth medium was replaced with 200 µl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 µM pargyline. Plates containing cells with 200 µl of assay buffer were equilibrated for 10 minutes at 37° C. prior to addition of compounds. A stock solution of desipramine was prepared in DMSO (10 mM) and delivered to triplicate wells containing cells for a final test concentration of 1 µM. Data from these wells were used to define non-specific NE uptake (minimum NE uptake). Test compounds were prepared in DMSO (10 mM) and diluted in assay buffer according to test range (1 to 10,000 nM). Twenty-five microliters of assay buffer (maximum NE uptake) or test compound were added directly to triplicate wells containing cells in 200 µl of assay buffer. The cells in assay buffer with test compounds were incubated for 20 minutes at 37° C. To initiate the NE uptake, [$^3$H]NE diluted in assay buffer (120 nM final assay concentration) was delivered in 25 µl aliquots to each well and the plates were incubated for 5 minutes (37° C.). The reaction was terminated by decanting the supernatant from the plate. The plates containing cells were washed twice with 200 µl assay buffer (37° C.) to remove free radioligand. The plates were then inverted, left to dry for 2 minutes, then reinverted and air-dried for an additional 10 minutes. The cells were lysed in 25 µl of 0.25N NaOH solution (4° C.), placed on a shake table and vigorously shaken for 5 minutes. After cell lysis, 75 µl of scintillation cocktail was added to each well and the plates were sealed with film tape. The plates were returned to the shake table and vigorously shaken for a minimum of 10 minutes to ensure adequate partitioning of organic and aqueous solutions. The plates were counted in a Wallac Microbeta counter (PerkinElmer) to collect the raw cpm data.

Serotonin (5-HT) Uptake Assay

The methods for 5-HT functional reuptake using the JAR cell line were modified using a previous literature report (Prasad, et al., *Placenta*, 1996. 17(4): 201-7). On day 1, cells were plated at 15,000 cells/well in 96-well plates containing growth medium (RPMI 1640 with 10% FBS) and maintained in a cell incubator (37° C., 5% $CO_2$). On day 2, cells were stimulated with staurosporine (40 nM) to increase the expression of the 5-HT transporter [17]. On day 3, cells were removed from the cell incubator two hours prior to assay and maintained at room temperature to equilibrate the growth medium to ambient oxygen concentration. Subsequently, the growth medium was replaced with 200 µl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 µM pargyline. A stock solution of paroxetine (AHR-4389-1) was prepared in DMSO (10 mM) and delivered to triplicate wells containing cells for a final test concentration of 1 µM. Data from these wells were used to define non-specific 5-HT uptake (minimum 5-HT uptake). Test compounds were prepared in DMSO (10 mM) and diluted in assay buffer according to test range (1 to 1,000 nM). Twenty-five microliters of assay buffer (maximum 5-HT uptake) or test compound were added directly to triplicate wells containing cells in 200 µl of assay buffer. The cells were incubated with the compound for 10 minutes (37° C.). To initiate the reaction, [$^3$H]hydroxytryptamine creatinine sulfate diluted in assay buffer was delivered in 25 µl aliquots to each well for a final test concentration of 15 nM. The cells were incubated with the reaction mixture for 5 minutes at 37° C. The 5-HT uptake reaction was terminated by decanting the assay buffer. The cells were washed twice with 200 µl assay buffer (37° C.) to remove free radioligand. The plates were inverted and left to dry for 2 minutes, then reinverted and air-dried for an additional 10 minutes. Subsequently, the cells were lysed in 25 µl of 0.25N NaOH (4° C.) then placed on a shaker table and shaken vigorously for 5 minutes. After cell lysis, 75 μl of scintillation cocktail was added to the wells, the plates were sealed with film tape and replaced on the shake table for a minimum of 10 minutes. The plates were counted in a Wallac Microbeta counter (PerkinElmer) to collect the raw cpm data.

Evaluation of Results

For each experiment, a data stream of cpm values collected from the Wallac Microbeta counter was downloaded to a Microsoft Excel statistical application program. Calculations of $EC_{50}$ values were made using the transformed-both-sides logistic dose response program written by Wyeth Biometrics Department. The statistical program uses mean cpm values from wells representing maximum binding or uptake (assay buffer) and mean cpm values from wells representing minimum binding or uptake ((1 μM desipramine (hNET) or 1 μM paroxetine (hSERT)). Estimation of the $EC_{50}$ value was completed on a log scale and the line was fit between the maximum and minimum binding or uptake values. All graphic data representation was generated by normalizing each data point to a mean percent based on the maximum and minimum binding or uptake values. The $EC_{50}$ values reported from multiple experiments were calculated by pooling the raw data from each experiment and analyzing the pooled data as one experiment.

The compounds of formula I are expected to have a $IC_{50}$ (NET) of less than about 10 μM.

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I:

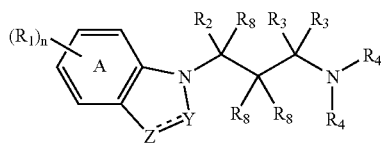

or a pharmaceutically acceptable salt thereof;
wherein:
Y is $C(R_3)_2$, C=O, or C=N—C=N;
Z is S, O, $NR_6$, or $C(R_5)_2$;
n is an integer from 0 to 4;
$R_1$ is, independently at each occurrence, alkyl, alkoxy, halo, $CF_3$, $OCF_3$, arylalkyloxy substituted with 0 to 3 $R_7$, aryloxy substituted with 0 to 3 $R_7$, aryl substituted with 0 to 3 $R_7$, heteroaryl substituted with 0 to 3 $R_7$, hydroxy, alkanoyloxy, nitro, cyano, alkenyl, alkynyl, alkylsulfoxide, phenylsulfoxide substituted with 0 to 3 $R_7$, alkylsulfone, phenylsulfone substituted with 0 to 3 $R_7$, alkylsulfonamide, phenylsulfonamide substituted with 0 to 3 $R_7$, heteroaryloxy substituted with 0 to 3 $R_7$, heteroarylmethyloxy substituted with 0 to 3 $R_7$, alkylamido, or arylamido substituted with 0 to 3 $R_7$;
$R_2$ is aryl substituted with 0 to 3 $R_1$ or heteroaryl substituted with 0 to 3 $R_1$;
$R_3$ is, independently at each occurrence, H or $C_1$ to $C_4$ alkyl;
$R_4$ is, independently at each occurrence, H, $C_1$ to $C_4$ alkyl, arylalkyl, heteroarylmethyl, or cyclobutylmethyl cycloheptylmethyl, cyclohexylmethyl, cyclopentylmethyl, or cyclobutylmethyl;
$R_5$ is, independently, $C_1$ to $C_4$ alkyl, $C_3$ to $C_6$ branched alkyl, $C_3$ to $C_6$ cycloalkyl, aryl substituted with 0 to 3 $R_1$; or heteroaryl substituted with 0 to 3 $R_1$; or two $R_5$, together with the carbon through which they are attached, form a carbocyclic ring of 3 to 7 carbons;
$R_6$ is H, $C_1$ to $C_6$ alkyl, $C_3$ to $C_6$ branched alkyl, $C_3$ to $C_6$ cycloalkyl, aryl substituted with 0 to 3 $R_1$, or heteroaryl substituted with 0 to 3 $R_1$;
$R_7$ is, independently at each occurrence, alkyl, alkoxy, halo, $CF_3$, $OCF_3$, hydroxy, alkanoyloxy, nitro, cyano, alkenyl, alkynyl, alkylsulfoxide, alkylsulfone, alkylsulfonamide, or alkylamido;
$R_8$ is, independently at each occurrence, H, F, $C_1$ to $C_6$ alkyl, $C_3$ to $C_6$ branched alkyl, or $C_3$ to $C_6$ cycloalkyl; and
wherein 1 to 3 carbon atoms in ring A may optionally be replaced with N.

2. A compound according to claim 1, wherein: Y is $C(R_3)_2$, C=O, or C=N—C=N.

3. A compound according to claim 1, wherein: Y is $CH_2$, C=O, or C=N—C=N.

4. A compound according to claim 1, wherein: Z is $NR_6$ or $C(R_5)_2$.

5. A compound according to claim 1, wherein: n is an integer from 0 to 2.

6. A compound according to claim 1, wherein: n is an integer from 0 to 1.

7. A compound according to claim 1, wherein: $R_1$ is, independently at each occurrence, alkyl, alkoxy, halo, $CF_3$, $OCF_3$, aryl substituted with 0 to 3 $R_7$, heteroaryl substituted with 0 to 3 $R_7$, hydroxy, alkanoyloxy, nitro, or cyano.

8. A compound according to claim 1, wherein: $R_1$ is, independently at each occurrence, alkyl or halo.

9. A compound according to claim 1, wherein: $R_1$ is, independently at each occurrence, halo.

10. A compound according to claim 1, wherein: $R_1$ is, independently at each occurrence, fluoro.

11. A compound according to claim 1, wherein: $R_2$ is aryl substituted with 0 to 3 $R_1$.

12. A compound according to claim 1, wherein: $R_2$ is phenyl or halo-substituted aryl.

13. A compound according to claim 1, wherein: $R_2$ is phenyl or fluoro-substituted aryl.

14. A compound according to claim 1, wherein: $R_2$ is heteroaryl substituted with 0 to 3 $R_1$.

15. A compound according to claim 1, wherein: $R_3$ is, independently at each occurrence, H or $C_1$ to $C_2$ alkyl.

16. A compound according to claim 1, wherein: $R_3$ is H.

17. A compound according to claim 1, wherein: $R_4$ is, independently at each occurrence, H, $C_1$ to $C_4$ alkyl, arylalkyl, heteroarylmethyl, cycloheptylmethyl, cyclohexylmethyl, cyclopentylmethyl, or cyclobutylmethyl.

18. A compound according to claim 1, wherein: $R_4$ is, independently at each occurrence, H or $C_1$ to $C_4$ alkyl.

19. A compound according to claim 1, wherein: $R_4$ is, independently at each occurrence, H, methyl, or ethyl.

20. A compound according to claim 1, wherein: both $R_4$ are H.

21. A compound according to claim 1, wherein: both $R_4$ are methyl.

22. A compound according to claim 1, wherein: one $R_4$ is H and the other $R_4$ is methyl or ethyl.

23. A compound according to claim 1, wherein:
$R_5$ is, independently, H, $C_1$ to $C_4$ alkyl, $C_3$ to $C_6$ branched alkyl, $C_3$ to $C_6$ cycloalkyl, aryl substituted with 0 to 3 $R_1$; or heteroaryl substituted with 0 to 3 $R_1$.

24. A compound according to claim 1, wherein:
$R_5$ is, independently, H or $C_1$ to $C_4$ alkyl.

25. A compound according to claim 1, wherein:
$R_5$ is, independently, H or methyl.

26. A compound according to claim 1, wherein: two $R_5$, together with the carbon through which they are attached, form a carbocyclic ring of 3 to 7 carbons.

27. A compound according to claim 1, wherein:
$R_6$ is H, $C_1$ to $C_6$ alkyl, $C_3$ to $C_6$ branched alkyl, $C_3$ to $C_6$ cycloalkyl, aryl, or heteroaryl.

28. A compound according to claim 1, wherein:
$R_6$ is H, $C_1$ to $C_4$ alkyl, $C_3$ to $C_6$ branched alkyl, $C_3$ to $C_6$ cycloalkyl, aryl, or heteroaryl.

29. A compound according to claim 1, wherein:
$R_6$ is H, methyl, ethyl, n-propyl, isopropyl, cyclopropyl, cyclopentyl, cyclohexyl, or phenyl.

30. A compound according to claim 1, wherein:
$R_7$ is, independently at each occurrence, alkyl, alkoxy, halo, $CF_3$, $OCF_3$, hydroxy, alkanoyloxy, nitro, or cyano.

31. A compound according to claim 1, wherein: $R_8$ is, independently at each occurrence, H, F, or $C_1$ to $C_6$ alkyl.

32. A compound according to claim 1, wherein: $R_8$ is H.

33. A compound according to claim 1, wherein:
1 to 3 carbon atoms in ring A are replaced with N.

34. A compound according to claim 1 of the formula:

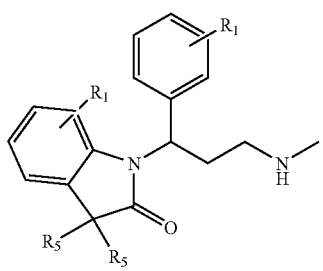

or a pharmaceutically acceptable salt thereof;
wherein:
$R_1$ is, independently at each occurrence, H, halo, hydroxyl, cyano, alkoxy, or $C_1$ to $C_6$ alkyl;
$R_5$ is, independently at each occurrence, $C_1$ to $C_6$ alkyl; or two $R_5$, together with the carbon through which they are attached, form a carbocyclic ring of 3 to 7 carbons.

35. A compound according to claim 1 of the formula:

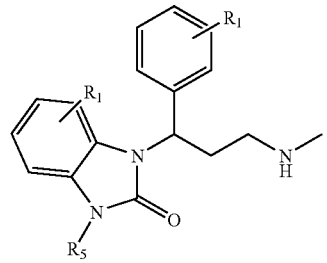

or a pharmaceutically acceptable salt thereof;
wherein:
$R_1$ is, independently at each occurrence, H, halo, hydroxyl, cyano, alkoxy, or $C_1$ to $C_6$ alkyl;
$R_5$ is $C_1$ to $C_4$ alkyl, $C_3$ to $C_6$ branched alkyl, $C_3$ to $C_6$ cycloalkyl, or aryl substituted with 0 to 3 $R_1$.

36. A compound according to claim 1, wherein said compound is:
1'-[3-(methylamino)-1-phenylpropyl]spiro[cyclohexane-1,3'-indol]-2'(1'H)-one;
1'-[1-(3-fluorophenyl)-3-(methylamino)propyl]spiro[cyclohexane-1,3'-indol]-2'(1'H)-one;
7-fluoro-1-[1-(3-fluorophenyl)-3-(methylamino)propyl]-3,3-dimethyl-1,3-dihydro-2H-indol-2-one;
3,3-dimethyl-1-[3-(methylamino)-1-phenylpropyl]-1,3-dihydro-2H-indol-2-one;
7-fluoro-3,3-dimethyl-1-[3-(methylamino)-1-phenylpropyl]-1,3-dihydro-2H-indol-2-one;
3-(3,3-dimethyl-2,3-dihydro-1H-indol-1-yl)-N-methyl-3-phenylpropan-1-amine;
3-(7-fluoro-3,3-dimethyl-2,3-dihydro-1H-indol-1-yl)-N-methyl-3-phenylpropan-1-amine;
1-ethyl-3-[3-(methylamino)-1-phenylpropyl]-1,3-dihydro-2H-benzimidazol-2-one;
1-cyclopropyl-3-[3-(methylamino)-1-phenylpropyl]-1,3-dihydro-2H-benzimidazol-2-one;
1-isopropyl-3-[3-(methylamino)-1-phenylpropyl]-1,3-dihydro-2H-benzimidazol-2-one;
1-[3-(methylamino)-1-phenylpropyl]-3-propyl-1,3-dihydro-2H-benzimidazol-2-one;
1-[3-(methylamino)-1-phenylpropyl]-3-propyl-1,3-dihydro-2H-benzimidazol-2-one;
1-methyl-3-[3-(methylamino)-1-phenylpropyl]-1,3-dihydro-2H-benzimidazol-2-one;
1-cyclopentyl-3-[3-(methylamino)-1-phenylpropyl]-1,3-dihydro-2H-benzimidazol-2-one;
1-cyclohexyl-3-[3-(methylamino)-1-phenylpropyl]-1,3-dihydro-2H-benzimidazol-2-one;
3-[3-(methylamino)-1-phenylpropyl]-1,3-benzothiazol-2(3H)-one;
1-isopropyl-3-[3-(methylamino)-1-phenylpropyl]-1,3-dihydro-2H-benzimidazol-2-ylidene}cyanamide;
1-[3-amino-1-phenylpropyl]-3-ethyl-1,3-dihydro-2H-benz-imidazol-2-one;
1-ethyl-3-[3-(ethylamino)-1-phenylpropyl]-1,3-dihydro-2H-benzimidazol-2-one;
1-[3-(dimethylamino)-1-phenylpropyl]-3-ethyl-1,3-dihydro-2H-benzimidazol-2-one;
4-fluoro-1-isopropyl-3-[3-(methylamino)-1-phenylpropyl]-1,3-dihydro-2H-benzimidazol-2-one;
3-[3-(dimethylamino)-1-phenylpropyl]-4-fluoro-1-isopropyl-1,3-dihydro-2H-benzimidazol-2-one;

{(2Z)-3-[3-(dimethylamino)-1-phenylpropyl]-5-fluoro-1-propyl-1,3-dihydro-2H-benzimidazol-2-ylidene}cyanamide;
3-(7-fluoro-3,3-dimethyl-2,3-dihydro-1H-indol-1-yl)-3-(3-fluorophenyl)-N-methylpropan-1-amine;
1-[1-(3-chloro-5-fluorophenyl)-3-(methylamino)propyl]-7-fluoro-3,3-dimethyl-1,3-dihydro-2H-indol-2-one;
1-[1-(3,5-difluorophenyl)-3-(methylamino)propyl]-7-fluoro-3,3-dimethyl-1,3-dihydro-2H-indol-2-one;
1-[1-(3-chlorophenyl)-3-(methylamino)propyl]-7-fluoro-3,3-dimethyl-1,3-dihydro-2H-indol-2-one;
4-fluoro-1-(2-fluorophenyl)-3-[3-(methylamino)-1-phenylpropyl]-1,3-dihydro-2H-benzimidazol-2-one;
1-ethyl-4-fluoro-3-[1-(3-fluorophenyl)-3-(methylamino)propyl]-1,3-dihydro-2H-benzimidazol-2-one; or
a pharmaceutically acceptable salt thereof.

37. A compound according to claim 1, wherein said compound is:
   1'-[(1R)-3-(methylamino)-1-phenylpropyl]spiro[cyclohexane-1,3'-indol]-2'(1'H)-one;
   1'-[(1S)-3-(methylamino)-1-phenylpropyl]spiro[cyclohexane-1,3'-indol]-2'(1'H)-one;
   1'-[(1R)-1-(3-fluorophenyl)-3-(methylamino)propyl]spiro[cyclohexane-1,3'-indol]-2'(1'H)-one;
   1'-[(1S)-1-(3-fluorophenyl)-3-(methylamino)propyl]spiro[cyclohexane-1,3'-indol]-2'(1'H)-one;
   7-fluoro-1-[(1R)-1-(3-fluorophenyl)-3-(methylamino)propyl]-3,3-dimethyl-1,3-dihydro-2H-indol-2-one;
   7-fluoro-1-[(1S)-1-(3-fluorophenyl)-3-(methylamino)propyl]-3,3-dimethyl-1,3-dihydro-2H-indol-2-one;
   3,3-dimethyl-1-[(1S)-3-(methylamino)-1-phenylpropyl]-1,3-dihydro-2H-indol-2-one;
   3,3-dimethyl-1-[(1R)-3-(methylamino)-1-phenylpropyl]-1,3-dihydro-2H-indol-2-one;
   3,3-dimethyl-1-[(1R)-3-(methylamino)-1-phenylpropyl]-1,3-dihydro-2H-indol-2-one;
   3,3-dimethyl-1-[(1S)-3-(methylamino)-1-phenylpropyl]-1,3-dihydro-2H-indol-2-one;
   7-fluoro-3,3-dimethyl-1-[(1R)-3-(methylamino)-1-phenylpropyl]-1,3-dihydro-2H-indol-2-one;
   (3R)-3-(3,3-dimethyl-2,3-dihydro-1H-indol-1-yl)-N-methyl-3-phenylpropan-1-amine;
   (3R)-3-(7-fluoro-3,3-dimethyl-2,3-dihydro-1H-indol-1-yl)-N-methyl-3-phenylpropan-1-amine;
   1-ethyl-3-[(1R)-3-(methylamino)-1-phenylpropyl]-1,3-dihydro-2H-benzimidazol-2-one;
   1-cyclopropyl-3-[(1S)-3-(methylamino)-1-phenylpropyl]-1,3-dihydro-2H-benzimidazol-2-one;
   1-cyclopropyl-3-[(1R)-3-(methylamino)-1-phenylpropyl]-1,3-dihydro-2H-benzimidazol-2-one;
   1-isopropyl-3-[(1S)-3-(methylamino)-1-phenylpropyl]-1,3-dihydro-2H-benzimidazol-2-one;
   1-isopropyl-3-[(1R)-3-(methylamino)-1-phenylpropyl]-1,3-dihydro-2H-benzimidazol-2-one;
   1-[(1S)-3-(methylamino)-1-phenylpropyl]-3-propyl-1,3-dihydro-2H-benzimidazol-2-one;
   1-[(1R)-3-(methylamino)-1-phenylpropyl]-3-propyl-1,3-dihydro-2H-benzimidazol-2-one;
   1-[(1S)-3-(methylamino)-1-phenylpropyl]-3-phenyl-1,3-dihydro-2H-benzimidazol-2-one;
   1-[(1R)-3-(methylamino)-1-phenylpropyl]-3-phenyl-1,3-dihydro-2H-benzimidazol-2-one;
   1-methyl-3-[(1R)-3-(methylamino)-1-phenylpropyl]-1,3-dihydro-2H-benzimidazol-2-one;
   1-cyclopentyl-3-[(1R)-3-(methylamino)-1-phenylpropyl]-1,3-dihydro-2H-benzimidazol-2-one;
   1-cyclohexyl-3-[(1R)-3-(methylamino)-1-phenylpropyl]-1,3-dihydro-2H-benzimidazol-2-one;
   3-[(1R)-3-(methylamino)-1-phenylpropyl]-1,3-benzothiazol-2(3H)-one;
   1-isopropyl-3-[(1R)-3-(methylamino)-1-phenylpropyl]-1,3-dihydro-2H-benzimidazol-2-ylidene}cyanamide;
   1-[(1R)-3-amino-1-phenylpropyl]-3-ethyl-1,3-dihydro-2H-benz-imidazol-2-one;
   1-ethyl-3-[(1R)-3-(ethylamino)-1-phenylpropyl]-1,3-dihydro-2H-benzimidazol-2-one;
   1-[(1R)-3-(dimethylamino)-1-phenylpropyl]-3-ethyl-1,3-dihydro-2H-benzimidazol-2-one;
   4-fluoro-1-isopropyl-3-[(1S)-3-(methylamino)-1-phenylpropyl]-1,3-dihydro-2H-benzimidazol-2-one;
   4-fluoro-1-isopropyl-3-[(1R)-3-(methylamino)-1-phenylpropyl]-1,3-dihydro-2H-benzimidazol-2-one;
   3-[(1R)-3-(dimethylamino)-1-phenylpropyl]-4-fluoro-1-isopropyl-1,3-dihydro-2H-benzimidazol-2-one;
   {(2Z)-3-[(1R)-3-(dimethylamino)-1-phenylpropyl]-5-fluoro-1-propyl-1,3-dihydro-2H-benzimidazol-2-ylidene}cyanamide;
   (3R)-3-(7-fluoro-3,3-dimethyl-2,3-dihydro-1H-indol-1-yl)-3-(3-fluorophenyl)-N-methylpropan-1-amine;
   1-[(1R)-1-(3-chloro-5-fluorophenyl)-3-(methylamino)propyl]-7-fluoro-3,3-dimethyl-1,3-dihydro-2H-indol-2-one;
   1-[(1R)-1-(3,5-difluorophenyl)-3-(methylamino)propyl]-7-fluoro-3,3-dimethyl-1,3-dihydro-2H-indol-2-one;
   1-[(1R)-1-(3-chlorophenyl)-3-(methylamino)propyl]-7-fluoro-3,3-dimethyl-1,3-dihydro-2H-indol-2-one;
   4-fluoro-1-(2-fluorophenyl)-3-[(1R)-3-(methylamino)-1-phenylpropyl]-1,3-dihydro-2H-benzimidazol-2-one;
   1-ethyl-4-fluoro-3-[(1R)-1-(3-fluorophenyl)-3-(methylamino)propyl]-1,3-dihydro-2H-benzimidazol-2-one; or
a pharmaceutically acceptable salt thereof.

38. A pharmaceutical composition, comprising:
   a. at least one compound according to claim 1 or a pharmaceutically acceptable salt thereof; and
   b. at least one pharmaceutically acceptable carrier.

* * * * *